US008163493B2

(12) United States Patent
Eng et al.

(10) Patent No.: US 8,163,493 B2
(45) Date of Patent: Apr. 24, 2012

(54) TARGETS FOR USE IN DIAGNOSIS, PROGNOSIS AND THERAPY OF CANCER

(75) Inventors: Charis Eng, Cleveland Heights, OH (US); Frank Weber, Essen (DE)

(73) Assignee: The Cleveland Clinic Foundation, Cleveland, OH (US)

( * ) Notice: Subject to any disclaimer, the term of this patent is extended or adjusted under 35 U.S.C. 154(b) by 417 days.

(21) Appl. No.: 12/343,871

(22) Filed: Dec. 24, 2008

(65) Prior Publication Data

US 2011/0014603 A1    Jan. 20, 2011

Related U.S. Application Data

(63) Continuation of application No. PCT/US2007/015265, filed on Jun. 28, 2007.

(60) Provisional application No. 60/874,409, filed on Dec. 12, 2006, provisional application No. 60/817,249, filed on Jun. 28, 2006, provisional application No. 60/843,271, filed on Sep. 8, 2006, provisional application No. 60/928,796, filed on May 11, 2007.

(51) Int. Cl.
*C12Q 1/68* (2006.01)
(52) U.S. Cl. ..................................... 435/6.14
(58) Field of Classification Search .................. None
See application file for complete search history.

(56) References Cited

U.S. PATENT DOCUMENTS

| 2003/0165895 | A1 | 9/2003 | Czerniak et al. |
| 2010/0092961 | A1 | 4/2010 | Eng |
| 2010/0159466 | A1 | 6/2010 | Eng |
| 2010/0255478 | A1 | 10/2010 | Eng |

FOREIGN PATENT DOCUMENTS

| WO | WO 2005/078139 A | 8/2005 |
| WO | WO 2005/118806 A | 12/2005 |
| WO | WO 2006/028967 A | 3/2006 |
| WO | WO 2008/002672 | 1/2008 |

OTHER PUBLICATIONS

Ada-Nguema, A. S., et al., "The Small GTPase R-Ras Regulates Organization of Actin and Drives Membrane Protrusions Through the Activity of PLCε," *Journal of Cell Science*, 119:1307-1319 (2006).
Antoniou, A. C., et al., "A Comprehensive Model for Familial Breast Cancer Incorporating BRCA1, BRCA2 and Other Genes," *British Journal of Cancer*, 86:76-83 (2002).
Barclay, W. W., et al., "A System for Studying Epithelial-Stromal Interactions Reveals Distinct Inductive Abilities of Stromal Cells from Benign Prostatic Hyperplasia and Prostate Cancer," *Endocrinology*, 146(1):13-18 (Jan. 2005).
Baysal, B.E., et al., "Mutations in *SDHD*, a Mitochondrial Complex II Gene, in Hereditary Paraganglioma," *Science*, 287:848-851 (Feb. 4, 2000).
Benn, D.E., et al., "Clinical Presentation and Penetrance of Pheochromocytoma/Paraganglioma Syndromes," *The Journal of Clinical Endocrinology & Metabolism*, 91 (3):827-836 (2006; Online Nov. 29, 2005).
Cascon, A., et al., "G12S and H50R Variations are Polymorphisms in the *SDHD* Gene," *Genes, Chromosomes & Cancer*, 37:220-221 (2003).
Chen, S.-L., et al., "*p53* is a Regulator of the Metastasis Suppressor Gene *Nm23-H1*," *Molecular Carcinogenesis*, 36:204-214 (2003).
Chung, J.-H., et al., "Nuclear-Cytoplasmic Partitioning of Phosphatase and Tensin Homologue Deleted on Chromosome 10 (PTEN) Differentially Regulates the Cell Cycle and Apoptosis," *Cancer Res.*, 65(18):8096-8100 (Sep. 15, 2005).
Eissa, S., et al., "Multivariate Analysis of DNA ploidy, P53, c-erbB-2 Proteins, EGFR, and Steroid Hormone Receptors for Short Term Prognosis in Breast Cancer," *Anticancer Research*, 17(4B):3091-3098 (Jul.-Aug. 1997).
Eng, C., et al., "A Role for Mitochondrial Enzymes in Inherited Neoplasia and Beyond," *Nature Reviews Cancer*, 3:193-202 (Mar. 2003).
Gasco, M., et al., "TP53 Mutations in Familial Breast Cancer: Functional Aspects," *Human Mutation*, 21:301-306 (2003).
Hainaut, P., and Hollstein, M., "p53 and Human Cancer: The First Ten Thousand Mutations," *Advances in Cancer Research*, 77:81-137 (2000).
Hartman, A.-R., and Ford, J. M., "BRCA1 Induces DNA Damage Recognition Factors and Enhances Nucleotide Excision Repair," *Nature Genetics*, 32:180-184 (Sep. 2002).
Hayward, S. W., et al., "Malignant Transformation in a Nontumorigenic Human Prostatic Epithelial Cell Line," *Cancer Research*, 61:8135-8142 (Nov. 15, 2001).
Hollstein, M., et al., "p53 Mutations in Human Cancers," *Science*, 253:49-53 (Jul. 5, 1991).
Ishii, T., et al., "A Mutation in the *SDHC* Gene of Complex II Increases Oxidative Stress, Resulting in Apoptosis and Tumorigenesis," *Cancer Res.*, 65(1):203-209 (Jan. 1, 2005).
Kastan, M. B., and Bartek, J., "Cell-Cycle Checkpoints and Cancer," *Nature*, 432:316-323 (Nov. 18, 2004).
Koivunen, P., et al., "Inhibition of Hypoxia-inducible Factor (HIF) Hydroxylases by Citric Acid Cycle Intermediates Possible Links Between Cell Metabolism and Stabilization of HIF," *The Journal of Biological Chemistry*, 282(7):4524-4532 (Feb. 16, 2007).
Kryukov, G.V., et al., "Most Rare Misense Alleles are Deleterious in Humans: Implications for Complex Disease and Association Studies," *The American Journal of Human Genetics*, 80:727-739 (Apr. 2007).
Kurose, K., et al., Erratum: "Frequent Somatic Mutations in PTEN and TP53 are Mutually Exclusive in the Stroma of Breast Carcinomas," *Nature Genetics*, 32:681 (Dec. 2002).
Kytölä, S., et al., "Alterations of the *SDHD* Gene Locus in Midgut Carcinoids, Merkel Cell Carcinomas, Pheochromocytomas, and Abdominal Paragangliomas," *Genes, Chromosomes & Cancer*, 34:325-332 (2002).
Launonen, V., et al., "Inherited Susceptibility to Uterine Leiomyomas and Renal Cell Cancer," *PNAS*, 98(6):3387-3392 (Mar. 13, 2001).
Lee, S.-R., et al., "Reversible Inactivation of the Tumor Suppressor PTEN by $H_2O_2$," *The Journal of Biochemical Chemistry* 277(23):20336-20342 (Jun. 7, 2002).
Liaw, D., et al., "Germline Mutations of the *PTEN* Gene in Cowden Disease, an Inherited Breast and Thyroid Cancer Syndrome," *Nature Genetics*, 16:64-67 (May 1997).
Maffini, M. V., et al., "Stromal Regulation of Neoplastic Development: *Age-Dependent Normalization of Neoplastic Mammary Cells by Mammary Stroma*," *American Journal of Pathology* 167(5):1405-1410 (Nov. 2005).

(Continued)

*Primary Examiner* — James Martinell
(74) *Attorney, Agent, or Firm* — Hamilton, Brook, Smith & Reynolds, P.C.

(57) ABSTRACT

Provided herein are targets that can be used for the diagnosis, prognosis and therapy of a variety of cancers.

7 Claims, 18 Drawing Sheets

OTHER PUBLICATIONS

Marsh, D.J., et al., "Mutation Spectrum and Genotype-phenotype Analyses in Cowden Disease and Bannayan-Zonana Syndrome, Two Hamartoma Syndromes with Germline *PTEN* Mutation," *Human Molecular Genetics*, 7(3):507-515 (1998).

Martin, A.-M., et al., "Germline *TP53* Mutations in Breast Cancer Families with Multiple Primary Cancers: Is *TP53* a Modifier of *BRCA1?*," *J. Med. Genet.*, 40(/e34):1-6 (2003).

Matrisian, L. M., et al., "Epithelial-Stromal Interactions and Tumor Progression: Meeting Summary and Future Directions," *Cancer Research*, 61:3844-3846 (May 1, 2001).

McWhinney, S.R., et al., "Large Germline Deletions of Mitochondrial Complex II Subunits *SDHB* and *SDHD* in Hereditary Paraganglioma," *The Journal of Clinical Endocrinology & Metabolism*, 89(11):5694-5699 (2004).

Mutter, G.L., et al., "Altered PTEN Expression as a Diagnostic Marker for the Earliest Endometrial Precancers," *Journal of National Cancer Institute*, 92(11):924-931 (Jun. 7, 2000).

Narod, S. A., and Foulkes, W. D., "BRCA1 and BRCA2: 1994 and Beyond," *Nature*, 4:665-676 (Sep. 2004).

Neumann, H.P.H., et al., "Germ-line Mutations in Nonsyndromic Pheochromocytoma," *N. Engl. J. Med.*, 346(19):1459-1466 (May 9, 2002).

Ni, Y., et al., "Germline Mutations and Variants in the Succinate Dehydrogenase Genes in Cowden and Cowden-like Syndromes," *The American Journal of Human Genetics*, 83:261-268 (Aug. 8, 2008).

Overgaard, J., et al., "*TP53* Mutation is an Independent Prognostic Marker for Poor Outcome in Both Node-negative and Node-positive Breast Cancer," *Acta Oncologica* 39:(3)327-333 (2000).

Patocs, A., et al., "Breast-Cancer Stromal Cells with *TP53* Mutations and Nodal Metastases," *The New England Journal of Medicine.*, 357(25):2543-2551 (Dec. 20, 2007).

Perren, A., et al., "Absence of Somatic *SDHD* Mutations in Sporadic Neuroendocrine Tumors and Detection of Two Germline Variants in Paraganglioma Patients," *Oncogene*, 21:7605-7608 (2002).

Pharoah, P. D. P., et al., "Somatic Mutations in the *p53* Gene and Prognosis in Breast Cancer: A Meta-Analysis," *British Journal of Cancer*, 80(12): 1968-1973 (1999).

Selak, M.A., et al., "Succinate Links TCA Cycle Dysfunction to Oncogenesis by Inhibiting HIF-α Prolyl Hydroxylase," *Cancer Cell*, 7:77-85 (Jan. 2005).

Slane, B.G., et al., "Mutation of Succinate Dehydrogenase Subunit C Results in Increased $O_2$Oxidative Stress, and Genomic Instability," *Cancer Res.*, 66(15):7615-7620 (Aug. 1, 2006).

Smith, P. D., et al., "Novel p53 Mutants Selected in BRCA-Associated Tumours Which Dissociate Transformation Suppression from Other Wild-type p53 Functions," *Oncogene*, 18:2451-2459 (1999).

Stambolic, V., et al., "High Incidence of Breast and Endometrial Neoplasia Resembling Human Cowden Syndrome in pten $^{frax;+;-}$ Mice," *Cancer Research*, 60:3605-3611 (Jul. 1, 2000).

Tang, Y. and Eng, C., "PTEN Autoregulates Its Expression by Stabilization of p53 in a Phosphatase-Independent Manner," *Cancer Research*, 66(2):736-742 (Jan. 15, 2006).

Vanharanta, S., et al., "Early-Onset Renal Cell Carcinoma as a Novel Extraparaganglial Component of *SDHB*-Associated Heritable Paraganglioma," *Am. J. Hum. Genet.*, 74:153-159 (2004; electronically Dec. 18, 2003).

Wang, X., et al., "p63 Expression in Normal, Hyperplastic and Malignant Breast Tissues," *Breast Cancer*, 9(3):216-219 (Jul. 2002).

Weng, L.-P., et al., "PTEN Blocks Insulin-mediated ETS-2 Phosphorylation Through MAP Kinase, Independently of the Phosphoinositide 3-kinase Pathway," *Human Molecular Genetics*, 11(15):1687-1696 (2002).

Yang, W.-W., et al., "E2F6 Negatively Regulates Ultraviolet-Induced Apoptosis via Modulation of BRCA1," *Cell Death and Differentiation*, 14:807-817 (2007).

Zbuk, K.M and Eng, C., "Cancer Phenomics: *RET* and *PTEN* as Illustrative Models," *Nature Reviews Cancer*, 7:35-45 (Jan. 2007).

6th edition of the American Joint Committee on Cancer (AJCC) Cancer Staging Manual (Greene, F., et al., eds. AJCC Cancer Staging Manual, 6th edition, New York: Springer-Verlag; (2002)). pp. ix, xi, and xii.

Allinen, M., et al., "Molecular Characterization of the Tumor Microenvironment in Breast Cancer," *Cancer Cell* 617-32 (2004).

A Conference on Nonparametric Inference and Probability with Applications to Science (Honoring Michael Woodroofe), Ann Arbor, Michigan, 2005). The R package (http://www.r-project,org).

Aldred, M.A., et al., "Papillary and Follicular Thyroid Carcinomas Show Distinctly Different Microarray Expression Profiles and can be Distinguished by a Minimum of Five Genes," *J Clin Onco.* 22(17):3531-3539 (2004).

Aldred, M.A., et al., "Peroxisome Proliferator-activated Receptor Gamma is Frequently Downregulated in a Diversity of Sporadic Nonmechillary Thyroid Carcinomas," *Oncogene* 22:3412-3416 (2003).

Alvarez-Garcia, I., et al., "MicroRNA Functions in Animal Development and Human Disease," *Development 132*(21):4653-4662 (2005).

Appelhoff, R,J., et al., "Differential Function of the Prolyl Hydorxylases PHD1, PHD2, and PHD3 in the Regulation of Hypoxia-inducible Factor," *J of Bio Chem 279*(37):38458-38465 (2004).

Argraves, W.S., et al., "Fibulins: Physiological and Disease Perspectives," *EMBO Reports 4*(12):1127-1131 (2003).

Auer, H., et al., "Chipping Away at the Chip Bias: RNA Degradation in Microarray Analysis," *Nature Genetics 35*(4):292-293 (2003).

Berezikov, E., et al., "Approaches to MicroRNA Discovery," *Nature Genetics 38*:S2-S7 (2006).

Bhowmick, N.A., et al., "Stromal Fibroblasts in Cancer Initiation and Progression," *Nature 432*:332-337 (2004).

Bissell, M.J., et al.,"The Influence of Extracellular Matrix on Gene Expression: Is Structure the Message?," *J. Cell Sci. Suppl 8*:327-343 (1987).

Bockmühl, U., et al., "Chromosomal Alterations During Metastasis Formation of Head and Neck Squamous Cell Carcinoma," *Genes, Chromosomes & Cancers 33*:29-35 (2002).

Bockmühl, U., MD, et al., "Genomic Alterations Associated with Malignancy in Head and Neck Cancer," *Head & Neck 20*:145-151 (1998).

Bonneau, D., et al., "Mutations of the Human PTEN Gene," *Human Mutation 16*:109-122 (2000).

Boucheix, C., et al., "Tetraspanins and Malignancy," *Expert Reviews in Molecular Medicine*:1-17 (2001).

Braakhuis, B.J.M., et al., "A Genetic Explanation of Slaughter's Concept of Field Cancerization: Evidence and Clinical Implications," *Cancer Research 63*:1727-1730 (2003).

Braakhuis, B.J.M., et al., "Expanding Fields of Genetically Altered Cells in Head and Neck Squamous Carcinogenesis," *Seminars in Cancer Biology 15*:113-120 (2005).

Calin, G.A., MD, PhD, et al., "A MicroRNA Signature Associated with Prognosis and Progression in Chronic Lymphocytic Leukemia," *N Engl J Med 353*(17):1793-1801 (2005).

Canobbio, I., et al., "Altered Cytoskeleton Organization in Platelets from Patients with MYH9-related Disease," *J of Thrombosis and Haemostasis 3*:1026-1035 (2005).

Carethers, J.M., et al., "Absence of *PTEN/MMAC1* Germ-Line Mutations in Sporadic Bannayan-Riley-Ruvalcaba Syndrome," *Cancer Research 58*:2724-2726 (1998).

Cerutti, J.M., et al., "A Preoperative Diagnostic Test that Distinguishes Benign from Malignant Thyroid Carcinoma Based on Gene Expression," *The Journal of Clinical Investigation* 113(8):1234-1242 (2004).

Chen, C.-Z., Ph.D., "MicroRNAs as Oncogenes and Tumor Suppressors," *N Engl J Med 353*:1768-1771 (2005).

Chen, E.I., et al., "Maspin and Tumor Metastasis," *IUBMB Life 58*(1):25-29 (2006).

Climent, J., et al., "Genomic Loss of 18p Predicts an Adverse Clinical Outcome in Patients with High-Risk Breast Cancer," *Clinical Cancer Research 83*863-3869 (2002).

Cocco, L., et al., "Nuclear Phospholipase C β1, Regulation of the Cell Cycle and Progression of Acute Myeloid Leukemia," *Advan. Enzyme Regul 45*:126-135 (2005).

Condon, M.S., "The Role of the Stromal Microenvironment in Prostate Cancer," *Seminars in Cancer Biology 15*:132-137 (2005).

Cornélius, F., et al., "New Susceptibility Locus for Rheumatoid Arthritis Suggested by a Genome-Wide Linkage Study," *Proc. Natl. Acad Sci. USA* 95:10746-10750 (1998).
Cuneo, A., et al., "Acquired Chromosome 11q Deletion Involving the Ataxia Teleangiectasia Locus in B-Cell Non-Hodgkin's Lymphoma: Correlation with Clinicobiologic Features," *J of Clin Oncology* 18(13):2607-2614 (2000).
Dacic, S., MD, et al., "Patterns of Allelic Loss of Synchronous Adenocarcinomas of the Lung," *Am J Surg Pathol* 29(7):897-902 (2005).
Dai, M.-S., et al., "The Effects of the Fanconi Anemia Zinc Finger (FAZF) on Cell Cycle, Apoptosis, and Proliferation are Differentiation Stage-spceific," *The J. of Biological Chem* 277(29):26327-26334 (2002).
Debies, M.T., et al., "Genetic Basis of Human Breast Cancer Metastasis," *J of Mammary Gland Biology and Neoplasia* 6(4):441-451 (2001).
Denison, S.R., et al., "Characterization of FRA6E and Its Potential Role in Autosomal Recessive Juvenile Parkinsonism and Ovarian Cancer," *Genes, Chromosomes & Cancer* 38:40-52 (2003).
Drysdale, C.M., et al., "Complex Promoter and Coding Region $\beta_2$-adrenergic Receptor Haplotypes Alter Receptor Expression and Predict in vivo Responsiveness," *PNAS* 97(19):10483-10488 (2000).
Edlund, M., et al., "Modulation of Prostate Cancer Growth in Bone Microenvironments," *Journal of Cellular Biochemistry* 91:686-705 (2004).
Ellsworth, R.E., et al., "Allelic Imbalance in Primary Breast Carcinomas and Metastatic Tumors of the Axillary Lymph Nodes," *Molecular Cancer Research* 3(2):71-77 (2005).
Eng, C., "Will the Real Cowden Syndrome Please Stand Up: Revised Diagnostic Criteria," *J Med Genet* 37:828-830 (2000).
Fagin, J.A., "Perspective: Lessons Learned from Molecular Genetic Studies of Thyroid Cancer-Insights into Pathogenesis and Tumor-Specific Therapeutic Targets," *Endocrinology* 143(6):2025-2028 (2002).
Farahati, J., et al., "Changing Trends of Incidence and Prognosis of Thyroid Carcinoma in Lower Franconia, Germany, from 1981-1995," *Thyroid* 14(2):141-147 (2004).
Forastiere, A., M.D., et al., "Head and Neck Cancer," *N Engl J Med* 345(26):1890-1900 (2001).
Fukino, K., et al., "Combined Total Genome Loss of Heterozygosity Scan of Breast Cancer Stroma and Epithelium Reveals Multiplicity of Stromal Targets," *Cancer Research* 64:7231-7236 (2004).
Fukino, K., et al., "Genomic Instability Within Tumor Stroma and Clinicopathological Characteristics of Sporadic Primary Invasive Breast Carcinoma," *JAMA* 297(19):2103-2111 (2007).
Gallagher, W.M., et al., "Human Fibulin-4: Analysis of its Biosynthetic Processing and mRNA Expression in Normal and Tumour Tissues," *FEBS Letters* 489:59-66 (2001).
Ginzinger, D.G., et al., "Measurement of DNA Copy Number at Microsatellite Loci Using Quantitative PCR Analysis," *Cancer Research* 60:5405-5409 (2000).
Gort, M., et al., "Improvement of Best Practice in Early Breast Cancer: Actionable Surgeon and Hospital Factors," *Breast Cancer Res Treat* 102:219-226 (2007).
Götte, K., et al., "Intratumoral Genomic Heterogeneity in Advanced Head and Neck Cancer Detected by Comparative Genomic Hybridization," *Current Research in Head and Neck Cancer* 62:38-48 (2005).
Greenwood, T.A., et al., "Promoter and Intronic Variants Affect the Transcriptional Regulation of the Human Dopamine Transporter Gene," *Genomics* 82:511-519 (2003).
Grünweller, A., et al., "RNA Interferences as a Gene-Specific Approach for Molecular Medicine," *Current Medicinal Chemistry* 12:3143-3161 (2005).
Haiman, C.A., et al., "Common Genetic Variation at *PTEN* and Risk of Sporadic Breast and Prostate Cancer," *Cancer Epidemiol Biomarkers Prev* 15(5):1021-1025 (2006).
Hamilton, J.A., et al., "The Expression Profile for the Tumour Suppressor Gene *PTEN* and Associated Polymorphic Markers," *British Journal of Cancer* 82(10):1671-1676 (2000).
Hartikainen, J.M., et al., "An Autosome-wide Scan for Linkage Disequilibrium-based Association in Sporadic Breast Cancer Cases in Eastern Finland: Three Candidate Regions Found," *Cancer Epidemiology, Biomarkers & Prevention* 14(1):75-80 (2005).
He, H., et al., "The Role of MicroRNA Genes in Papillary Thyroid Carcinoma," *PNAS* 102(52):19075-19080 (2005).
Hill, R., et al., "Selective Evolution of Stromal Mesenchyme with p53 Loss in Response to Epithelial Tumorigenesis," *Cell* 123:1001-1011 (2005).
Hoatlin, M.E., et al., "A Novel BTB/POZ Transcriptional Repressor Protein Interacts with the Fanconi Anemia Group C Protein and PLZF," *Blood* 94:3737-3747 (1999).
Horváth, B., MD, et al., "Expression of ETS-1 Transcription Factor in Human Head and Neck Squamous Cell Carcinoma and Effect of Histamine on Metastatic Potential of Invasive Tumor Through the Regulation of Expression of ETS-1 and Matrix Metalloproteinase-3," *Head & Neck* 27:585-596 (2005).
Hu, M., et al., "Distinct Epigenetic Changes in the Stromal Cells of Breast Cancers," *Nature Genetics* 37(8):899-905 (2005).
Huang, Q., et al., "Genetic Differences Detected by Comparative Genomic Hybridization in Head and Neck Squamous Cell Carcinomas from Different Tumor Sites: Construction on Oncogenetic Trees for Tumor Progression," *Genes, Chromosomes & Cancer* 34:224-233 (2002).
Hunter, K.D., et al., "Profiling Early Head and Neck Cancer," *Cancer* 5:127-135 (2005).
Hussain, S., et al., "Direct Interaction of FANCD2 with BRCA2 in DNA Damage Response Pathways," *Human Molecular Genetics* 13(12):1241-1248 (2004).
Iorio, M.V., et al., "MicroRNA Gene Expression Deregulation in Human Breast Cancer," *Cancer Res* 65(16):7065-7070 (2005).
Jang, S.J., et al., "Multiple Oral Squamous Epithelial Lesions: Are They Genetically Related?," *Oncogene* 20:2235-2242 (2001).
Jukkola, T., et al.,"*Drapc1* Expression During Mouse Embryonic Development," *Gene Expression Patterns* 4:755-762 (2004).
Kebebew, E., MD, "Diagnostic and Prognostic Value of Angiogenesis-Modulating Genes in Malignant Thyroid Neoplasms," *Surgery* 138:1102-1110 (2005).
Khanna, K.K., et al., "ATM and Genome Maintenance: Defining Its Role in Breast Cancer Susceptibility," *J of Mammary Gland Biology and Neoplasia* 9(3):247-262 (2004).
Kimura, E.T., et al., "High Prevalence of *BRAF* Mutations in Thyroid Cancer: Genetic Evidence for Constitutive Activation of the RET/PTC-RAS-BRAF Signaling Pathway in Papillary Thyroid Carcinoma," *Cancer Research* 63:1454-1457 (2003).
Kleinjan, D.A., et al., "Long-Range Control of Gene Expression: Emerging Mechanisms and Disruption in Disease," *Am. J. Hum. Genet.* 76:8-32 (2005).
Kraiem, Z., et al., "Matrix Metalloproteinases and the Thyroid," *Thyroid* 10(12):1061-1069 (2000).
Krubasik, D., et al., "Absence of p300 Induces Cellular Phenotypic Changes Characteristic of Epithelial to Mesenchyme Transition," *British Journal of Cancer* 94:1326-1332 (2006).
Krützfeldt, J., et al., "Silencing of MicroRNAs in vivo with 'antagomirs'," *Nature* 438:685-689 (2005).
Kurose, K., et al., "Genetic Model of Multi-Step Breast Carcinogenesis Involving the Epithelium and Stroma: Clues to Tumour-Microenvironment Interactions," *Human Molecular Genetics* 10(18):1907-1913 (2001).
Kurosc, K., et al., "Frequent Somatic Mutations in *PTEN* and *TP53* are Mutually Exclusive in the Stroma of Breast Carcinomas," *Nature Genetics* 32:355-357 (2002).
Lagos-Quintana, M., et al., "New MicroRNAs from Mouse and Human," *RNA* 9:175-179 (2003).
Leng, K., et al., "Refined Characterization of Head and Neck Squamous Cell Carcinomas Expressing a Seemingly Wild-type p53 Protein," *J Oral Pathol Med* 35:19-24 (2006).
Liu, C.-G., et al., "An Oligonucleotide Microchip for Genome-wide MicroRNA Profiling in Human and Mouse Tissues," *PNAS* 101(26):9740-9744 (2004).
Loffeld, A., et al., "Epidermal Naevus in Proteus Syndrome Showing Loss of Heterozygosity for an Inherited *PTEN* Mutation," *British Journal of Dermatology* 154:1194-1198 (2006).
Lu, J., et al., "MicroRNA Expression Profiles Classify Human Cancers," *Nature* 435:834-838 (2005).

Maehama, T., et al., "The Tumor Suppressor, PTEN/MMAC1, Dephosphorylates the Lipid Second Messenger, Phosphatidylinositol 3,4,5-Trisphosphate," *The Journal of Biological Chemistry* 273(22):13375-13378 (1998).

Marsh, D.J., et al., "Differential Loss of Heterozygosity in the Region of the Cowden Locus Within 10q22-23 in Follicular Thyroid Adenomas and Carcinomas," *Cancer Research* 57:500-503 (1997).

Marsh, D.J., et al., "*PTEN* Mutation Spectrum and Genotype-Phenotype Correlations in Bannayan-Riley-Ruvalcaba Syndrome Suggest a Single Entity with Cowden Syndrome," *Human Molecular Genetics* 8(8):1461-1472 (1999).

McCawley, L.J., et al., "Tumor Progression: Defining the Soil Round the Tumor Seed," *Current Biology* 11:R25-R27 (2001).

Miska, E.A., "How MicroRNAS Control Cell Division, Differentiation and Death," *Current Opinion in Genetics & Development* 15:563-568 (2005).

Moinfar, F., et al., "Concurrent and Independent Genetic Alterations in the Stromal and Epithelial Cells of Mammary Carcinoma: Implications for Tumorigenesis," *Cancer Research* 60:2562-2566 (2000).

Mueller, M.M., et al., "Friends or Foes—Bipolar Effects of the Tumour Stroma in Cancer," *Cancer* 4:839-849 (2004).

Murakami, Y., et al., "Comprehensive Analysis of MicroRNA Expression Patterns in Hepatocellular Carcinoma and Non-Tumorous Tissues," *Oncogene* 25:2537-2545 (2006).

Naguibneva, I., et al., "The MicroRNA *miR-181* Targets the Homeobox Protein Hox-A11 During Mammalian Myoblast Differentiation," *Nature Cell Biology* 8(3):278-284 (2006).

Nelson, H.H., et al.,"*TP53* Mutation, Allelism and Survival in Non-small Cell Lung Cancer," *Carcinogenesis* 26(10): 1770-1773 (2005).

Nigro, J.M., et al., "Technical Advance Detection of 1p and 19q Loss in Oligodendroglioma by Quantitative Microsatellite Analysis, a Real-Time Quantitative Polymerase Chain Reaction Assay," *American Journal of Pathology* 158(4):1253-1262 (2001).

Passler, C., et al., "Prognostic Factors of Papillary and Follicular Thyroid Cancer: Differences in an Iodine-Replete Endemic Goiter Region," *Endocrine-Related Cancer* 11:131-139 (2004).

Perez-Ordoñez, B., et al., "Molecular Biology of Squamous Cell Carcinoma of the Head and Neck," *J Clin Pathol* 59:445-453 (2006).

Pilarski, R., et al., "Will the Real Cowen Syndrome Please Stand Up (Again)? Expanding Mutational and Clinical Spectra of the *PTEN* Hamartoma Tumour Syndrome," *J Med Genet* 41:323-326 (2004).

Poy, M.N., et al., "A Pancreatic Islet-Specific MicroRNA Regulates Insulin Secretion," *Nature* 432:226-230 (2004).

Radmacher, M.D., et al., "A Paradigm for Class Prediction Using Gene Expression Profiles," *Journal of Computational Biology* 9(3):505-511 (2002).

Ricci, F., et al., "Stromal Responses to Carcinomas of the Pancreas," *Cancer Biology & Therapy* 4(3):302-307 (2005).

Ries, L.A.G., et al., "Surveillance Epidemiology and End Results," *Cancer Statistics Review National Cancer Institute* 1975-2003 (2006).

Rio, P.G., et al., "Loss of Heterozygosity of *BRCA1*, *BRCA2* and *ATM* Genes in Sporadic Invasive Ductal Breast Carcinoma," *International Journal of Oncology* 13:849-853 (1998).

Rosenquist, T.A., et al., "The Novel DNA Glycosylase, NEIL 1, Protects Mammalian Cells from Radiation-mediated Cell Death," *DNA Repair* 2:581-591 (2003).

Rosenthal, F.., et al., "Elevated Expression of TGF-β1 in Head and Neck Cancer-Associated Fibroblasts," *Molecular Carcinogenesis* 40:116-121 (2004).

Sarquis, M.S., et al., "High Frequency of Loss of Heterozygosity in Imprinted, Compared with Nonimprinted, Genomic Regions in Follicular Thyroid Carcinomas and Atypical Adenomas," *The Journal of Clinical Endocrinology & Metabolism* 91(1):262-269 (2006).

Schedin, P., et al., "Multistep Tumorigenesis and the Microenvironment," *Breast Cancer Res* 6:93-101 (2004).

Schulte, K,-M., et al., "Activin A and Activin Receptors in the Human Thyroid: A Link to the Female Predominance of Goiter?," *Horm Metab Res* 32:390-400 (2000).

Schulte, K.-M., et al "Activin A and Activin Receptors in Thyroid Cancer," *Thyroid* 11(1):3-14 (2001).

Segev, D.L., M.D., et al., "Beyond the Suspicious Thyroid Fine Needle Aspirate A Review," *Acta Cytol* 47:709-722 (2003).

Segev, D.L., et al., "Molecular Pathogenesis of Thyroid Cancer," *Surgical Oncology* 12:69-90 (2003).

Shekhar, M.P.V., et al., "Breast Stroma Plays a Dominant Regulatory Role in Breast Epithelial Growth and Differentiation: Implications for Tumor Development and Progression," *Cancer Research* 61:1320-1326 (2001).

Shiozawa, S., et al., "Identification of the Gene Loci that Predispose to Rheumatoid Arthritis," *International Immunology* 10(12):1891-1895 (1998).

Simpson, P.T., et al., "Molecular Evolution of Breast Cancer," *J Pathol* 205:248-254 (2005).

Slager, S.L., et al,, "Confirmation of Linkage of Prostate Cancer Aggressiveness with Chromosome 19q," *Am. J. Hum. Genet.* 72:759-762 (2003).

Slaughter, D.P., et al.," 'Field Cancerization' in Oral Stratified Squamous Epithelium Clinical Implications of Multicentric Origin," *Cancer* 6:963-8 (1953).

Smith, J.M., et al., "Germline Mutation of the Tumour Suppressor *PTEN* in Proteus Syndrome," *J Med Genet* 39:937-940 (2002).

Taniguchi, T., et al., "S-Phase-Specific Interaction of the Fanconi Anemia Protein, FANCD2, with BRCA1 and RAD51," *Blood* 100(7):2414-2420 (2002).

Tuhkanen, H., et al., "Genetic Alterations in the Peritumoral Stromal Cells of Malignant and Borderline Epithelial Ovarian Tumors as Indicated by Allelic Imbalance on Chromosome 3P," *Int J. Cancer* 109:247-252 (2004).

Tran, Y., et al., "Novel Regions of Allelic Deletion on Chromosome 18p in Tumors of the Lung, Brain and Breast," *Oncogene* 17:3499-3505 (1998).

Umbricht, C.B., et al., "Human Telomerase Reverse Transcriptase Gene Expression and the Surgical Management of Suspicious Thyroid Tumors," *Clinical Cancer Research* 10:5762-5768 (2004).

van Oijen, M.G.C.T., et al., "Oral Field Characterization: Carcinogen-induced Independent Events or Micrometastatic Deposits," *Cancer Epidemiology, Biomarkers & Prevention* 9:249-256 (2000).

Volinia, S., et al., "A MicroRNA Expression Signature of Human Solid Tumors Defines Cancer Gene Targets," *Proceedings of the National Academy of Sciences USA* 103(7):2257-2261 (2006).

Weber, F., et al,, "Total-Genome Analysis of *BRCA1/2*-Related Invasive Carcinomas of the Breast Identifies Tumor Stroma as Potential Landscaper for Neoplastic Initiation," *The American Journal of Human Genetics* 78:961-972 (2006).

Weber, F., et al,, "Variability in Organ-Specific *EGFR* Mutational Spectra in Tumour Epithelium and Stroma may be the Biological Basis for Differential Responses to Tyrosine Kinase Inhibitors," *British Journal of Cancer* 92:1922-1926 (2005).

Weber, F., et al., "Gene-expression Profiling in Differentiated Thyroid Cancer—a Viable Strategy for the Practice of Genomic Medicine," *Future Oncol.* 1(4):497-510 (2005).

Weber, F., et al., "Silencing of the Maternally Imprinted Tumor Suppressor *ARH1* Contributes to Follicular Thyroid Carcinogenesis," *The Journal of Clinical Endocrinology & Metabolism* 90(2):1149 -1155 (2005).

Weber, F., M.D., et al,, "Microenvironmental Genomic Alterations and Clinicopathological Behavior in Head and Neck Squamous Cell Carcinoma," *JAMA* 297(2)187-195 (2007).

Weber, F., et al., "A Limited Set of Human MicroRNA is Deregulated in Follicular Thyroid Carcinoma," *Journal Clinical Endocrinology & Metabolism* 91(9):3584-3591 (2006).

Weigelt, B., et al., "No Common Denominator for Breast Cancer Lymph Node Metastasis," *British Journal of Cancer* 93:924-932 (2005).

Weiler, J., et al., "Anti-miRNA Oligonucleotides (AMOs): Ammunition to Target miRNAs Implicated in Human Disease," *Gene Therapy* 13:496-502 (2006).

Wernert, N., et al., "Presence of Genetic Alterations in Microdissected Stroma of Human Colon and Breast Cancers," *Anticancer Research* 21:2259-2264 (2001).

Williams, H.K., et at., "Molecular Pathogenesis of Oral Squamous Carcinoma," *J. Clin Pathol: Mol Pathol* 53:165-172 (2000).

Witte, J.S., et al., "Genomewide Scan for Prostate Cancer—Aggressiveness Loci," *Am. J. Hum. Genet.* 67:92-99 (2000).

Worsham, M.J., et al., "Fine-Mapping Loss of Gene Architecture at the *CDKN2B* ($p15^{INK4b}$), *CDKN2A* ($p14^{ARF}$, $p16^{INK4a}$) and *MTAP* Genes in Head and Neck Squamous Cell Carcinoma," *Arch Otolaryngol Head Neck Surg.* 132:409-415 (2006).

Yanaihara, N., et al., "Unique MicroRNA Molecular Profiles in Lung Cancer Diagnosis and Prognosis," *Cancer Cell* 9(3):189-198 (2006).

Yao, T.-P., et al., "Gene Dosage-Dependent Embryonic Development and Proliferation Defects in Mice Lacking the Transcriptional Integrator p300," *Cell* 93:361-372 (1998).

Yeh, M.W., et al., "False-Negative Fine-Needle Aspiration Cytology Results Delay Treatment and Adversely Affect Outcome in Patients with Thyroid Carcinoma," *Thyroid* 14(3):207-215 (2004).

Yu, C., et al., "Functional Haplotypes in the Promoter of Matrix Metalloproteinase-2 Predict Risk of the Occurrence and Metastasis of Esophageal Cancer," *Cancer Research* 64:7622-7628 (2004).

Zeng, Y., et al., "MicroRNAs and Small Interfering RNAs can Inhibit mRNA Expression by Similar Mechanisms," *PNAS* 100(17):9779-9784 (2003).

Zhang, L., et al, "Association of the Phosphatase and Tensin Homolog Gene (PTEN) with Smoking Initiation and Nicotine Dependence," *American Journal of Medical Genetics Part B (Neurophychiatric Genetics)* 141B:10-14 (2006).

Zhou, X.-P., et al., "Association of Germline Mutation in the *PTEN* Tumour Suppressor Gene and Proteus and Proteus-like Syndromes," *The Lancet* 358:210-211 (2001).

Zhou, X.-P., et al., "Germline *PTEN* Promoter Mutations and Deletions in Cowden/Bannayan-Riley-Ruvalcaba Syndrome Result in Aberrant PTEN Protein and Dysregulation of the Phosphoinositol-3-Kinase/Akt Pathway," *Am. J. Hum. Gener.* 73:404-411 (2003).

Zundel, W., et al., "Loss of *PTEN* Facilitates HIF-1-Mediated Gene Expression," *Genes & Development* 14:391-396 (2000).

Jiang, J., et al., "Real-time Expression Profiling of microRNA Precursors in Human Cancer Cell Lines", *Nucleic Acids Res.,* 33(17):5394-5403 (2005).

Eng, C., "*PTEN*: One Gene, Many Syndromes," *Human Mutation*, 22:183-198 (2003).

Nelen, M.R., et al., "Localization of the Gene for Cowden Disease to Chromosome 10q22-23," *Nature Genetics*, 13:114-116 (May 1996).

Stambolic, V., et al., "Negative Regulation of PKB/Akt-Dependent Cell Survival by the Tumor Suppressor PTEN," *Cell*, 95:29-39 (Oct. 2, 1998).

Non-published U.S. Appl. No. 12/462,053, filed Jul. 27, 2009.

Date of Mailing Feb. 7, 2008, Notice of Transmittal of the International Search Report and the Written Opinion of the International Searching Authority, or the Declaration, Application No. PCT/US2007/015265.

Date of Mailing Jan. 15, 2009, Notification Concerning Transmittal of International Preliminary Report on Patentability (Chapter 1 of the Patent Cooperation Treaty), PCT/US2007/015265.

Bayley, J.P., "Succinate Dehydrogenase Gene Variants and Their Role in Cowden Syndrome," *The American Journal of Human Genetics*, 88: 674-675 (2011).

Halushka, M.K., et al., "Patterns of Single-Nucleotide Polymorphisms in Candidate Genes for Blood-Pressure Homeostasis," *Nature Genetics*, 22: 239-247 (1999).

Hirschorn, J.N., et al., "A Comprehensive Review of Genetic Association Studies," *Genetics in Medicine*, 4(2): 45-61 (2002).

Lucentini, J., "Gene Association Studies Typically Wrong," *The Scientist*, 18: 20 (2004).

Ni, Y. and Eng, C., "Response to Bayley: Functional Study Informs Bioinformatic Analysis," *The American Journal of Human Genetics*, 88: 674-676 (2011).

Pepe, M. S., et al., "Limitations of the Odds Ratio in Gauging the Performance of a Diagnostic, Prognostic, or Screening Marker," *American Journal of Epidemiology*, 159: 882-890 (2004).

Wacholder, S., et al., "Assessing the Probability That a Positive Report Is False: An Approach for Molecular Epidemiology Studies," *Journal of the National Cancer Institute*, 96(6): 434-442 (2004).

Feb. 24, 2011, Restriction Requirement, U.S. Appl. No. 12/462,053.

Mar. 3, 2011, Restriction Requirement, U.S. Appl. No. 12/633,539.

Aug. 24, 2011, Reply to Restriction Requirement, U.S. Appl. No. 12/462,053.

Sep. 1, 2011, Reply to Restriction Requirement, U.S. Appl. No. 12/633,539.

Oct. 18, 2011, Office Action, U.S. Appl. No. 12/462,053.

Oct. 28, 2011, Office Action, U.S. Appl. No. 12/633,539.

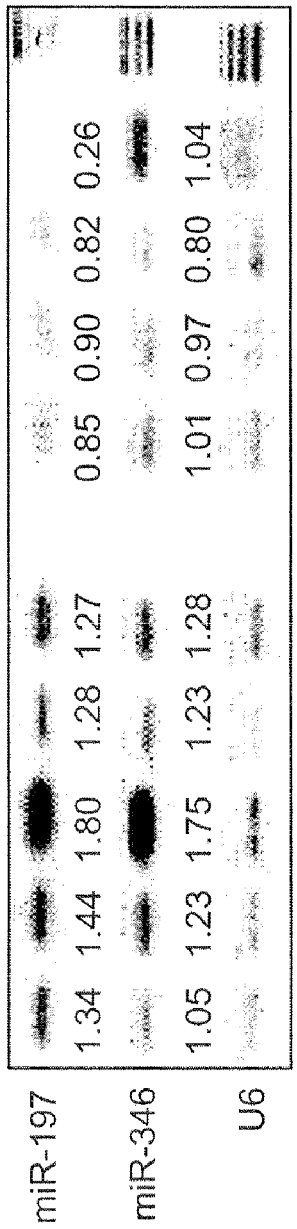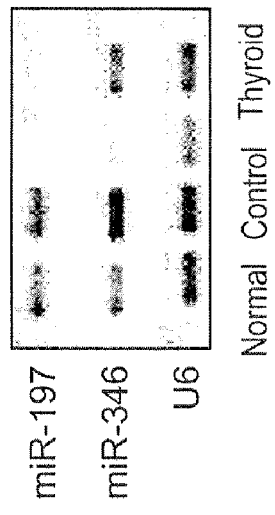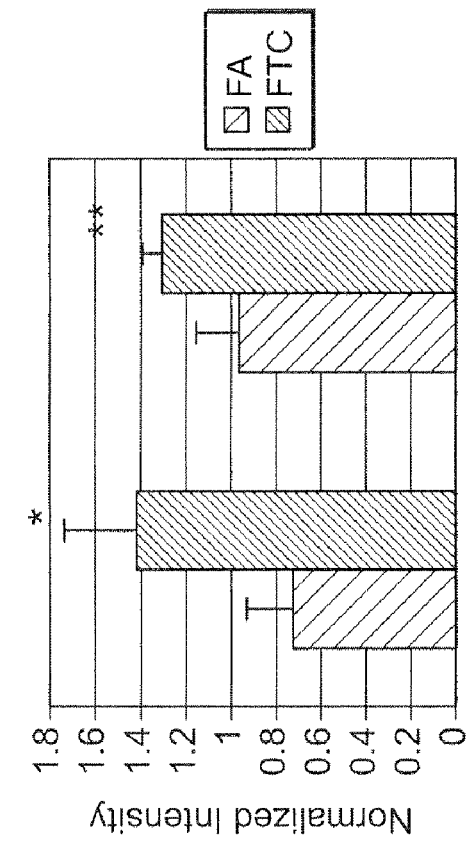
FIG. 1A
FIG. 1C
FIG. 1B

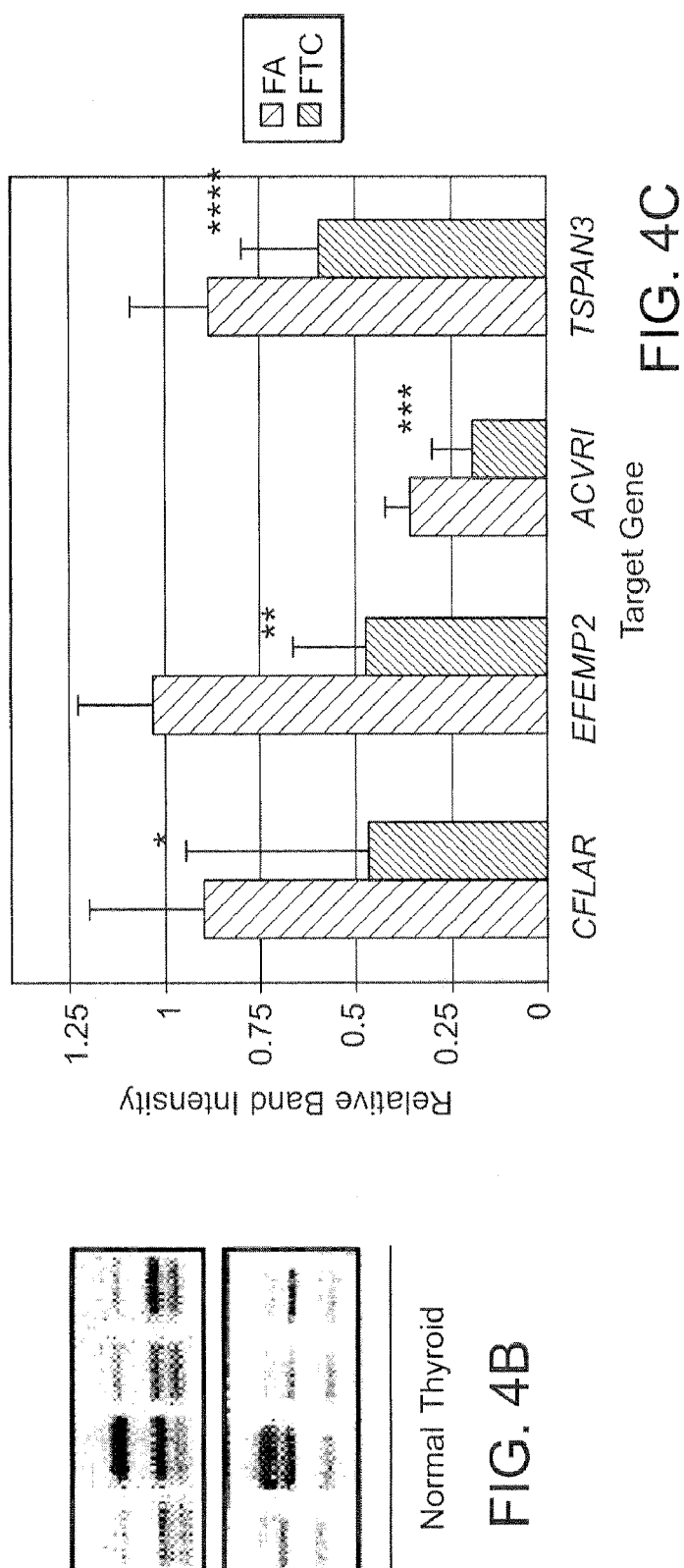
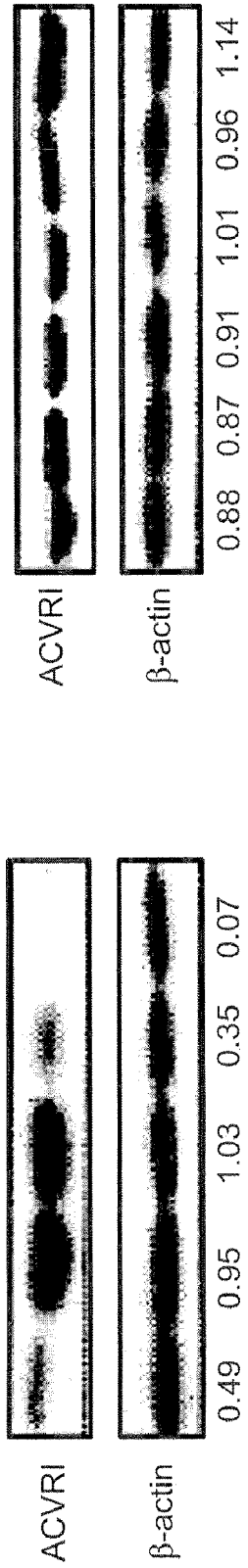
FIG. 4B
FIG. 4C
FIG. 4D
FIG. 4E

The stem-loop sequences (premiR sequences) are as follows:

Homosapian (has)-mir-192 MI0000234
GCCGAGACCGAGUGCACAGGGCUCUGACCUAUGAAUUGACAGCCAGUGCU
CUCGUCUCCCUCUGGCUGCCAAUUCCAUAGGUCACAGGUAUGUUCGCCUC
AAUGCCAGC (SEQ ID NO. 11)

hsa-mir-197 MI0000239
GGCUGUGCCGGGUAGAGAGGGCAGUGGGAGGUAAGAGCUCUUCACCCUUC
ACCACCUUCUCCACCCAGCAUGGCC (SEQ ID NO. 12)

hsa-mir-328 MI0000804
UGGAGUGGGGGGGCAGGAGGGGCUCAGGGAGAAAGUGCAUACAGCCCCUG
GCCCUCUCUGCCCUUCCGUCCCUG (SEQ ID NO. 13)

hsa-mir-346 MI0000826
GGUCUCUGUGUUGGGCGUCUGUCUGCCCGCAUGCCUGCCUCUCUGUUGCUC
UGAAGGAGGCAGGGGCUGGGCCUGCAGCUGCCUGGGCAGAGCGG (SEQ ID
NO. 14)

The mature miR sequences are as follows:

hsa-miR-192 (Chr. 11q13.1)
cugaccuaugaauugacagcc (SEQ ID NO. 15)

hsa-miR-197 (Chr. 1p13.3)
uucaccaccuucuccacccagc (SEQ ID NO. 16)

hsa-mir-346
ugucugcccgcaugccugccucu (Chr. 10q23.2) (SEQ ID NO. 17)

hsa-mir-328
cuggcccucucugcccuuccgu (Chr. 16q22.1) (SEQ ID NO. 18)

FIG. 6

Epithelium
Before LCM
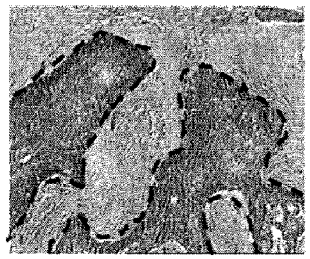
Epithelium
After LCM
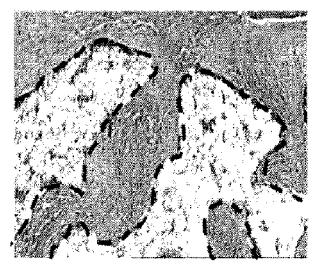
FIG. 11A
Stroma
Before LCM
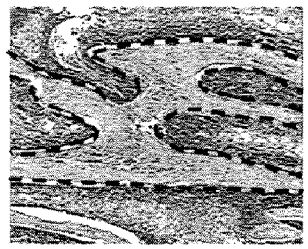
Stroma
After LCM
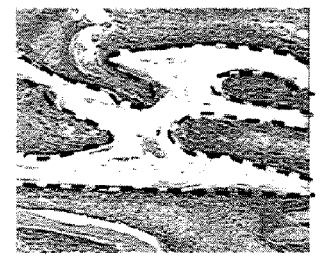
FIG. 11B

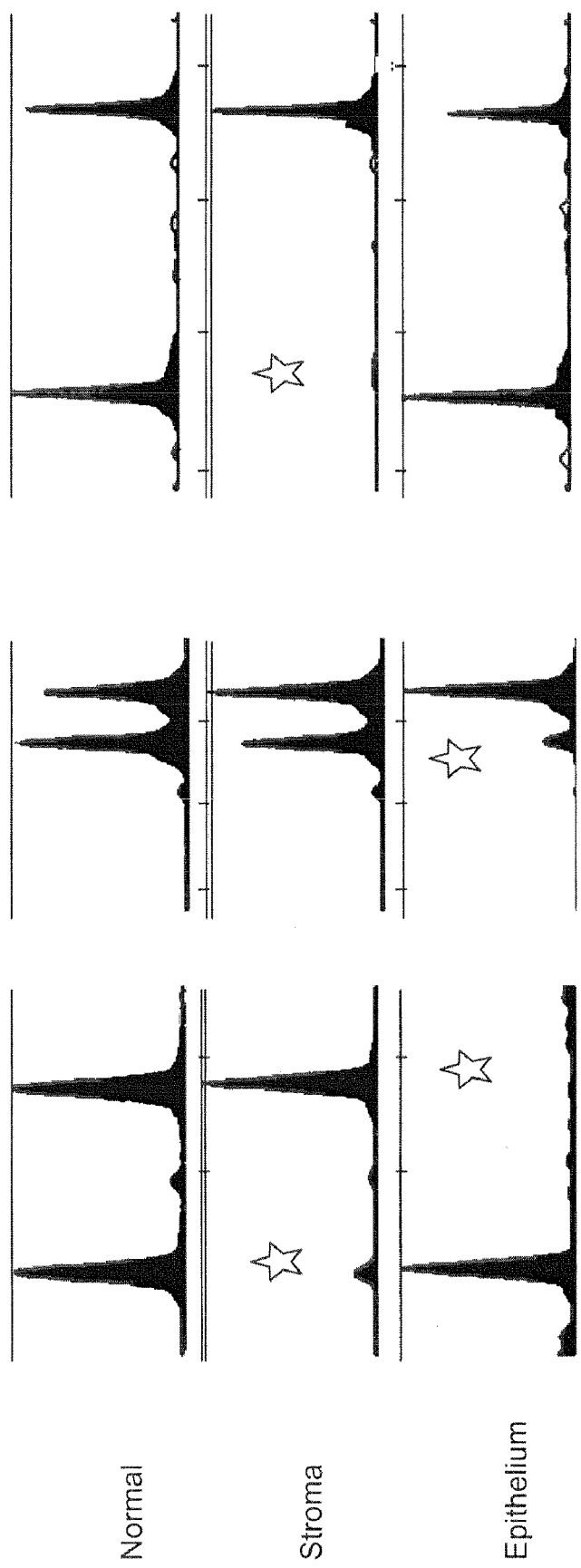

US 8,163,493 B2

TARGETS FOR USE IN DIAGNOSIS, PROGNOSIS AND THERAPY OF CANCER

RELATED APPLICATIONS

This application is a continuation of International Application No. PCT/US2007/015265, which designated the United States and was filed on Jun. 28, 2007, published in English, which claims the benefit of U.S. Provisional Application No. 60/817,249, filed on Jun. 28, 2006, U.S. Provisional Application No. 60/843,271, filed on Sep. 8, 2006, U.S. Provisional Application No. 60/874,409 filed on Dec. 12, 2006 and U.S. Provisional Application No. 60/928,796 filed on May 11, 2007. The entire teachings of the above applications are incorporated herein by reference.

GOVERNMENT SUPPORT

The invention was supported, in whole or in part, by a grants P01CA97189-01A2 and P50CA113001-01 from the National Cancer Institute, Bethesda, Md. The Government has certain rights in the invention.

BACKGROUND OF THE INVENTION

In order to improve patient management and identify novel compartments for use in diagnosis, prognosis and therapy of cancer, it is essential to further advance our understanding of this disease at the etiologic level.

SUMMARY OF THE INVENTION

Provided herein are targets (markers) that can be used for the diagnosis, prognosis and therapy of a variety of cancers. The markers identified herein include miRNAs and their target genes for detection of follicular thyroid carcinoma (FTC); haplotype blocks for detection of PTEN Hamartoma Tumor Syndrome (PHTS), and loss of heterozygosity/alleleic imbalance (LOH/AI) for detection of head and neck squamous cell carcinoma (HNSCC) and breast cancer.

Follicular Thyroid Carcinoma

Described herein are methods of detecting follicular thyroid carcinoma in an individual. In particular embodiments, the method comprises determining expression of one or more microRNAs (e.g., miR-192, miR-197, miR-346 and a combination thereof) in the individual, compared to a control; expression of one or more target genes of the microRNAs, in the individual compared to a control; or determining a combination of expression of the microRNAs and target genes in the individual. An increased expression of the microRNA, a decreased expression of the target gene or a combination thereof, compared to a control is indicative of follicular thyroid carcinoma in the individual.

In another embodiment, the method comprises distinguishing between follicular thyroid carcinoma and follicular adenoma in an individual. In this embodiment, the method comprises determining expression of one or more microRNAs (e.g., miR-192, miR-197, miR-346 and a combination thereof) in the individual, compared to a control; expression of one or more target genes of the microRNAs in the individual compared to a control; or expression of a combination of expression of the microRNAs and target genes in the individual. An increased expression of the microRNAs, a decreased expression of the target genes or a combination thereof, compared to a control is indicative of follicular thyroid carcinoma in the individual. Alternatively, a decreased expression of the microRNAs, an increased expression of the target genes or a combination thereof compared to a control, is indicative of follicular adenoma in the individual.

Also provided herein are methods of inhibiting proliferation of a follicular thyroid carcinoma cell. The method comprises introducing into the cell one or more agents which inhibit expression or activity of one or more microRNAs selected from the group consisting of: miR-192, miR-197, miR-346 and a combination thereof; introducing into the cell one or more agents which enhances expression of one or more target genes of a microRNA selected from the group consisting of: miR-192, miR-197, miR-346 and a combination thereof; or introducing into the cell a combination of the one or more agents. The cells are maintained under conditions in which the one or more agents inhibits expression or activity of the microRNAs, enhances expression of one or more target genes of the microRNAs, or results in a combination thereof, thereby inhibiting proliferation of the follicular thyroid carcinoma cell.

Methods of identifying an agent that can be used to inhibit proliferation of a follicular thyroid carcinoma cell are also provided. The method comprises contacting one or more microRNAs selected from the group consisting of: miR-192, miR-197, miR-346 with an agent to be assessed; contacting one or more target genes of one or more microRNAs selected from the group consisting of: miR-192, miR-197, miR-346 with an agent to be assessed; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

Also provided herein are methods of identifying an agent that can be used to treat a follicular thyroid carcinoma. The method comprises contacting one or more microRNAs selected from the group consisting of: miR-192, miR-197, miR-346 with an agent to be assessed; contacting one or more target genes of one or more microRNAs selected from the group consisting of: miR-192, miR-197, miR-346 with an agent to be assessed; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

The invention is also directed to kits for detecting follicular thyroid carcinoma in an individual comprising one or more reagents for detecting one or more microRNAs selected from the group consisting of: miR-192, miR-197, miR-346 in the individual, compared to a control; one or more target genes of one or more microRNAs selected from the group consisting of: miR-192, miR 97, miR-346, in the individual compared to a control; or a combination thereof.

PTEN Hamartoma Tumor Syndrome (PHTS)

PTEN Hamartoma Tumor Syndrome (PHTS) is a heritable cancer syndrome and includes Cowden Syndrome, Bannayan-Riley-Ruvalcaba Syndrome, *Proteus* Syndrome, *Proteus*-Like Syndrome. Described herein is a method of diagnosing PHTS or susceptibility to PHTS in an individual comprising detecting the presence of at least one haplotype block at the individual's PTEN locus, wherein the haplotype block is selected from the group consisting of a block 1 haplotype, a block 2 haplotype, a block 3 haplotype and a combination thereof (e.g., extended haplotypes). The presence of one or more of the haplotype blocks is indicative of a diagnosis of PHTS or a susceptibility to PHTS in the individual. Block 1 haplotypes, block 2 haplotypes, block 3 haplotypes and combinations thereof are provided herein, for example, in Tables 9 and 10. In the methods of the present invention, the individual can be PTEN mutation negative, PTEN mutation positive or PTEN variation positive.

The present invention is also directed to a method of diagnosing PHTS or susceptibility to PHTS in an individual that is PTEN mutation negative comprising detecting the presence of at least one haplotype block in the PTEN gene spanning a region upstream of the PTEN gene and the first intron of the PTEN gene. In a particular embodiment, the haplotype block in the PTEN gene spans about 33 kb from about position 89,583,605 to about position 89,616,359 of the genome (e.g., on human chromosome 10).

The present invention also provides kits for use in diagnosing PHTS or susceptibility to PHTS in an individual comprising one or more reagents for detecting one or more haplotype blocks selected from the group consisting of: a block 1 haplotype, a block 2 haplotype, a block 3 haplotype and a combination thereof.

Head and Neck Squamous Cell Carcinoma (HNSCC)

Described herein are methods of diagnosing head and neck squamous cell carcinomas (HNSCC) or susceptibility to HNSCC in an individual comprising detecting the presence of a loss of heterozygosity/allelic imbalance (LOH/AI) at one or more specific loci (markers) in the individual, wherein the presence of the LOH/AI at the one or more specific loci in the individual is indicative of a diagnosis of HNSCC in the individual. In one embodiment, the invention is directed to methods of diagnosing HNSCC or susceptibility to HNSCC in an individual comprising detecting the presence of a LOH/AI at one or more loci selected from the group consisting of: D3S3630; D4S2417; D6S305; D18S843; D19S559, in the individual, wherein the presence of the LOH/AI at the one or more loci in the individual is indicative of a diagnosis of HNSCC in the individual. In one embodiment, the one or more of the loci are present in stromal cells (e.g., non-malignant stromal cells, malignant stromal cells) surrounding the tumor (e.g., surrounding tumor epithelial cells), tumor epithelial cells or a combination thereof.

The methods of the present invention can further comprise determining tumoral attributes, such as aggressiveness of a tumor or disease, extent of HNSCC tumor invasion (e.g., tumor size (pT status), regional lymph node status (pN; lymph node involvement; lymph node metastasis)), of an HNSCC tumor present in an individual comprising detecting the presence of a LOH/AI at one or more specific loci in the genome of the individual.

In a particular embodiment, the invention is directed to a method of detecting an aggressive HNSCC tumor in an individual comprising detecting the presence of a LOH/AI at one or more specific loci in the genome of the individual, wherein the presence of the LOH/AI at the one or more specific loci in the genome of the individual is indicative of an aggressive HNSCC tumor in the individual.

Also provided herein are kits for use in diagnosing HNSCC or susceptibility to HNSCC in an individual comprising one or more reagents for detecting the presence of a LOH/AI at one or more loci selected from the group consisting of: D3S3630; D4S2417; D6S305; D18S843; D19S559.

Breast Cancer

Described herein are methods of diagnosing breast cancer or susceptibility to breast cancer in an individual comprising detecting the presence of a loss of heterozygosity/allelic imbalance (LOH/AI) at one or more specific loci (markers) in the individual, wherein the presence of the LOH/AI at the one or more specific loci in the individual is indicative of a diagnosis of breast cancer in the individual. In one embodiment, the invention is directed to methods of diagnosing breast cancer or susceptibility to breast cancer in an individual comprising detecting the presence of a LOH/AI at one or more loci selected from the group consisting of: D11S1999, D11S1986, ATA42G12, D5S1457, D5S1501, D5S816, D18S858, D20S103, D20S851, D22S683, D22S1045 in the individual, wherein the presence of the LOH/AI at the one or more of eleven specific loci in the individual is indicative of a diagnosis of breast cancer in the individual. In one embodiment, one or more of the loci are present in the stroma (e.g., non-malignant stroma) surrounding a tumor epithelium and/or epithelial cells of the tumor.

The methods of the present invention can further comprise determining breast cancer tumoral attributes, such as aggressiveness of the tumor or disease, extent of breast tumor invasion (e.g., tumor size (pT status; tumor grade), regional lymph node status (pN; lymph node involvement; lymph node metastasis)), of a breast cancer tumor present in an individual comprising detecting the presence of a LOH/AI at one or more specific loci in the genome of the individual.

In a particular embodiment, the invention is directed to a method of detecting an aggressive breast cancer tumor in an individual comprising detecting the presence of a LOH/AI at one or more specific loci in the individual, wherein the presence of the LOH/AI at the one or more specific loci in the individual is indicative of an aggressive breast cancer tumor in the individual.

Also provided herein are kits for use in diagnosing breast cancer or susceptibility to breast cancer in an individual comprising one or more regents for detecting the presence of a LOH/AI at one or more loci selected from the group consisting of: D11S1999, D11S1986, ATA42G12, D5S1457, D5S1501, D5S816, D18S858, D20S103, D20S851, D22S683, D22S1045.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C. Quantitative RT-PCR of miR-197 and miR-346 in an independent set of 5 FTC and 4 FA. (FIG. 1A) Expression levels were determined by spot densitometry and normalized to U6 small RNA controls. Normalized density values (Intensity*mm$^2$) are given below each spot. [−RT indicates no-RT negative control] (FIG. 1B) Both miRNAs were significantly over-expressed in FTC (black bars) compared to FA (grey bars) by 2-fold (*, p<0.0044) and by 1.37-fold (**, p=0.049). (FIG. 1C) Expression of miR-197 and miR-346 in 4 normal Thyroid controls similar to benign thyroid neoplasia.

(FIG. 2A) Expression levels of U6, miR-197 and miR-346 in HEK293T cells before transfection (0 hours, representing endogenous miR-197 and miR-346 levels) and at 12 and 24 hours after transfection. (FIG. 2B) Cell growth assay of transfected HEK293T cells. Y-axis represents absolute viable cell count per experiment, determined by trypan blue exclusion (n=3). * P=0.033,  P=0.049, *P=0.003 and ****P=0.012, indicating statistical significant cellular proliferation when compared to mock transfected controls at the noted time points. (FIG. 2C) Non-viable HEK293T cell count at 8, 12 and 24 hours after transfection.

(FIG. 3A) Growth arrest of FTC-133 cells is observed at significant levels after transfection with anti miR-197 (*p=0.0128), anti miR-346 (p=0.0016) and anti miR-197 together with anti miR-346 (p=0.0026) in comparison to the mock transfected control. (FIG. 3B) In K5 human FTC cells, a 3.55-fold increase () in viable cell count of the mock transfected control (grey bar) was restricted to a 1.8-fold increase (*) in the combined anti miR-197 and anti miR-346 (50 nM each) transfected cells (black bar), indicating a significant growth arrest (*p=0.00054). (FIG. 3C) No difference in numbers of non-viable cells (as determined by trypan blue stain) was observed between mock transfected control and anti miR transfected FTC-133 cells, 48 hours after transfection (p>0.2).

FIGS. 4A-4E. miR-197- and miR-346-related target gene expression in a set of 14 FTC and 9 FA. (FIG. 4A) RT-PCR analysis of CFLAR and EFEMP2 (miR-346-related target genes), ACVR1 and TSPAN3 (miR-197-related target genes). (FIG. 4B) Expression of CFLAR, EFEMP2, ACVR1 and TSPAN3 in 4 normal thyroid controls. (FIG. 4C) Relative quantitation of expression of each target gene to that of GAPDH (from A) using spot densitomery. Each bar represents the average normalized band intensity+/−SD of the respective group (FA denoted by grey bars or FTC denoted by black bars) for one target gene (ACVR1, TSPAN3, CFLAR or EFEMP2). Expression levels of each target gene was significantly lower in FTC compared to FA. *p=0.000014,  p=0.035, * p-0.00039, **** p=0.03. ACVR1 protein expression in a set of FTC (FIG. 4D) and FA (FIG. 4E) derived from the set of 23 samples used in (FIG. 4A). 2 FTC that show higher ACVR1 transcript levels also display increased protein levels, while 3 FTC with low/absent gene expression show low protein levels.

(FIG. 5A) Multiplex RT-PCR images after transfection (right panel, miR-197 transfection) are compared to corresponding mock transfection images (left panel, mock transfection). Maximum reduction in transcript levels, 2.5-fold for ACVR1 and 2.1-fold for TSPAN3 occurred at the 12-hour time point (dark gray bars). (FIG. 5B) Expression levels of miR-346 target genes CFLAR and EFEMP2 determined at 8, 12 and 24 hours after transfection with pre-miR-346. Maximum reduction in transcript levels for EFEMP2 (1.89 fold) was observed at 24 hours after transfection.

FIG. 6 shows the stem-loop sequences (premiR sequences) (SEQ ID NOs. 11-14) and the corresponding mature miR sequences (SEQ ID Nos. 15-18) for *Homosapian* (has) miR-192, miR-197, miR-328 and miR-346.

FIG. 10A) 94 control samples, FIG. 10B) 146 PTEN mutation negative samples, and FIG. 10C) 205 PTEN mutation/variation positive samples. The control samples display three distinct haplotype blocks: block 1 from SNP1 (−30602 G/T) to SNP9 (IVS1+2074insA), block 2 from SNP11 (IVS1−13820 A/G) to SNP21 (IVS5−7156 A/G), and block 3 from SNP23 (IVS6+457 A/G) to SNP30 (*30414 C/T). SNP10 (IVS1−14725delG) and SNP22 (IVS5−2459 T/C) appear to lie near/within areas of historical recombination. Both the PTEN mutation negative and the PTEN mutation/variation positive samples display varied LD patterns across this locus compared to the control population.

FIGS. 11A-11C. Laser capture microdissection (LCM) of the epithelium (FIG. 1a) and stroma (FIG. 1b) of squamous cell cancer lesions. Genotyping chromatograms illustrate that in a single sample, LOH/AI (depicted by star) can occur in discordant alleles (D7S1799) or exclusively in one compartment (D14S617 in epithelium; D9S2157 in stroma) (FIG. 1c).

FIG. 1A, an example of multiplex PCR genotyping for LOH/AI analysis with a primer panel composed of 3 microsatellite markers (D20S851, D4S3243 and D10S212) labeled with tetrachloro-6-carboxy-fluorescein (TET). By comparing the heights of the matched genotypes of normal tissue and tumor stroma or epithelium, LOH/AI was detected in stroma at D20S851 and D10S212, and in epithelium at D20S851, respectively; FIG. 1B, another example of multiplex PCR genotyping with a different primer panel composed of 4 markers (ATA5A09, D8S1179, D5S1462 and D3S1763) labeled with 6-carboxy-tetramethyl-rhodamine (FAM, in blue) or hexachloro-6-carboxyl-fluorescein (HEX, in green). In this panel, LOH/AI was detected in stroma at D5S1462 and D3S1763 while no LOH was detected in epithelium. L; loss of heterozygosity/allelic imbalance, R; retention of heterozygosity, and H; homozygosity.

DETAILED DESCRIPTION OF THE INVENTION

Figure 2A:
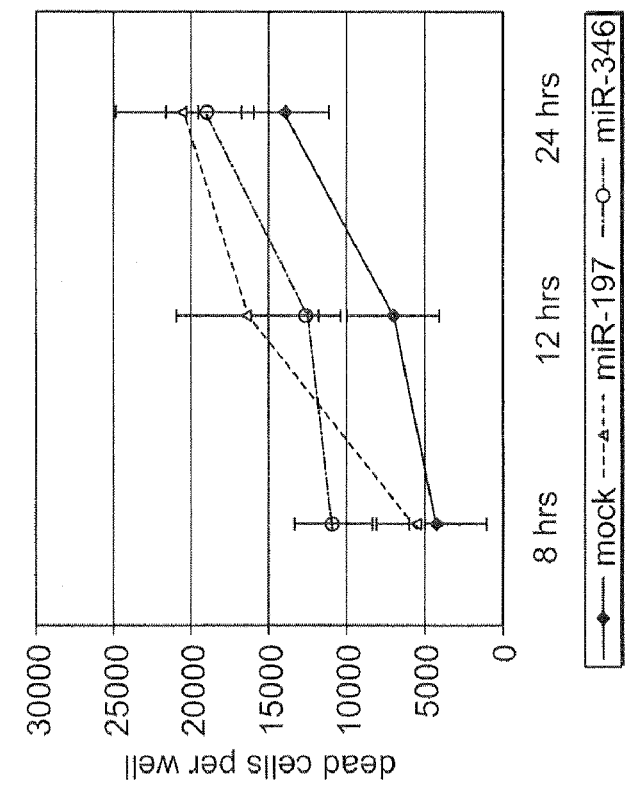
FIGS. 2A-2C. In vitro over-expression of miR-197 and miR-346 in HEK293T cells.

Provided herein are targets (markers) that can be used for the diagnosis, prognosis and therapy of a variety of cancers. The markers identified herein include miRNAs and their target genes for detection of follicular thyroid carcinoma (FTC); haplotype blocks for detection of PTEN Hamartoma Tumor Syndrome (PHTS), and loss of heterozygosity/alleleic imbalance (LOH/AI) for detection of head and neck squamous cell carcinoma (HNSCC) and breast cancer.

Follicular Thyroid Carcinoma

While the pathogenesis of follicular thyroid carcinoma (FTC) and its relation to follicular adenoma (FA) remains unclear, detailed understanding of FTC carcinogenesis would facilitate addressing the scientific and clinical challenges given that there are morphological and molecular similarities between FTC and the frequently occurring FA. Micro-RNA's (miRNA's) are a new class of small, non-coding RNA's implicated in development and cancer, and may lend novel clues to FTC genesis. For the latter process, a deregulated miRNA can orchestrate the aberrant expression of several hundred target genes. Described herein is the identification of deregulated micro-RNA's in follicular thyroid cancer.

Two high-density expression arrays were used to identify miRNA's and their target genes that are differentially expressed between FTC and FA. Validation was done by qRT-PCR. Further, the effect of deregulated miRNAs in vitro were functionally characterized using HEK293T, FTC 133 and K5 cell lines. In total, 45 primary thyroid samples (23 FTC, 20 FA, 4 normal control thyroid) were analyzed.

Two specific miRNA's, miR-197 and miR-346, were significantly over-expressed in FTC. In vitro over-expression of either miRNA induced proliferation, while inhibition led to growth arrest. Over-expression of miR-197 and miR-346 repressed the expression of their predicted target genes in vitro and in vivo.

The observations described herein show that miR-197 and miR-346 contribute to FTC carcinogenesis. Both miRNA's and their target genes provide for novel molecular markers and act as novel targets for treatment by interference, which could likely normalize the deregulated profile of many downstream target genes.

MicroRNAs (miRNAs, miRs) are a class of small, noncoding RNA transcripts that are thought to act as key regulators during differentiation and development (Alvarez-Garcia, I., et al., *Development*, 132:4653-62 (2005)). Each miRNA can influence the expression of several hundred different target genes both at the transcriptional and post-transcriptional levels (Alvarez-Garcia, I., et al., *Development*, 132:4653-62 (2005); Miska, E. A., *Curr. Opin. Genet. Dcv.*, 15:563-8 (2005); Zeng, Y., et al., *Proc. Natl. Acad. Sci. U.S.A.*, 100: 9779-84 (2003)). While the field of miRNA investigation is still young and many functional aspects need to be elucidated, the availability of high density miRNA chip profiling allowed identification of unique signatures associated with a variety of human malignancies (Lu, J., et al., *Nature*, 435:834-8 (2005); Chen, C. Z., et al., *N. Engl. J. Med.*, 353:1768-71 (2005); Iorio, M. V., et al., *Cancer Res.*, 65:7065-70 (2005); Murakami, Y., et al., *Oncogene*, 25:2537-45 (2005)). The potential utilization of miRNAs as diagnostic and/or prognostic markers has also been described (Chen, C. Z., et al., *N. Engl. J. Med.*, 353:1768-71 (2005); Iorio, M. V., et al., *Cancer Res.*, 65:7065-70 (2005); Murakami, Y., et al., *Oncogene*, 25:2537-45 (2005); Calin, G. A., et al., *N. Engl. J. Med.*, 353:1793-801 (2005)). In addition, recent findings indicate that miRNAs should also be considered as new targets for treatment of diseases (Weiler, J., et al., *Gene Ther.* 13(6):496-502 (2006)).

Thyroid cancer derived from the follicular epithelial cells account for the great majority of all thyroid malignancies. Of these, follicular thyroid carcinoma (FTC) accounts for about 10-15%. However, in iodine-deficient areas, the incidence can be twice as high (Surveillance_Research_Branch, Surveillance Epiemiology and End Results, National Cancer Institute 2005; Farahati, J., et al., *Thyroid*, 14:141-7 (2004)). In the clinical setting, FTC poses a special diagnostic challenge due to the morphological and molecular similarities to the benign follicular adenoma (FA) (Yeh, M. W., et al., *Thyroid*, 14:207-15 (2004)). Different molecular profiles have been proposed to improve preoperative diagnosis (Segev, D. L., et al., *Acta Cytol.*, 47:709-22 (2003); Cerutti, J. M., et al., *J. Clin. Invest.*, 113:1234-42 (2004); Kebebew, E., et al, *Surgery*, 138:1102-9; discussion 1109-10 (2005); Umbricht, C. B., et al., *Clin. Cancer Res.*, 10:5762-8 (2004); Weber, F., et al., *J. Clin. Endocrinol. Metab.*, 90:2512-21 (2005)). However, the accurate preoperative diagnosis of FTC, especially minimally invasive FTC, continues to be a challenge. In addition, while thyroid cancer in general has a favorable prognosis, FTC, when diagnosed at an advanced stage is incurable with 10-year survival rates below 40% (Passler, C., et al., *Endocr. Relat., Cancer*, 11:131-9 (2004)). Therefore, the challenge is not only to identify molecular markers for highly accurate diagnostic tests but also to find new targets for treatment of locally advanced or metastatic thyroid cancer.

Despite much progress over the recent years, there is a continued limited understanding of the molecular and biological relationship of the different benign thyroid neoplasias to each other and to thyroid carcinomas, in particular FTC (Segev, D. L., et al., *Surg. Oncol.*, 12:69-90 (2003); Weber, F., et al., *Future Oncology*, 1:497-510 (2005)). In contrast to papillary thyroid carcinoma (PTC), the major underlying genetic alterations leading to follicular thyroid carcinogenesis remain heterogeneous, even obscure (Segev, D. L., et al., *Surg. Oncol.*, 12:69-90 (2003); Weber, F., et al., *Future Oncology*, 1:497-510 (2005); Kimura, E. T., et al., *Cancer Res.*, 63:1454-7 (2003)).

Described herein is the investigation of whether the uniform deregulation of a specific set of miRNAs could induce down-regulation of a cascade of target tumor suppressor genes. It is likely that identifying such key molecular differences between FA, which are benign follicular neoplasias, and FTC, which are malignant follicular thyroid neoplasias, will result in discovering genes and events associated with FTC initiation. Therefore, described herein is the elucidatation of the differences in global miRNA expression between FA and FTC which resulted in the dissecting out of deregulated human miRNAs that provides much needed improvement in pre-operative diagnosis of FTC versus FA, and treatment of this cancer.

Accordingly, provided herein are methods of detecting follicular thyroid carcinoma in an individual. In one embodiment, the method comprises determining expression of one or more microRNAs (miRs) in the individual, compared to a control. Alternatively, or in addition, expression of one or more target genes of the microRNAs, in the individual compared to a control can be determined. An increased expression of the microRNA, a decreased expression of the target gene or a combination thereof, compared to a control is indicative of follicular thyroid carcinoma in the individual.

In another embodiment, the method comprises distinguishing between follicular thyroid carcinoma and follicular adenoma in an individual. In this embodiment, the method comprises determining expression of one or more microRNAs in the individual, compared to a control. Alternatively, or in addition, expression of one or more target genes of the microRNAs in the individual compared to a control can be determined. An increased expression of the microRNAs, a decreased expression of the target genes or a combination thereof, compared to a control is indicative of follicular thyroid carcinoma in the individual. Also, a decreased expression of the microRNAs, an increased expression of the target genes or a combination thereof compared to a control, is indicative of follicular adenoma in the individual.

MicroRNAs (miRNAs, miRs) are a class of small, noncoding RNA transcripts that are thought to act as key regulators during differentiation and development (Alvarez-Garcia, I., et al., *Development*, 132:4653-62 (2005)). Each miRNA can influence the expression of several hundred different target genes both at the transcriptional and post-transcriptional levels (Alvarez-Garcia, I., et al., *Development*, 132:4653-62 (2005); Miska, E. A., *Curr. Opin. Genet. Dcv.*, 15:563-8 (2005); Zeng, Y., et al., *Proc. Natl. Acad. Sci. USA.*, 100: 9779-84 (2003)).

As shown herein, examples of miRs that are overexpressed in FTC include miR-192, miR-197, miR-328 and miR-346. In a particular embodiment, expression of miR-192, miR-197 and miR-346 are detected in the methods.

Also provided herein are target genes of the miRs (e.g., see Tables 4, 5 and 6). Examples of particular target genes can be detected in the methods provided herein include ACVR1, TSPAN3, and EFEMP. In addition, the expressed products of these genes can be detected in the methods described herein.

In the methods of the invention, a sample can be obtained from the individual and used in the methods to detect the presence of miRNA and/or the expression of target genes of the miRNAs. Suitable samples include biological fluid (e.g., blood, urine, lymph), cell(s) (e.g., fetal cells), and/or tissue (e.g., skin, muscle, organ, placenta). In addition, nucleic acid and/or protein can be obtained from the individual or the sample of the individual and used in the methods described herein. Methods for obtaining a suitable sample or extracting nucleic acid or protein from such samples are described herein and known to those of skill in the art.

Methods for detecting the expression (presence, level, amount) of miRNAs or expression of a target gene of a miRNA are provided herein and other such methods are known to one of skill in the art. Examples of such methods include miRNA chip analysis and gel electrophoresis (western blot).

As described herein, expression of one or more microRNAs in the individual and/or one or more target genes of the microRNAs in the individual can be compared to a control. Suitable controls for use in the methods provided herein are apparent to those of skill in the art. For example, a suitable control can be established by assaying one or more (e.g., a large sample of) individuals which do not have follicular thyroid carcinoma. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

The methods of detecting follicular thyroid carcinoma in an individual and/or distinguishing between follicular thyroid carcinoma and follicular adenoma in an individual can be performed prior to, or after, surgical intervention (surgery).

The findings herein also provide for methods of inhibiting (partially, completely) proliferation of a (one or more) follicular thyroid carcinoma cell (e.g., in vitro, in vivo) comprising introducing into the cell one or more agents which inhibit expression or activity of one or more microRNAs selected from the group consisting of: miR-192, miR-197, miR-346 and a combination thereof. Alternatively, or in addition, one or more agents which inhibits expression of one or more target genes of a microRNA selected from the group consisting of: miR-192, miR-197, miR-346 and a combination thereof can be introduced into the cell. The cells are maintained under conditions in which the one or more agents inhibits expression or activity of the microRNAs, inhibits expression of one or more target genes of the microRNAs, or inhibits a combination thereof, thereby inhibiting proliferation of the follicular thyroid carcinoma cell.

Methods of identifying an agent that can be used to inhibit proliferation of a follicular thyroid carcinoma cell are also provided. The method comprises contacting one or more microRNAs selected from the group consisting of: miR-192, miR-197, miR-346 with an agent to be assessed; contacting one or more target genes of one or more microRNAs selected from the group consisting of: miR-192, miR-197, miR-346 with an agent to be assessed; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

Also provided herein are methods of identifying an agent that can be used to treat a follicular thyroid carcinoma. The method comprises contacting one or more microRNAs selected from the group consisting of: miR-192, miR-197, miR-346 with an agent to be assessed; contacting one or more target genes of one or more microRNAs selected from the group consisting of: miR-192, miR-197, miR-346 with an agent to be assessed; or contacting a combination thereof. If expression of the microRNAs is inhibited in the presence of the agent; of if expression of the target genes is enhanced in the presence of the agent, or a combination thereof occurs in the presence of the agent, then the agent can be used to inhibit proliferation of a follicular thyroid carcinoma cell.

Agents that can be assessed in the methods provided herein include miRNA inhibitors (Ambion; Austin, Tex.). Other examples of such agents include pharmaceutical agents, drugs, chemical compounds, ionic compounds, organic compounds, organic ligands, including cofactors, saccharides, recombinant and synthetic peptides, proteins, peptoids, nucleic acid sequences, including genes, nucleic acid products, and antibodies and antigen binding fragments thereof. Such agents can be individually screened or one or more compound(s) can be tested simultaneously in accordance with the methods herein. Large combinatorial libraries of compounds (e.g., organic compounds, recombinant or synthetic peptides, peptoids, nucleic acids) produced by combinatorial chemical synthesis or other methods can be tested (see e.g., Zuckerman, R. N. et al., J. Med. Chem., 37:2678-2685 (1994) and references cited therein; see also, Ohlmeyer, M. H. J. et al., Proc. Natl. Acad. Sci. USA, 90:10922-10926 (1993) and DeWitt, S. H. et al., Proc. Natl. Acad. Sci. USA, 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). The teachings of these references are incorporated herein by reference. Where compounds selected from a combinatorial library carry unique tags, identification of individual compounds by chromatographic methods is possible. Chemical libraries, microbial broths and phage display libraries can also be tested (screened) in accordance with the methods herein.

The miRs that are overexpressed in FTC and the target genes of these miRs (e.g., see Tables 4, 5 and 6) also provide for therapeutic targets for treating follicular thyroid carcinoma.

The invention is also directed to kits for detecting follicular thyroid carcinoma in an individual comprising one or more reagents for detecting 1) one or more microRNAs selected from the group consisting of: miR-192, miR-197, miR-346 in the individual; 2) one or more target genes of one or more microRNAs selected from the group consisting of: miR-192, miR-197, miR-346; 3) one or more polypeptides expressed by the target genes or 4) a combination thereof. For example, the kit can comprise hybridization probes, restriction enzymes (e.g., for RFLP analysis), allele-specific oligonucleotides, and antibodies that bind to the polypeptide expressed by the target gene. In a particular embodiment, the kit comprises at least contiguous nucleotide sequence that is substantially or completely complementary to a region one or more of the microRNAs. In one embodiment, one or reagents in the kit are labeled, and thus, the kits can further comprise agents capable of detecting the label. The kit can further comprise instructions for detecting follicular carcinoma using the components of the kit.

PTEN Harmatoma Syndrome

Phosphatase and tensin homolog deleted on chromosome ten (PTEN [MIM 601728]) encodes a tumor suppressor gene frequently mutated in both sporadic and heritable forms of human cancer. Germline mutations are associated with a number of heritable cancer syndromes referred to as the PTEN Hamartoma Tumor Syndrome (PHTS) and include Cowden Syndrome (CS [MIM 158350]), Bannayan-Riley-Ravalcaba Syndrome (BRRS [MIM 153480]), Proteus Syndrome (PS [MIM 176920]), and Proteus-like Syndrome (PLS). Germline PTEN mutations have been identified in a significant proportion of patients with PHTS, however, there are still many individuals with classic diagnostic features for whom mutations have yet to be identified. To address this, a haplotype-based approach was taken and the association of specific genomic regions of the PTEN locus with PHTS was investigated. This locus was found to be characterized by three distinct haplotype blocks of length 33 kb, 65 kb, and 43 kb, respectively. Comparisons of the haplotype distributions for all three blocks differed significantly among PHTS patients and controls (P-value=0.0098, <0.0001, and <0.0001, respectively). 'Rare' haplotype blocks and extended haplotypes account for 2- to 3-fold more PHTS chromosomes compared to control chromosomes. PTEN mutation negative patients are strongly associated with a haplotype block spanning a region upstream of PTEN and the gene's first intron (P-value=0.0027). Furthermore, allelic combinations contribute to the phenotypic complexity of this syndrome. Taken together, these data indicate that specific haplotypes and rare alleles underlie the disease etiology in these sample populations, constitute low-penetrant, modifying loci, and, specifically in the case of PHTS patients where traditional mutations have yet to be identified, likely harbor pathogenic variant(s) which have escaped detection by standard PTEN mutation scanning methodologies.

Phosphatase and tensin homolog deleted on chromosome ten (PTEN [MIM 601728]) (also known as mutated in multiple advanced cancers 1 (MMAC1) and tensin-like phosphatase 1 (TEP1)) encodes a tumor suppressor phosphatase that signals down the phosphoinositol-3-kinase (PI3K)/AKT pathway, effecting apoptosis and cell cycle arrest (Eng, C., Hum. Mutat., 22:183-198 (2003); Maehama, T., et al. J. Biol. Chem., 273:13375-13378 (1998); Stambolic V, et al., Cell, 95:29-39 (1998)). Germline PTEN mutations are primarily associated with a number of apparently clinically distinct heritable cancer syndromes jointly referred to as the PTEN Hamartoma Tumor Syndrome (PHTS) (Marsh, D. J., et al., Hum. Mol. Genet., 8:1461-1472 (1999). These include Cowden Syndrome (CS [MIM 158350]), Bannayan-Riley-Ravalcaba Syndrome (ERRS [MIM 153480]), Proteus Syndrome (PS [MIM 176920]), and Proteus-like Syndrome (PLS). All four syndromes are characterized by multiple hamartomatous lesions affecting derivatives of all three germ cell layers. In CS, patients are also at an increased risk of developing breast, thyroid, and endometrial cancer (Eng, C., J. Med. Genet., 37:828-830 (2000); Pilarski, R., et al., J. Med. Genet, 41:323-326 (2004)). To date, germline PTEN mutations have been identified in 85% of patients diagnosed with CS and 65% of patients diagnosed with BRRS (Marsh, D. J., et al., Hum. Mol. Genet., 8:1461-1472 (1999); Zhou, X. P., et al., Am. J. Hum. Genet., 73:404-411 (2003)). Additionally, 20% and 50% of patients with PS and PLS, respectively, have also been shown to carry PTEN germline mutations (Smith, J. M., et al., J. Med. Genet., 39:937-940 (2002); Zhou, X., et al., Lancet, 358:210-211 (2001); Loffeld, A., et al., Br. J. Dermatol., 154:1194-1198 (2006)).

Mutation scanning of PTEN has primarily focused on the gene's nine exons and intron/exon boundaries, which span approximately 103 kilo-basepair (kb) on chromosome subband 10q23.3. Germline mutations have been reported throughout PTEN, with the exception of exon 9, and the majority of these localize to its phosphatase catalytic core located in exon 5 (Eng, C., Hum. Mutat., 22:183-198 (2003); Bonneau, D. et al., Hum. Mutat., 16:109-122 (2000)). More recently, mutations in PTEN's core promoter region have also been identified and found to be associated with CS and increased phosphorylated AKT levels (Zhou, X. P., et al., Am. J. Hum. Genet., 73:404-411 (2003)). However, despite the significant proportion of patients with known PTEN mutations, there are still many individuals with classic PHTS diagnostic features for whom mutations have yet to be identified. Notably, CS is believed to be linked to the PTEN region, without genetic heterogeneity (Nelen, M. R., et al., Nat. Genet., 13:114-116 (1996)). In BRRS, on the other hand, the extent of genetic heterogeneity is unknown. Other mechanisms, such as modifiers of PTEN or another gene (or genes), which have yet to be identified, may be causal of this syndrome (Marsh, D. J., et al., Hum. Mol. Genet., 8:1461-1472 (1999); Carethers, J. M., et al., Cancer Res., 58:2724-2726 (1998)). For individuals with PHTS, particularly those with CS, and without identifiable germline mutations, therefore, it is likely that the molecular mechanism(s) underlying their disease involves genetic alteration outside of the PTEN coding sequence, possibly involving elements associated in its trans-regulation, or deregulation, and which may lie upstream, downstream, or intronic of PTEN. Identifying the mechanism of PTEN dysfunction in these patients is critical and of significant importance to the practice of personalized genetic healthcare.

As described herein, to aid in identifying these genetic alterations, a haplotype-based approach was used to investigate the association of specific genomic regions of the PTEN locus with disease. Through this approach, it is demonstrated herein that specific haplotypes, perhaps acting as low-penetrance susceptibility loci, are associated with PHTS in PTEN mutation negative samples. In addition to furthering the understanding of the role PTEN has in patients without detectable mutations, specific haplotypes which may act as low-penetrance alleles, or modifying factors, which could influence phenotypic expression in a subset of CR/BRRS patients with known germline PTEN mutations, have also been identified.

Accordingly, the invention provides a method of diagnosing PHTS or susceptibility to PHTS in an individual comprising detecting the presence of at least one haplotype block at the individual's PTEN locus (e.g., human chromosome 10).

The PHTS includes, for example, Cowden Syndrome, Bannayan-Riley-Ruvalcaba Syndrome, *Proteus* Syndrome, *Proteus*-Like Syndrome and a combination thereof. In addition, in the methods of the invention, the individual can be PTEN mutation negative, PTEN mutation positive or PTEN variation positive.

A haplotype refers to a segment of DNA (e.g., genomic DNA) that is characterized by a specific combination of genetic markers (alleles) arranged along the segment (typically along the same chromosome). A marker refers to a sequence (e.g., genomic sequence) characteristic of a particular allele (e.g., variant allele). The marker can comprise any allele such as SNPs, microsatellites, insertions, deletions, substitutions, duplications and translocations. Typically, a haplotype block refers to a chromosome region of high linkage disequilibrium and low haplotype diversity, and are regions of low recombination flanked by recombination hotspots (e.g., Cardon, L R and Abecasis, G R, *Trends in Genetics*, 19(3):135-140 (2003)).

In particular embodiments, the haplotype block is selected from the group consisting of a block 1 haplotype, a block 2 haplotype, a block 3 haplotype and a combination thereof (e.g., extended haplotypes). The presence of one or more of the haplotype blocks is indicative of a diagnosis of PHTS or a susceptibility to PHTS in the individual. Block 1 haplotypes, block 2 haplotypes, block 3 haplotypes and combinations thereof (e.g., extended haplotypes) are provided in Tables 9 and 10 herein. In the methods of the present invention, the individual can be PTEN mutation negative, PTEN mutation positive or PTEN variation positive. In a particular embodiment, the individual is PTEN mutation positive or PTEN variation positive and the haplotype block 1 comprises the sequence GACCCTCGI (SEQ ID NO: 19).

Examples of methods for detecting the haplotype blocks are described herein and other suitable methods are well known to those of skill in the art. Suitable methods for detecting haplotypes in a sample include sequence analysis, hybridization analysis using a nucleic acid probe such DNA or RNA (e.g., Northern analysis, Southern analysis, dot blot analysis), and restriction digestion.

In the methods of the invention, a sample can be obtained from the individual and used in the methods to detect the presence of the haplotype blocks. The haplotype block can be detected in any sample obtained from the individual that comprises the individual's DNA (e.g., genomic DNA). For example, a haplotype block can be detected in a tissue sample (e.g., skin, muscle, organ, placenta), a cell sample (e.g., fetal cells), a fluid sample (e.g., blood, amniotic fluid, cerebrospinal fluid, urine, lymph) and any combination thereof. Methods of obtaining such samples a or extracting nucleic acid from such samples are described herein and known to those of skill in the art.

The detection of the haplotype block in the individual can be compared to a control. Suitable controls for use in the methods provided herein are apparent to those of skill in the art. For example, a suitable control can be established by assaying one or more (e.g., a large sample of) individuals which do not have PTEN Hamartoma Tumor Syndrome. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

The present invention is also directed to a method of diagnosing PHTS or susceptibility to PHTS in an individual that is PTEN mutation negative comprising detecting the presence of at least one haplotype block in the PTEN gene spanning a region upstream of the PTEN gene and the first intron of the PTEN gene. In a particular embodiment, the haplotype block in the PTEN gene spans about 33 kb from about position 89,583,605 to about position 89,616,359 of the genome (e.g., on human chromosome 10).

The haplotype blocks (e.g., see Tables 9 and 10) identified herein also provide for therapeutic targets for treating PTEN Hamartoma Tumor Syndrome.

The invention is also directed to kits diagnosing PHTS or susceptibility to PHTS in an individual comprising one or more reagents for detecting one or more haplotype blocks selected from the group consisting of: a block 1 haplotype, a block 2 haplotype, a block 3 haplotype and a combination thereof. For example, the kit can comprise hybridization probes, restriction enzymes (e.g., for RFLP analysis), allele-specific oligonucleotides, and antibodies. In a particular embodiment, the kit comprises at least contiguous nucleotide sequence that is substantially or completely complementary to a region of one or more of the haplotype blocks or combinations of haplotype blocks (e.g., a block 1 haplotype, a block 2 haplotype, a block 3 haplotype, extended haplotype block and a combination thereof). For example, the nucleic acids can comprise at least one sequence (contiguous sequence) which is complementary (completely, partially) to one or more haplotypes associated with PHTS. In one embodiment, the one or more reagents in the kit are labeled, and thus, the kits can further comprise agents capable of detecting the label. The kit can further comprise instructions for detecting PHTS using the components of the kit.

Head and Neck Squamous Cell Carcinoma (HNSCC)

Carcinogens associated with HNSCC genesis should inflict genomic alterations not only on the epithelium but also the mesenchyme of the aero-digestive tract. Therefore, the apparently non-malignant stroma surrounding the tumor epithelium can acquire genomic alterations and contribute to cancer initiation and progression.

Described herein is the determination of compartment-specific loci of loss-of-heterozygosity/allelic imbalance (LOH/AI) and identification of which genomic alterations restricted to the stroma cell population contributes to aggressiveness of HNSCC disease.

Tumor epithelium and surrounding stroma were isolated from 122 patients with oral cavity and oro/hypopharyngeal SCC and subjected to whole genome LOH/AI analysis using 366 microsatellite markers.

Compartment-specific frequency and distribution of LOH/AI were determined and hot-spots of genomic alterations identified. Compartment-specific LOH/AI events were correlated with presenting clinico-pathologic characteristics.

Tumor-associated stroma of HNSCC from smokers were found to have a high degree of genomic alterations. A clear correlation between tumor aggressiveness could be found for a specific set of 5 loci. Three stroma-specific loci were associated with tumor size (pT) and regional nodal metastasizes (pN). Further, 2 epithelial-specific LOH/AI hot-spots were positively correlated with pN status and clinical stage.

Stroma-specific genetic alterations likely to play a role in smoking-related HNSCC genesis. The findings described herein provide not only novel prognostic or diagnostic biomarkers, but more importantly identify new molecular targets for therapeutic and potentially preventive intervention. Despite its slowly declining incidence rate (~4% since 1980) and a modest improvement in 5 year survival (54.4% to 59.4% over the last 20 years), squamous cell carcinoma of the head and neck (HNSCC) continues to be a clinical challenge (Forastiere, A., et al., *N. Engl. J. Med.;* 345:1890-1900 (2001); Ries, LAG H D, et al., Cancer Statistics Review, 1975-2003: National Cancer Institute (2006)). With a worldwide prevalence of over 1.6 million, it is estimated that in 2006, about 30,990 new cases will be diagnosed in the United States alone (Ries, LAG H D, et al., Cancer Statistics Review, 1975-2003; National Cancer Institute (2006); American Cancer Society, Oral cancer facts and figures, Atlanta 2006)). Even with the utilization of all modern therapeutic options that include surgery, radiation therapy and chemotherapeutic intervention, 50% of all patients will ultimately die of this disease, with over 7400 this year in the US alone (Ries, LAG. H D, et al., Cancer Statistics Review, 1975-2003: National Cancer Institute (2006); American Cancer Society, Oral cancer facts and figures, Atlanta 2006)). Especially for patients diagnosed with advanced or relapsed disease, HNSCC is almost uniformly fatal (Ries, LAG H D, et al., Cancer Statistics Review, 1975-2003: National Cancer Institute (2006)).

In order to improve patient management and identify novel compartments to target therapy, it is essential to further advance our understanding of this disease at the etiologic level. It is an accepted concept that HNSCC arises from a successive accumulation of genetic alterations in the squamous epithelium of the mucosa that will allow one cell to obtain a growth advantage, escape apoptotic signaling, clonally expand and ultimately invade and metastasize (Forastiere, A., et al., *N Engl. J. Med.;* 345:1890-1900 (2001); Perez-Ordonez, B., et al., *J Clin Pathol.,* 59:445-53 (2006); Williams, H. K., *Mol Pathol.,* 53(4):165-72 (2000); Hunter, K. D., et al., *Nat Rev Cancer,* 5:127-35 (2005)). Several groups have looked at those genetic alterations and identified mutations in key regulatory genes including TP53 and p16$^{INK4a}$ as well as genetic instability in regions such as 3p, 9p, 11q and 17p (Forastiere, A., et al., *N Engl. J. Med.;* 345:1890-1900 (2001); Perez-Ordonez, B., et al., *J Clin Pathol.,* 59:445-53 (2006); Hunter, K. D., et al., *Nat Rev Cancer,* 5:127-35 (2005); Leng, K., et al., J Oral Pathol Med., 35:19-24 (2006); Worsham, M. J., et al., *Arch. Otolaryngol. Head Neck Surg.,* 132:409-15 (2006)).

Aggravating the clinical situation is the high rate of recurrent and multifocal disease in HNSCC (Forastiere, A., et al., *N Engl. J. Med.;* 345:1890-1900 (2001)). This clinical and pathological observation was first addressed by Slaugher et al. and the concept of field cancerization was coined (Slaughter, D. P., et al. Cancer, 6: 963-8 (1953)). Over the years, it has been related to genetic observations and interpreted in different ways. The hypotheses include the following: that tumor or their progenitor cells migrate (both intraepithelial or luminal) to the secondary tumor sites, or that tumors occur as independent events within genetically altered and expanding fields of pre-neoplastic epithelial cells (Braakhuis, B. J., et al., *Cancer Res.,* 63:1727-30 (2003); (Jang, S. J., et al., Oncogene, 20:2235-42 (2001); van Oijen, M. G., et al., *Cancer Epidemiol Biomarkers Prevent,* 9:249-56 (2000); Braakhuis, B. J., et al., *Semin Cancer Biol.,* 15:113-20 (2005)). However, today, it is known that cancer is not only a disease of the transformed epithelium but is fundamentally influenced by and dependent on its microenvironment including the stroma in which it develops (Mueller, M. M., *Nat. Rev. Cancer,* 4:839-49 (2004); McCawley, L. J., et al., *Curr. Biol.,* 11:R25-7 (2001)). The tumor stroma consists of fibroblasts, micro-vessels and lymphatic cells and facilitates a physical and biochemical network that communicates closely with the epithelial cells. Genetic alterations in the stromal cells can lead to aberrant excretion of proteins and misinterpretation of incoming signals resulting in disruption of the physiologic interplay between epithelium and stroma (Mueller, M. M., *Nat. Rev. Cancer,* 4:839-49 (2004); Edlund, M., et al., *J. Cell Biochem.,* 91:686-705 (2004); Weber, F., et al., *Br. J. Cancer,* 92 (10): 1922-6 (2005)). It has been shown that indeed the stromal fibroblasts of different neoplasias are rich in genetic alterations and can potentially define the tumor phenotype or potentially induce or sustain the transformation of the pre-neoplastic epithelium in sporadic and BRCA1/2-related breast cancers, prostate and pancreatic cancers, and other solid tumors (McCawley, L. J., et al., *Curr. Biol.,* 11:R25-7 (2001); Kurose, K., et al., *Hum. Mol. Genet.,* 10(18):1907-13 (2001); Weber, F., et al., *Am. J. Hum. Genet. J.,* 78(6):961-72 (2006); Hill, R., et al., *Cell.,* 123:1001-11 (2005); Condon, M. S., *Semin Cancer Biol.,* 15:132-7 (2005); Ricci, F., et al., *Cancer Biol. Ther.,* 4:302-307 (2005)). Until now, no study has looked at the tumor stroma on a comprehensive genomic level in order to address its role in HNSCC carcinogenesis (Horvath, B., et al., *Head Neck,* 27:585-596 (2005); Rosenthal, E., et al., *Mol. Carcinog.,* 40:116-121 (2004)). As described herein a whole genome approach was used, therefore, to determine the extent of genomic alterations in the stroma of HNSCC and whether it correlated with presenting clinico-pathologic features. With this study, described herein is not only the elucidation of the stromal contribution to carcinogenesis and phenotypic differentiation of the squamous cell epithelium, but ultimately the findings point to novel diagnostic and therapeutic options for new compartments.

Accordingly, the invention is directed to methods of diagnosing head and neck squamous cell carcinomas (HNSCC) or susceptibility to HNSCC in an individual comprising detecting the presence of a loss of heterozygosity/allelic imbalance (LOH/AI) at one or more specific loci (markers) in the individual, wherein the presence of the LOH/AI at the one or more specific loci in the individual is indicative of a diagnosis of HNSCC in the individual. In particular embodiments, the HNSCC is present in the oral cavity and/or in the pharynx (oro/hypopharygneal) of the individual.

Heterozygosity denotes the presence of two alleles which can be individually discriminated by slight, minor differences in DNA sequence commonly found at microsatellites, which are segments of DNA composed of variable numbers of short repeat units that occur in predictable locations within the genome but vary in absolute length according of the number of repeats. Microsatellite markers can be used to evaluate the two different copies or alleles of the human genome. In the normal state, the two alleles can be distinguished from a each other and are said to exist in a state of heterozygosity. When mutations are acquired which typically involve deletion of all or part of an allele, one of the two copies is lost from the cell by deletion leading to a loss of heterozygosity.

"Loss of heterozygosity/alleleic imbalance" typically refers to the loss of a portion of a chromosome in somatic cells (e.g., a deletion, mutation, or loss of an entire chromosome (or a region of the chromosome) from the cell nucleus). Since only one of the two copies of the affected chromosomal region originally present in an individual's genome will remain in cells which have undergone LOH, all polymorphic markers within the region will appear to be homozygous; i.e., these cells will have lost heterozygosity for these markers. Comparison of marker genotypes in a population of cells that are suspected of having undergone LOH with genotypes of normal tissue from the same individual allows for the identification of LOH, and for mapping the extent of the loss.

In particular embodiments, the LOH/AI is at one or more of the following loci: D3S3630; D4S2417; D6S305; D18S843; D19S559, in the individual (Table 17).

In the methods of the invention, a sample can be obtained from the individual and used in the methods to detect the presence of the LOH/AI. The LOH/AI can be detected in any sample obtained from the individual that comprises the individual's DNA. For example, a LOH/AI can be detected in a tissue sample (e.g., skin, muscle, organ, placenta), a cell sample (e.g., fetal cells), a fluid sample (e.g., blood, amniotic fluid, cerebrospinal fluid, urine, lymph) and any combination thereof. Methods of obtaining such samples a or extracting nucleic acid from such samples are described herein and known to those of skill in the art.

Methods of obtaining such samples are well known in the art. In a particular embodiment, the presence of a LOH/AI at one or more specific loci can be detected in a sample (e.g., tissue, cell, fluid) from the tumor epithelium and/or the surrounding stroma of the tumor epithelium in the individual. The tumor epithelium and/or surrounding stroma can be obtained using any suitable method known in the art such as laser capture microdissection (LCM). In addition, the DNA can be extracted and amplified, and the LOH/AI at one or more specific loci can be detected, using any suitable methods known in the art, as described herein. As will be apparent to one of skill in the art, methods other than those described herein can be used.

In particular embodiments, the presence of LOH/AI at one or more of the loci present in stromal cells (e.g., non-malignant stromal cells, malignant stromal cells) surrounding the tumor are detected. The stromal cells can be, for example, fibroblast cells present in the stroma. In another embodiment, the presence of LOH/AI at one or more of the loci present in epithelial cells of the tumor (epithelial tumor cells) are detected.

The detection of the LOH/AI in the individual can be compared to a control. Suitable controls for use in the methods provided herein are apparent to those of skill in the art. For example, a suitable control can be established by assaying one or more (e.g., a large sample of) individuals which do not have the LOH/AI at the loci described herein. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

The methods of the present invention can further comprise determining tumoral attributes, such as aggressiveness of a tumor or disease, extent of HNSCC tumor invasion (e.g., tumor size (pT status), regional lymph node status (pN; lymph node involvement; lymph node metastasis)), of an HNSCC tumor present in an individual comprising detecting the presence of a LOH/AI at one or more specific loci in the genome of the individual.

In a particular embodiment, the invention is directed to a method of detecting an aggressive HNSCC tumor in an individual comprising detecting the presence of a LOH/AI at one or more specific loci in the genome of the individual, wherein the presence of the LOH/AI at the one or more specific loci in the genome of the individual is indicative of an aggressive HNSCC tumor in the individual.

The LOH/AI at the one or more specific loci in individuals with HNSCC described herein can also be used as targets for therapeutic and/or preventive intervention of HNSCC in an individual.

Also provided herein are kits for use in diagnosing HNSCC or susceptibility to HNSCC in an individual comprising one or more reagents for detecting the presence of a LOH/AI at one or more loci selected from the group consisting of: D3S3630; D4S2417; D6S305; D18S843; D19S559. For example, the kit can comprise hybridization probes, restriction enzymes (e.g., for RFLP analysis), allele-specific oligonucleotides, and antibodies. In a particular embodiment, the kit comprises at least contiguous nucleotide sequence that is substantially or completely complementary to a region of one or more of the loci comprising the LOH/AI. For example, the nucleic acids can comprise at least one sequence (contiguous sequence) which is complementary (completely, partially) to one or more loci comprising LOH/AI that is associated with HNSCC. In one embodiment, the one or more reagents in the kit are labeled, and thus, the kits can further comprise agents capable of detecting the label. The kit can further comprise instructions for detecting HNSCC using the components of the kit.

Breast Cancer

Genomic instability within 11 specific genomic regions residing on chromosomes in the tumor stroma of sporadic primary invasive breast carcinomas correlates with grade and regional lymph node metastases That genomic alterations occur in both epithelium and stroma of sporadic breast cancers has been documented by several groups. However, whether these microenvironmental alterations relate to clinico-pathologic features is unknown.

Described herein is the analysis of the relationship between stromal genomic alterations and presenting clinico-pathologic features in sporadic breast cancer.

Retrospective analysis of DNA from the epithelium and stroma of 220 primary invasive breast carcinomas for global genomic alterations manifested by loss of heterozygosity/allelic imbalance with 386 microsatellite markers. Regression models and Fisher's exact test were used to test for associations between loss of heterozygosity/allelic imbalance and clinico-pathologic features.

Association of genetic alterations, in both stroma and epithelium, with presenting clinico-pathologic features such as tumor grade, expression status of estrogen- and progesterone-receptor and human epidermal growth factor receptor 2, clinical stage and regional lymph node metastasis status.

Significant associations ($p=0.0013$) between loss of heterozygosity/allelic imbalance on chromosome 11 in stroma and tumor grade, on chromosomes 1, 2, 5, 18, 20 and 22 in stroma and regional lymph node metastasis ($P=0.0002$-$0.0016$), and on chromosome 14 in epithelium and progesterone receptor expression status ($P=0.002$) were found. Specific markers contributing to the LOH/AI on chromosome 11 in the stroma associating with tumor grade were D11S1999 ($p=0.00055$) and D11S1986 ($p=0.042$). Importantly, LOH/AI at various markers in the stroma was significantly associated with pN: ATA42G12 (chrom 1, p=0.00095), D5S1457 (p=0.00095), D5S1501 (p=0.0011), D5S816 (p=0.0008), D18S858 (p=0.0026), D20S103 (p=0.0027), D20S851 (p=0.0045), D22S683 (p=0.00033) and D22S1045 (p=0.0013).

The analysis described herein revealed more correlations with clinico-pathologic features and loss of heterozygosity/ allelic imbalance in stroma than in epithelium, indicating that stromal genomic alterations help account for clinical diversity and are useful surrogate biomarkers of prognosis and outcome.

A high degree of variability is observed in both biological behavior and clinical outcome in sporadic breast cancer, and this inter-patient diversity in breast cancer biology and behavior may confound clinical management based on "averages". Breast conserving surgery has become the standard of care for early stage breast cancer. In a recently published study, 2929 early stage breast cancer patients were examined for the relative impact of the patient, the surgeon and/or hospital factors on surgical treatment outcome variation in breast cancer patients. Gort et al found that 91.2% of the total variance was attributable to the patient level, ie, there is large inter-patient variability (Gort, M., et al., *Breast Cancer Res. Treat., Epub [PMID 17028985]* (2006)). These data suggested that inter-patient variation accounts for the high degree of clinical variability (Gort, M., et al., *Breast Cancer Res. Treat.*, Epub [PMID 17028985] (2006)). Indeed, the demand for "personalized medicine" illustrates the medical community's and public's recognition of inter-patient variability. It has been recognized for decades that identical chemotherapeutic regimens for similar stage and grade patients with, eg, breast cancer (or virtually any malignancy) respond differently (Gort, M., et al., *Breast Cancer Res. Treat., Epub [PMID 17028985]* (2006); Weigelt, B., et al., *Br. J. Cancer*, 93:924-932 (2005)). The complexities of genetic alterations in breast cancer may provide a primary basis for these consequent (ie, secondary) clinico-pathologic features (CPFs) an idea supported by prior positive correlations between certain breast cancer genotype and phenotype (Simpson, P. T., et al., *J Pathol.*, 205: 248-254 (2005)). For example, well-differentiated (grade I) breast cancers show a low number of genetic alterations with highly recurrent losses of 16q, while poorly differentiated (grade III) cancers show complex genetic changes containing DNA losses as well as DNA amplifications (Simpson, P. T., et al., *J Pathol.*, 205: 248-254 (2005)). However, many previous studies focused only on restricted regions of the genome harboring known tumor-associated genes, such as TP53, or were limited to small series of patients. High throughput genome-wide scanning for genetic alterations can now be performed on larger series of clinical samples to discover genotypic-phenotypic correlations unbiased by prior work. Moreover, virtually all previous studies exploring these somatic genotype-phenotype correlations fail to separately analyze malignant epithelium and reactive host elements. Tumor microenvironment, incorporating both invasive epithelium and reactive host elements, dynamically determines cancer behavior (Bissell, M. J., et al., *J. Cell Sci. Suppl.*, 8: 327-343 (1987); Shekhar, M. P., et al., *Cancer Res.*, 61:1320-1326 (2001)). The contribution of cancer-associated stromal cell genetic changes to this interaction have been variously ascribed to epigenetic changes (DNA methylation) (Allinen, M., et al., *Cancer Cell.*, 6: 17-32 (2004); Hu, M., et al., *Nat. Genet.*, 37: 899-905 (2005)), or mutation, as has been shown for tumor-associated stroma from breast, colon, bladder and ovarian cancers (Moinfar, F., et al., *Cancer Res.*, 60:2562-2566 (2000); Kurose, K., et al., *Hum. Mol. Genet.*, 10:1907-1913 (2001); Wernert, N., et al., *Anticancer Res.*, 21:2259-2264 (2001); Kurose, K., et al., *Nat. Genet.*, 32:355-357 (2002); Fukino, K., et al., *Cancer Res.*, 64:7231-7236 (2004); Tuhkanen, H., et al., *Int. J. Cancer*, 109:247-252 (2004)). Previous work with breast cancer revealed that tumor associated stroma may contain a higher density of genetic alterations than the malignant epithelium itself (Fukino, K., et al., *Cancer Res.*, 64:7231-7236 (2004)). In the current study of sporadic breast carcinomas, whether stromal cell genomic alterations significantly alter tumor behavior, as reflected in clinicopathologic features at the time of diagnosis, was investigated.

Accordingly, provided herein are methods of diagnosing breast cancer or susceptibility to breast cancer in an individual comprising detecting the presence of a loss of heterozygosity/allelic imbalance (LOH/AI) at one or more specific loci (markers) in the individual, wherein the presence of the LOH/AI at the one or more specific loci in the individual is indicative of a diagnosis of breast cancer in the individual.

In one embodiment, the invention is directed to methods of diagnosing breast cancer or susceptibility to breast cancer in an individual comprising detecting the presence of a LOH/AI at one or more loci selected from the group consisting of: D11S1999, D11S1986, ATA42G12, D5S1457, D5S1501, D5S816, D18S858, D20S103, D20S851, D22S683, D22S1045 in the individual, wherein the presence of the LOH/AI at the one or more of eleven specific loci in the individual is indicative of a diagnosis of breast cancer in the individual. In one embodiment, one or more of the loci are present in the stroma (e.g., non-malignant stroma) surrounding a tumor epithelium and/or the epithelium of the tumor.

In the methods of the invention, a sample can be obtained from the individual and used in the methods to detect the presence of the LOH/AI. The LOH/AI can be detected in any sample obtained from the individual that comprises the individual's DNA. For example, a LOH/AI can be detected in a tissue sample (e.g., skin, muscle, organ, placenta), a cell sample (e.g., fetal cells), a fluid sample (e.g., blood, amniotic fluid, cerebrospinal fluid, urine, lymph) and any combination thereof. Methods of obtaining such samples a or extracting nucleic acid from such samples are described herein and known to those of skill in the art.

Methods of obtaining such samples are well known in the art. In a particular embodiment, the presence of a LOH/AI at one or more specific loci can be detected in a sample (e.g., tissue, cell, fluid) from the tumor epithelium and/or the surrounding stroma of the tumor epithelium in the individual. The tumor epithelium and/or surrounding stroma can be obtained using any suitable method known in the art such as laser capture microdissection (LCM). In addition, the DNA can be extracted and amplified, and the LOH/AI at one or more specific loci can be detected, using any suitable methods known in the art, as described herein. As will be apparent to one of skill in the art, methods other than those described herein can be used.

In particular embodiments, the presence of LOH/AI at one or more of the loci present in stromal cells (e.g., non-malignant stromal cells, malignant stromal cells) surrounding the tumor are detected. The stromal cells can be, for example, fibroblast cells present in the stroma. In another embodiment, the presence of LOH/AI at one or more of the loci present in epithelial cells of the tumor (epithelial tumor cells) are detected.

The detection of the LOH/AI in the individual can be compared to a control. Suitable controls for use in the methods provided herein are apparent to those of skill in the art. For example, a suitable control can be established by assaying one or more (e.g., a large sample of) individuals which do not have the LOH/AI at the loci described herein. Alternatively, a control can be obtained using a statistical model to obtain a control value (standard value; known standard). See, for example, models described in Knapp, R. G. and Miller M. C. (1992) Clinical Epidemiology and Biostatistics, William and Wilkins, Harual Publishing Co. Malvern, Pa., which is incorporated herein by reference.

The methods of the present invention can further comprise determining breast cancer tumoral attributes, such as aggressiveness of the tumor or disease, extent of breast tumor invasion (e.g., tumor size (pT status; tumor grade), regional lymph node status (pN; lymph node involvement; lymph node metastasis)), of a breast cancer tumor present in an individual comprising detecting the presence of a LOH/AI at one or more specific loci in the genome of the individual.

In a particular embodiment, the invention is directed to a method of detecting an aggressive breast cancer tumor in an individual comprising detecting the presence of a LOH/AI at one or more specific loci in the individual, wherein the presence of the LOH/AI at the one or more specific loci in the individual is indicative of an aggressive breast cancer tumor in the individual.

The LOH/AI at the one or more specific loci in individuals with breast cancer described herein can also be used as targets for therapeutic and/or preventive intervention of breast cancer in an individual.

Also provided herein are kits for use in diagnosing breast cancer or susceptibility to breast cancer in an individual comprising one or more regents for detecting the presence of a LOH/AI at one or more loci selected from the group consisting of: D11S1999, D11S1986, ATA42G12, D5S1457, D5S1501, D5S816, D18S858, D20S103, D20S851, D22S683, D22S1045. For example, the kit can comprise hybridization probes, restriction enzymes (e.g., for RFLP analysis), allele-specific oligonucleotides, and antibodies. In a particular embodiment, the kit comprises at least contiguous nucleotide sequence that is substantially or completely complementary to a region of one or more of the loci comprising the LOH/AI. For example, the nucleic acids can comprise at least one sequence (contiguous sequence) which is complementary (completely, partially) to one or more loci comprising LOH/AI that is associated with breast cancer. In one embodiment, the one or more reagents in the kit are labeled, and thus, the kits can further comprise agents capable of detecting the label. The kit can further comprise instructions for detecting breast cancer using the components of the kit.

As used herein the term "individual" includes animals such as mammals, as well as other animals, vertebrate and invertebrate (e.g., birds, fish, reptiles, insects (e.g., *Drosophila* species), mollusks (e.g., Aplysia). Preferably, the animal is a mammal. The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include primates (e.g., humans, monkeys, chimpanzees), rodents (e.g., rats, mice, guinea pigs) and ruminants (e.g., cows, pigs, horses).

In addition, as used herein a cell can be a germ cell or somatic cell. Suitable cells can be of, for example, mammalian (e.g., human) origin.

Identification of the markers of the particular cancers described herein (e.g., miRNAs and their target genes for follicular thyroid carcinoma; haplotype blocks for PTEN Hamartoma Syndrome, and loss of heterozygosity/alleleic imbalance for head and neck squamous cell carcinoma and breast cancer) provide for methods of detecting recurrence of the cancer in an individual that is in remission, or has been treated for the cancer comprising detecting the markers in the individual.

In addition, the markers provide for methods of screening an asymptomatic individual for the particular cancer comprising detecting the marker in the asymptomatic individual.

Also encompassed by the present invention are methods of monitoring a treatment regimen for cancer in an individual comprising monitoring the marker(s) in the individual undergoing or completing a particular treatment regimen.

The present invention also provides for methods of monitoring an individual at risk for developing the particular cancer by assaying for the presence of the marker(s) in the individual at regular intervals (e.g., once every 6 months; once a year; once every two years).

Example 1

MicroRNAs Deregulated in Follicular Thyroid Carcinoma

Materials and Methods

Tissue Specimens

In total, 47 thyroid samples (23 FTC, 20 FA and 4 normal control thyroid) were analyzed in this study (Table 2 for detailed histologies). No oncocytic or hypercellular adenomas were analyzed in this study. A set of 8 FA and 12 FTC were used for the miRNA-chip array and a set comprising 12 FTC and 12 FA was analyzed on the GeneChip array. 6 FTC and 6 FA overlapped in these 2 studies. Additional validation of the differentially expressed miRNAs was performed in an independent set of 9 follicular neoplasias (5 FTC and 4 FA) and 4 normal control thyroid, not used on the miRNA-chip. Gene expression validation was done in a set of 14 FTC and 9 FA by quantitative RT-PCR. The study, which utilized anonymized unlinked samples, was approved by the participating Institutional Review Boards for Human Subjects' Protection.

miRNA-Chip Expression Analysis

The miR chip analysis followed the design and protocols as described previously by Liu et al., except that the human & mouse microRNA 11K version 2 chip was used (Liu, C. G., et al., *Proc. Natl. Acad. Sci. U.S.A.,* 101:9740-4 (2004)). In brief, following biotin end-labeling, the small RNAs were hybridized on a custom microRNA array chip that contains 460 mature miRNA probes (235 *Homo sapiens,* 222 *Mus musculus* and 3 *Arabidopsis* manual). The 235 human miRNA are derived from a total of 319 (73.7%) unique, mature miRNAs known today. For each miRNA, 40-mer 5' amine modified C6 oligos were printed in quadruplicate on Amersham CodeLink activated slides (Amersham, Piscataway, N.J.). Quantification of biotin-containing transcripts was achieved after chip washing, processing and incubation with streptavidin-Alexa647 using the Axon 4000B scanner and GENEPIX Pro 6.0 software package (Molecular Devices, Sunnyvale, Calif.). A detailed description of sequence selection, chip construction and array protocols can be found on EMBL-EBI, Array Express # E-TABM-68.

MicroArray Expression Analysis

Total RNA extraction was performed under standard protocol using the TRIzol Reagent (Invitrogen, Carlsbad, Calif.) and purified with the RNeasy Kit (Qiagen, Valencia, Calif.). The sample preparation, hybridization and analysis were performed as described previously in detail (Weber, F., et al., *J. Clin. Endocrinol. Metab.,* 90:2512-21 (2005); Aldred, M. A., et *Clin. Oncol.,* 22:3531-9 (2004); Auer, H., et al., *Nat. Genet.,* 35:292-3 (2003)). Chip data can be obtained from EMBL-EBI, Array Express # E-MEXP-97.

miRNA and Gene Expression Validation

The mirVana miRNA isolation kit was used for isolation and enrichment of small RNA fractions (Ambion, Austin, Tex.). MicroRNA expression analysis was done for miR197, miR-328 and miR-346 by quantitative RT-PCR, according to the manufacturer's protocols (Ambion, Austin, Tex.). Optimized primers for the reverse transcription (RT) and polymerase chain reaction (PCR) are commercially available (Ambion, Austin, Tex.).

Endpoint PCR was done with HotStar Taq Polymerase (Qiagen, Valencia, Calif.) and primers as followed: ACVR1 5'-TTCCTCACTGAGCATCAACG (SEQ ID NO. 1) and 5'-TAATGAGGCCAACCTCCAAG (SEQ ID NO. 2); TSPAN3 5'-AGCCCTGCTTTTCATCATTG (SEQ ID NO. 3) and 5'-TTCTGAATGCTGCGATCAAC (SEQ ID NO. 4); EFEMP2 5'-GCCCAAACCTGTGTCAACTT (SEQ ID NO. 5) and 5'-ATGAAGGCTGCTCTCGACAT (SEQ ID NO. 6); CFLAR 5'-TTTCTTTGCCTCCATCTTGG (SEQ ID NO. 7) and 5'-GAAGCTCACAAGGGTCTTGC (SEQ ID NO. 8), GAPDH 5'-GGGCTGCTTTTAACTCTGGTAA (SEQ ID NO. 9) and 5'-ATGGGTGGAATCATATTGGAAC (SEQ ID NO. 10).

Cell Lines and Culture Conditions

The HEK293T, human embryonic kidney cells, 2 human follicular thyroid cancer cell lines (FTC133 and K5) and 1 human papillary thyroid cancer cell lines (NPA87) were cultured in DMEM supplemented with 10% fetal bovine serum (FBS), and 100 units/ml penicillin and streptomycin (Life Technologies, Invitrogen). For cell growth assay equal numbers (90,000) of cells were plated in 12-well plates. After 8, 12, 24 and 48 hours, the medium was removed and the cells were washed and harvested. After trypsinization, viable cells (excluding trypan blue) were counted.

Transient Over-Expression of miRNAs

Precursor miRNAs (prec-miR-197 and prec-miR-346) (Ambion, Austin, Tex.) were transiently transfected into HEK293T cells with the siPORT NeoFx transfection reagent (Ambion, Austin, Tex.). For mock transfection conditions, prec-miR was substituted with random oligonucleotides at equal concentration. Optimal transfection efficiency was empirically determined at 3 µl siPORT NeoFx, 10 nM small RNA for 90,000 cells. All experiments were done in triplicate.

Suppression of Endogenous miRNA Function

Commercially available anti-miR™ miRNA inhibitors (Ambion, Austin, Tex.) directed against each of the mature sequences of miR-197 and miR-346 were transfected into 2 human thyroid carcinoma cell lines (FTC133 and K5) as well as NPA87 (human papillary thyroid carcinoma) cell line, to study the effect on growth potential. 20 to 80 nM of anti-miR oligonucleotides (Ambion, Austin, Tex.) were transfected with the siPORT NeoFX transfection agent (3 µl) into the respective cells (90,000 cells/well of a 12-well plate).

Protein Isolation and Western Blot

Protein was isolated from tumor samples using RIPA buffer (50 mM Tris pH 8.0, 150 mM NaCl, 1% Triton and 0.1% SDS) containing proteases and subsequently sonication. Protein extracts (15 µg) were separated on a 10% SDS-PAGE gel and electrophoretically transferred onto nitrocellulose. After blocking for non-specific binding, blots were then incubated with either ACVR1 (Abgent; San Diego, Calif.) or Actin (Sigma; Saint Louis, Miss.) primary antibody (1:1000 in 3% BSA). Following incubation with an anti-rabbit secondary antibody (1:2500 dilution in 5% milk; Promega; Madison, Wis.) the protein bands were visualized using enhanced chemiluminescence as described by the manufacturer (Amersham Pharmacia Corp; Piscataway, N.J.).

Statistical Methods

For the miRNA-chip data, spots flagged as poor quality during image analysis were excluded from analysis. The average intensity over quadruplicate spots for each miRNA was computed and a log base 2 transformation was then applied to the expression values. A median-centering array normalization procedure was then performed to allow for comparison across arrays. The primary interest was comparing miRNA expression between FA and FTC patient samples. Since array samples were hybridized at two different times, the possibility of a batch effect was accounted for by using a 2-way ANOVA with batch as a block variable. The 2 hybridization sets included both FA and FTC samples, with 3 FA and 5 FTC in the first and 5 FA and 7 FTC in the second set. A nominal significance level of 0.001 was employed in all statistical comparisons. BRB ArrayTools Version 3.3 (National Cancer Institute, Rockville, Md.) was used for all analyses. Gene-Chip HG-U133A raw data were analyzed with the DNA-Chip Analyzer Software (dChip) developed by Li and Wong (www.dchip.org) as described by us previously in detail (Weber, F., et al., *J. Clin. Endocrinol. Metab.,* 90:2512-21 (2005)). A linear diagonal discriminant analysis was used for class prediction in the gene expression data. The performance of the predictor was tested using leave-one-out cross-validation method based on 2000 random permutations. A 2-tailed Student's T-test for independent samples, assuming equal variance, was used to determine difference between mean gene expressions in the validation analysis and cell growth assay. For analysis between groups, Fisher 2-tailed exact test was used.

Results

Based on a high-density custom miRNA chip 4 miRs were identified, miR-192, miR-197, miR-328 and miR-346 (p=0.00009, 0.00063, 0.00021 and 0.000496, respectively), all of which are over-expressed in FTC compared to FA (1.34, 1.82, 1.48 and 1.39 fold) (Table 1 and Table 3). Two miRNAs (miR-192 and miR-197) have previously been experimentally validated in human (i.e., are truly human miR expressed in human tissues), while miR-328 and miR-346 are only predicted human homologues; however, their expression in human tissue has now been shown (FIGS. 1A-1C) (Lagos-Quintana, M., et al., *Rna,* 9:175-9 (2003)).

Validation of miR Over-Expression

In an independent set of 9 follicular thyroid neoplasias (5 FTC and 4 FA) and 4 normal control thyroids, the differential expression of the mature miR-197 (over-expressed in FTC vs. FA by 2.00-fold, p=0.0044) and miR-346 (1.37-fold expressed in FTC over FA, p=0.049) were validated using quantitative RT-PCR (FIGS. 1A-1C). miR-192 was restricted to in silica analyses because specific reverse transcription and PCR primers for miR-192 could not be designed and tissue availability did not allow for analysis by Northern Blot hybridization. However, for miR-328, even though the average expression was higher in FTCs compared to FAs, this difference did not meet statistical significance in this validation set (p>0.08; data not shown), and was not pursued further.

Functional Effect of Identified miRNAs

Figure 2B:
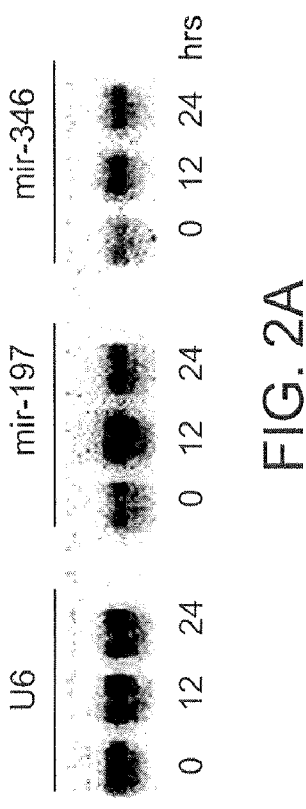
Figure 2C:
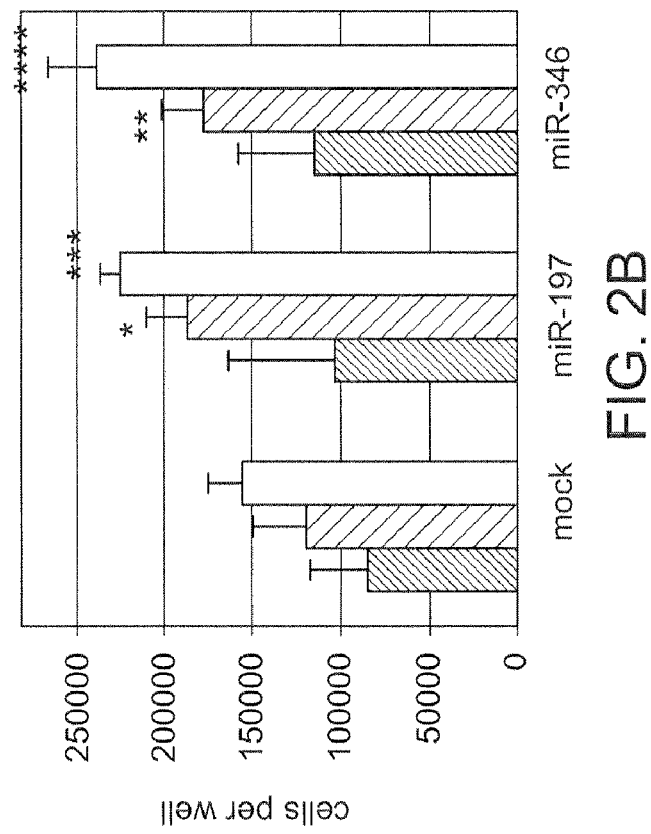

The functional consequences of miRNA over-expression were determined by transient transfection of 2 of the identified and most robustly validated miRNAs (miR-197 and miR-346) in a human non-neoplastic cell line (HEK293T). First, transfection efficiency was confirmed by detecting overexpression of miR-197 and miR-346 above endogenous levels (FIG. 2A). At 12 and 24 hours after miR-197 or miR-346 transfection, significantly induced cell proliferation was noted with approximately 1.5-fold more viable cells than before transfection ($p=0.003$-$0.049$; see FIG. 2B and legend). For both miR-197 and miR-346, expressional levels were seen to peak at 12 hours post-transfection and begin to return to basal levels by 24 hours (FIG. 2A). The non-viable cell population increased by factors of 1.7 to 2.28-fold and thus mirrors the increase in the viable cell count observed in miR-197 and miR-346 transfected cells (FIG. 2C).

Suppression of Endogenous miRNA Function and Effect on Growth Potential

Figure 3B:
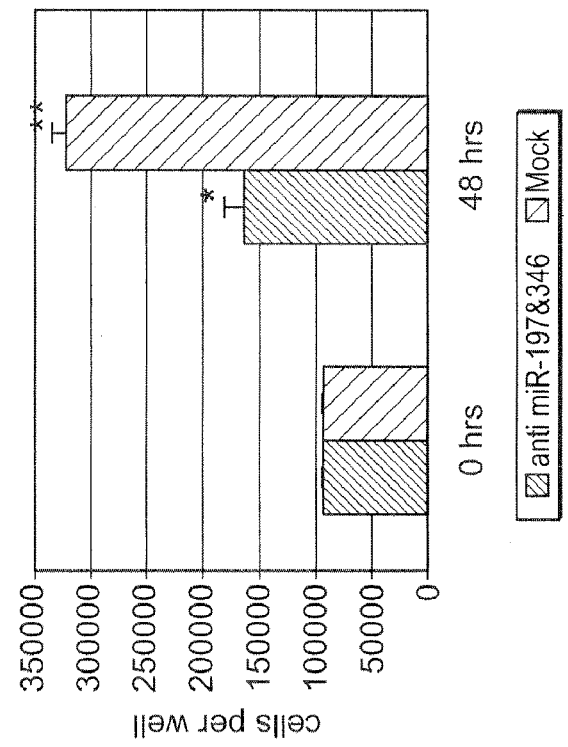
FIGS. 3A-3C. Functional activity of endogenous miR-197 and miR-346 was inhibited by transfection of synthetic, chemically modified anti-miR-197 and anti-miR-346 oligonucleotides into human follicular thyroid cancer cell lines.
Figure 3A:
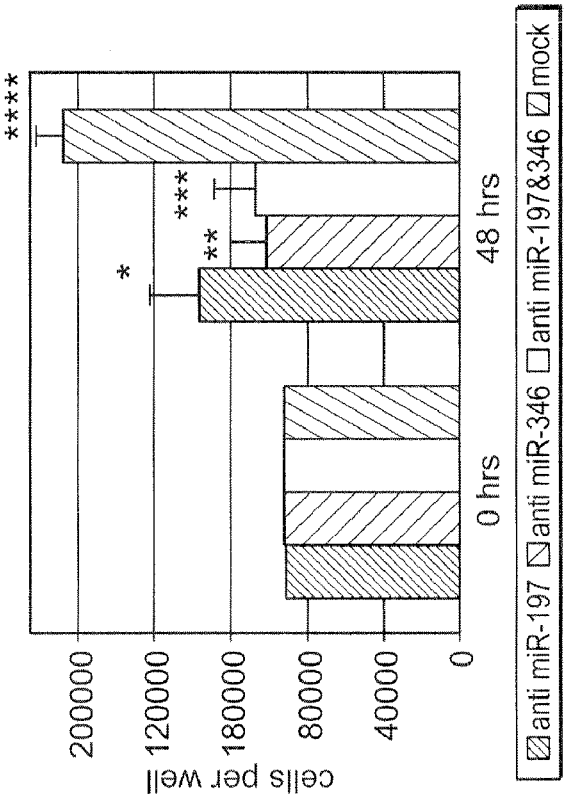
Figure 3C:
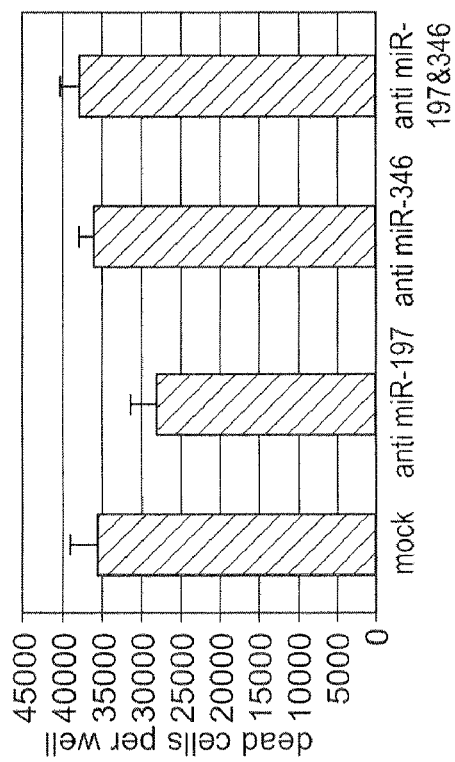

Commercially available miRNA inhibitors (Ambion, Austin, Tex.) were used to suppress the functional effect of endogeneous miRNA-197 and miR-346. FTC-133 cells under control conditions resulted in a 2.31-fold increase in cell number within 48 hr (absolute cell count at 48 hours vs. 0 hours, FIG. 3A). In contrast, transfection of anti-miR-197 and/or anti-miR-346 into FTC-133 cells resulted in a 2-fold growth suppression, (i.e., a 1.11 to 1.5-fold increase in cell number instead of the control 2.31-fold was noted during the same time period (48 hours vs. 0 hours)). The effect of this miRNA inhibition on FTC-133 cell proliferation was significant ($p=0.0128$, $0.0016$ and $0.0026$, respectively, FIG. 3A). A similar effect was seen in a second human FTC cell line (K5) (FIG. 3B) while neither inhibitor showed any effect in the NPA-87 cell line which lacks endogenous miRNA-197 and miRNA-346 over-expression (data not shown). The number of non-viable cells did not differ between anti-miR™ oligonucleotide and control conditions (FIG. 3C).

In Silico Analysis of Predicted miRNA Target Gene Expression

The MicroCosm web resource (Version 2.0) maintained by the Sanger Institute was utilized to predict potential miRNA target sequences and re-interrogated the data from previously published gene expression array [HG-U133A, 12 FTC and 12 FA] for these target genes (Weber, F., et al., *J. Clin. Endocrinol. Metab.*, 90:2512-21 (2005)). For miR-197, 57 of the 496 represented target genes showed significant under-expression in FTCs compared to FA when using a cut off value of −1.5-fold and a maximum p-value of 0.05 (Table 4). Using the same criteria, 24 out of the 278 target genes for miR-346 and 51 out of 379 target genes predicted for miR-192 were significantly under-expressed in FTCs compared to FAs (Tables 5 and 6).

To ensure specificity of the findings in the context of FTC, this analysis was repeated using the predicted target genes for miR-221, miR-222 and miR-146a, which are specific for papillary thyroid carcinogenesis (He, H., et al., *Proc. Natl. Acad. Sci. USA.*, 102:19075-80 (2005)). These analyses revealed that the PTC-miR's are not differentially regulated between FTC and FA. Between 418 and 566 target genes were present on the HG-U133A chip, but of those, only 20 (miR-146a, 4.8%) to 29 (miR-222, 5.1%) genes were significantly under-expressed in FTC. This is significantly less than what was observed for the FTC-specific miR-192 (13.5%, $p<0.000004$), miR-346 (8.6%, $p<0.018$) and miR-197 (11.5%, $p<0.00011$).

Validation of Predicted Target Genes

Figure 4A:
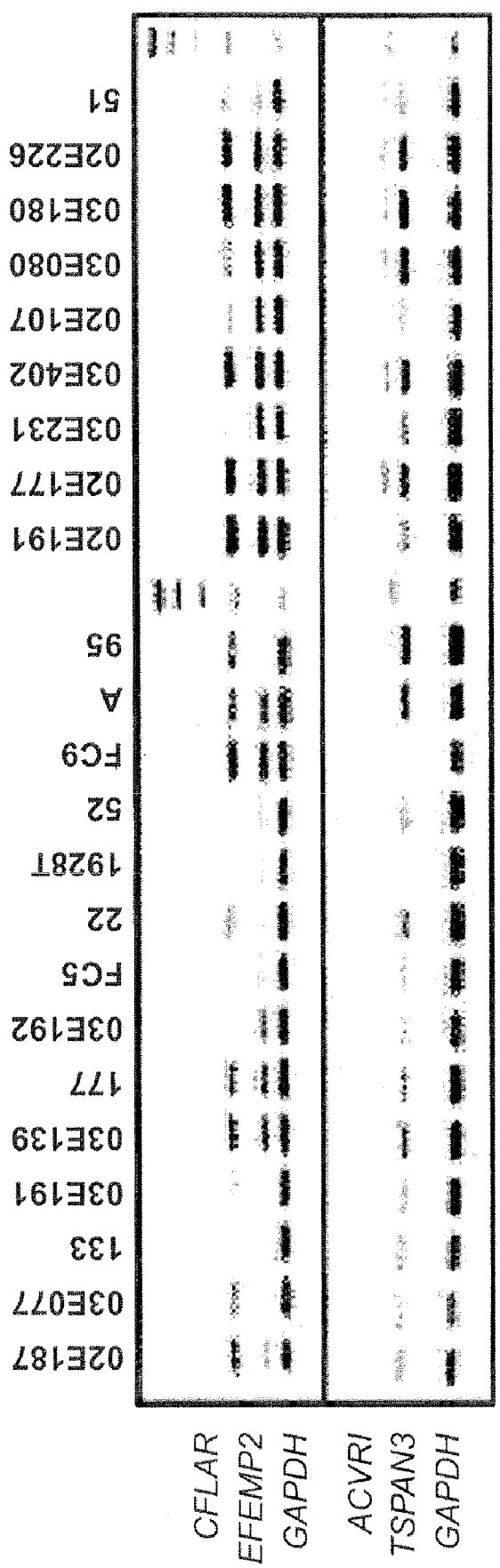

In order to verify that in silco predicted miRNA targets genes can be regulated by the respective miRNA in vitro, 2 out of 57 miR-197 targets (ACVR1, TSPAN3), and 2 out of 24 miR-346 target genes (EFEMP2, CFLAR), were selected for proof of principle (Tables 4, 5). The 2 target genes (ACVR1 and TSPAN3) for miR-197 that were significantly under-expressed in FTC compared to FA (1.9- and 1.5-fold, $p=0.00039$ and $p=0.03$) and to normal thyroid control (FIGS. 4A-4E) were successfully validated. For ACVR1, differences in gene transcript expression were reflected by protein levels as well (FIGS. 4D, 4E). Similarly, the 2 miR-346 target genes EFEMP2 and CFLAR, were under-expressed by 2.2-fold ($p=0.035$) and 1.9-fold ($p=0.000014$) in FTCs compared to FAs (FIGS. 4A-4E).

Figures 5A, 5B:
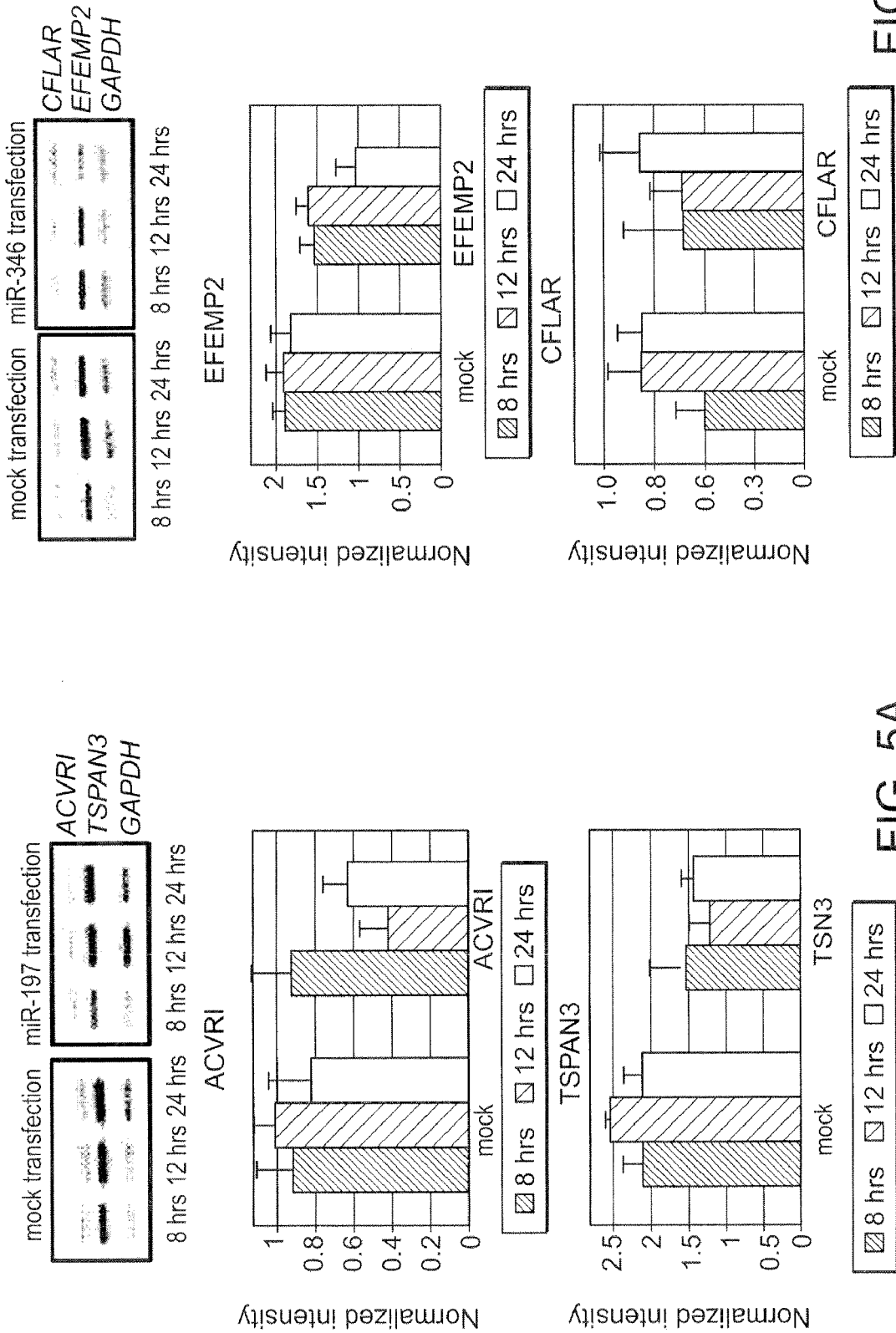
FIGS. 5A-5B. Effect of miR-197 or miR-346 over-expression on the expression of their ACVR1 and TSPAN3 determined at 8, 12 and 24 hours after transient transfection with pre-miR-197.

In the HEK293T cell model, over-expression of miR-197 leads to reduced mRNA levels of ACVR1 and TSPAN3 at 12 hours (down 2.5- and 2.0-fold, respectively) and 24 hours (down 1.35- and 1.5-fold, respectively) (FIG. 5A). Interestingly, over-expression of miR-346 resulted in a continuous reduction of EFEMP2 mRNA levels at both 12 hours (down 1.2-fold) and 24 hours (down 1.89-fold) (FIG. 5B). In contrast, over-expression of miR-346 did not significantly influence the transcript levels of CFLAR in our HEK293T model (FIG. 5B). Neither miRNA had any effect on the gene transcription of non-target genes (e.g., ACVR1, TSPAN3 for miR-346 and CFLAR, EFEMP2 for miR-197).

In addition, the performance of these 3 validated miRNA target genes (ACVR1, TSPAN3 and EFEMP2) were evaluated as a molecular classifier to distinguish FTC and FA. Based on the expression of ACVR1, TSPAN3 and EFEMP2, using established linear discriminant analysis and employing leave-one-out cross-validation, 88% of class labels (e.g., FTC or FA) were correctly predicted based on re-mined expression array data (Weber, F., et al., *J. Clin. Endocrinol. Metab.*, 90:2512-21 (2005); Radmacher, M. D., et al., *J. Comput. Biol.*, 9:505-11 (2002)). This was further confirmed by using the second sample set, analyzed by RT-PCR. Here this ACVR1-TSPAN3-EFEMP2 profile allowed accurate identification of 87% of the samples as benign or malignant, providing a sensitivity of 85.7% (12 out of 14) and specificity of 88.9% (8 out of 9) to identify FTC.

Discussion

Over the last few years, numerous molecular alterations have been described that are likely to participate in the development of benign and malignant neoplasias derived from thyroid follicular epithelial cells (Cerutti, J. M., et al., *J. Clin. Invest.*, 113:1234-42 (2004); Umbricht, C. B., et al., *Clin. Cancer Res.*, 10:5762-8 (2004); Weber, F., et al., *J. Clin. Endocrinol. Metab.*, 90:2512-21 (2005); Segev, et al., *Surg. Oncol.*, 12:69-90 (2003); Aldred, M. A., et al., *J. Clin. Oncol.*, 22:3531-9 (2004); Aldred, M. A., et al., *Oncogene*, 22:3412-6 (2003); Sarquis, M. S., et al., *J. Clin. Endocrinol. Metab.* 91:262-9 (2006); Weber, F., et al., *J. Clin. Endocrinol. Metab.* 90:1149-55 (2005); Fagin, J. A., *Endocrinology*, 143:2025-8 (2002); Kraiem. Z., et al., *Thyroid*, 10:1061-9 (2000)). However, the evolution of events causing malignant transformation is still limited. In this study using a high-density miRNA chip platform, only 4 human small RNAs (miRNA), miR-192 (1103.1), miR-197 (1p13.3), miR-328 (16q22.1) and miR-346 (10q23.2) that are over-expressed in FTC compared to FA were identified. None of these miRNAs have previously been associated with thyroid neoplasia and appear to be specific for follicular thyroid carcinomas. It is interesting to note that only a few miRNAs are deregulated between FTC and FA. Other studies, comparing cancer to their matching normal tissue, identified as many as 30 differentially regulated miRNAs (Chen, C. Z., et al., *N. Engl. J. Med.*, 353:1768-71 (2005); Iorio, M. V., et al., *Cancer Res.*, 65:7065-70 (2005); Murakami, Y., et al., *Oncogene*, 25:2537-45 (2005); He, H., et al., *Proc. Natl. Acad. Sci. U.S.A.*, 102:19075-80 (2005)). The majority of these miRNA expressional differences occurred in the range between 1.2- and 2-fold, similar to what we observed in our study (Iorio, M. V., et al., *Cancer Res.*, 65:7065-70 (2005); Murakami, Y., et al., *Oncogene*, 25:2537-45 (2005)). Based on these observations, especially those made in PTC (He, H., et al., *Proc. Natl. Acad. Sci. U.S.A.,* 102:19075-80 (2005)), one might hypothesize that the deregulation of several miRNA's—not identified in this study—occur equally in benign and malignant follicular neoplasia.

Functional Effect of miR-197 and miR-346

Over-expression of the most robustly validated miRNAs (miR-197 and miR-346) induced marked proliferation in vitro. As proof of principle, the functional link between miR-197 and miR-346 and the transcriptional suppression of 3 target genes was validated. First, EFEMP2 (or fibulin 4) is involved in stabilization and organization of ECM structures (Argraves, W. S., et al., *EMBO Rep.,* 4:1127-31 (2003)). There is evidence that EFEMP2 harbors tumor-suppressor functions, which were shown herein to be inhibited by miR-346 deregulation (Argraves, W. S., et al., *EMBO Rep.,* 4:1127-31 (2003); Gallagher, W. M., et al., *FEBS Lett.,* 489: 59-66 (2001)). Second, as a functional consequence of deregulated miR-197 in FTC, ACVR1 as well as tetraspanin 3 (TSPAN3) becomes under-expressed. Activin A as well as TGF-B1 are ligands for the activin A receptors type 1 (ACVR1) and have been shown to be potent growth inhibitors in various human cells, including thyroid epithelium (Schulte, K. M., et al., *Thyroid,* 11:3-14 (2001)). While no functional data exist on TSPAN3, there are such data for CD63, another member of the tetraspan superfamily with highest homology to TSPAN3 (Boucheix, C., et al., *Expert Rev. Mol. Med.,* 2001:1-17 (2001)). Expression levels have been shown to be inversely correlated with the metastatic potential in melanoma (Boucheix, C., et al., *Expert Rev. Mol. Med.,* 2001:1-17 (2001); Schulte, K. M., et al., *Horm. Metab. Res.,* 32:390-400 (2000)). Finally, the findings provided herein show the limitations of in silico analysis when identifying miRNA target genes. For one (CFLAR) out of the 4 genes tested in this study, a functional link between the miRNA and the potential target gene could not be established in vitro despite in silico evidence.

Implications of Deregulated miRNAs for the Accurate Pre-Operative Diagnosis of FTC The over-expression of a small set of miRNA's with subsequent cascading down regulation of target tumor suppressor genes, represents a powerful mechanism where a small but significant (1.2- to 2-fold range) over-expression can lead to larger downstream perturbations that inactivate numerous genes potentially participating in FTC-genesis. These miRNAs and their target genes, therefore, likely provide novel molecular markers to accurately differentiate malignant (FTC) and benign thyroid neoplasia (FA). Based on the set of differentially expressed miRNAs (miR-192, miR-197, miR-328 and miR-346) in our miRNA-Chip experiment, class labels (FTC versus FA) in 74% of all cases could be correctly predicted. However, the usefulness of miRNAs for diagnostic purposes should be considered since in follicular thyroid neoplasias, the diagnosis must rely on material obtained from fine needle aspiration biopsies and it is our observation that needle wash out material does not provide enough of the small RNA fraction for reproducible analysis (unpublished observation). Therefore, the target genes of these miRNA's likely provide for better diagnostic markers. Using the common approach of diagonal linear discriminant analysis and leave-one-out-cross validation method (Weber, F., et al., *J. Clin. Endocrinol. Metab.,* 90:2512-21 (2005); Radmacher, M. D., et al., *J. Comput. Biol.,* 9:505-11 (2002)), the miRNA target gene classifier (ACVR1, TSPAN3 and EFEMP2) described herein achieved an accuracy of over 87% to differentiate between FTC and FA in 2 independent sample sets (see Results). While the molecular markers presented here perform similarly well as other proposed models based on gene expression profiling such as reported by Cerutti et al. (e.g., 83% accuracy) or Umbricht et al. (e.g., 77% accuracy), it does not perform superiorly to our previously identified 3-gene signature (96.7% accuracy) (Cerutti, J. M., et al., *J. Clin. Invest.,* 113:1234-42 (2004); Umbricht, C. B., et al., *Clin. Cancer Res.,* 10:5762-8 (2004); Weber, F., et al., *J. Clin. Endocrinol. Metab.,* 90:2512-21 (2005)). Nonetheless, all minimally invasive FTCs (03E077, 03E191 and 03E192) were correctly identified as a malignancy using the miRNA target gene classifier (ACVR1, TSPAN3 and EFEMP2). Considering the advancement over the last years to identify and validate such molecular markers, the currently unanswered question will need to be addressed. That is, if indeed there is an adenoma-carcinoma sequence in follicular thyroid cancer, what will be the treatment of choice for those patients diagnosed with FA preoperatively?

Suppression of Endogenous miRNA Expression—Clinical Implications

In the human thyroid cancer cell line models described herein, the introduction of synthetic chemically modified anti-miRNA™ oligonucleotides directed against miR-197 or miR-346 induced a significant growth arrest. This phenomenon was observed both in FTC-133 and K5 FTC cells, while the papillary thyroid cancer cell line (NPA87), lacking deregulation of these miRNA's, was not affected. Recently it has been discussed and tested that interference with miRNA function opens novel opportunities for therapeutic intervention (Weiler, J., et al., *Gene Ther.,* 13(6):496-502 (2006)); Grunweller, A., et al., *Curr. Med. Chem.,* 12:3143-61 (2005); Poy, M. N., et al., *Nature,* 432:226-30 (2004); Krutzfeldt, J., et al., *Nature,* 438:685-9 (2005)). The study described herein provides in vitro evidence for the feasibility of this approach for FTC, something that clearly will need further in vivo validation. However, it is likely that the interference with the deregulated miRNA profile in FTC might allow re-activation of suppressed target genes and ultimately affect an array of downstream targets to reverse the malignant phenotype or at least cause growth arrest. In addition, the findings provided herein indicate that the interference with specific miRNA(s) is not only cancer-type specific but also could be sub-histology-specific in a given type of cancer, in this case, specific for FTC. In contrast, shown herein is that miR-221 and miR-222, which are implicated in PTC carcinogenesis, do not play in role in follicular neoplasia development (He, H., et al., *Proc. Natl. Acad. Sci. U.S.A.,* 102:19075-80 (2005)).

In conclusion, the study described herein shows that a small set of differentially regulated miRNAs are specifically deregulated in follicular thyroid cancer and likely participate in the transformation from benign to malignant neoplasia. These small RNAs and their target genes point to new targets to improve preoperative diagnosis of follicular nodule, and even therapy for a disease that continues to challenge us in the clinical setting.

TABLE 1 miRNA's differentially expressed between FTC and FA

| microRNA | FA[a] | FTC[a] | fold difference | p-value |
|---|---|---|---|---|
| hsa-miR-197[b] | 848.3 | 1545.7 | −1.82 | 0.0004969 |
| hsa-miR-328[b] | 666.2 | 990.4 | −1.49 | 0.0000991 |
| hsa-miR-346[b] | 620.4 | 862.2 | −1.39 | 0.0006331 |
| hsa-miR-192 | 552.6 | 741.5 | −1.34 | 0.0002103 |

[a]Values indicate average normalized expression for the respective microRNA for 12 FTC or for 8 FA analyzed on the OSU-CCC microRNA Chip version 2.0.
[b]miRNAs further analyzed by qRT-PCR in an independent set of 9 follicular neoplasias comprising 5 FTC and 4 FA

TABLE 2

Histopathological description of 23 follicular thyroid carcinoma used for analysis

| Sample ID | Histopathology | sex/age | size |
|---|---|---|---|
| 02E187[b,c] | FTC, oxyphilic type, widely invasive | na | 2.2 |
| 03E077[b,c] | FTC, minimally invasive, oxyphillic type | f/48 | 2.5 |
| 133[c] | FTC, oxyphilic type, widely invasive | f/83 | na |
| 03E139[b,c] | FTC, oxyphilic type, widely invasive | f/61 | 3.0 |
| 177[b,c] | FTC, well differentiated, widely invasive | f/78 | na |
| FC5[c] | FTC, well differentiated, widely invasive | na | na |
| 1928T[c] | FTC, insular type | na | na |
| 52[b,c] | FTC, recurrence | m/40 | na |
| FC9[c] | FTC, well differentiated, widely invasive | na | na |
| A[c] | FTC, well differentiated, widely invasive | m/68 | 3.8 |
| 03E192[a,b,c] | FTC. minimally invasive | f/25 | na |
| 22[a,b,c] | FTC, well differentiated, widely invasive | f/67 | 2.5 |
| 04E341[a] | FTC, oxyphilic type, widely invasive | f/63 | 2.0 |
| 04E342[a] | FTC, insular type | f/75 | 1.5 |
| 95[a,b,c] | FTC, recurrence | f/69 | na |
| 05E222[a] | FTC, moderately invasive | f/65 | 1.2 |
| 03E193[a,b] | FTC, oxyphilic type, minimally invasive | f/82 | 5.0 |
| 05E094[a] | FTC, well differentiated, widely invasive | m/49 | 4.4 |
| 03E191[a,b,c] | FTC, minimally invasive | f/62 | 2.4 |
| 02E187[a] | FTC, oxyphilic type, widely invasive | na | 2.2 |
| 05E159[a] | FTC, moderately invasive | f/73 | 5.2 |
| 408[a,b] | FTC, oxyphilic type, widely invasive | f/71 | 2.0 |
| 03E041[b] | FTC, oxyphilic type, metastasized | f/72 | na | f = female,
m = male,
na—not available.
[a]tumors analyzed on the miRNA Chip,
[b]tumors analyzed on the HG-U133A GeneChip,
[c]tumors used for validadtion.
Size indicates maximal diameter in cm of the tumor.
Minimally invasive, tumor invasion through the entire thickness of the tumor capsule;
moderately invasive, tumor with angioinvasion, with or without tumor invasion through the entire thickness of the tumor capsule;
widely invasive, broad area(s) of transeapsular invasion.

TABLE 3

Normalized Log-Transformed miRNA Expression for Significant miRNAs

| ID | Type | hsa-miR-197 | hsa-miR-328 | hsa-miR-346 | hsa-miR-192 |
|---|---|---|---|---|---|
| 04E428 | FA | 8.749 | 8.660 | 8.860 | 8.594 |
| 02E167 | FA | 10.517 | 9.921 | 9.422 | 9.348 |
| 02E226 | FA | 9.068 | 8.814 | 9.042 | 8.936 |
| 03E180 | FA | 9.402 | 8.799 | 8.883 | 8.666 |
| 02E191 | FA | 10.257 | 9.399 | 9.610 | 9.429 |
| 478T | FA | 10.118 | 9.895 | 9.415 | 9.450 |
| 03E080 | FA | 10.118 | 9.895 | 9.415 | 9.450 |
| 05E165 | FA | 9.598 | 9.656 | 9.571 | 9.007 |
| | mean | 9.728 | 9.380 | 9.277 | 9.110 |
| | $2^{mean}$ | 848.3 | 666.2 | 620.5 | 552.6 |
| 03E192 | FTC | 10.532 | 9.774 | 9.320 | 9.628 |
| 22 | FTC | 10.395 | 9.903 | 10.154 | 9.360 |
| 04E341 | FTC | 10.204 | 9.477 | 9.505 | 9.074 |
| 04E342 | FTC | 9.634 | 9.257 | 9.630 | 8.847 |
| 95 | FTC | 10.562 | 9.694 | 9.370 | 9.237 |
| 05E222 | FTC | 10.663 | 10.265 | 9.870 | 9.811 |
| 03E193 | FTC | 11.057 | 10.303 | 9.733 | 9.744 |
| 05E094 | FTC | 10.415 | 9.810 | 9.707 | 9.662 |
| 03E191 | FTC | 11.253 | 10.247 | 9.973 | 9.774 |
| 02E187 | FTC | 11.804 | 10.041 | 9.850 | 9.985 |
| 408 | FTC | 10.550 | 10.677 | 9.930 | 9.858 |
| 05E159 | FTC | 10.059 | 9.974 | 9.980 | 9.433 |
| | mean | 10.594 | 9.952 | 9.752 | 9.534 |
| | $2^{(mean)}$ | 1545.7 | 990.4 | 862.2 | 741.6 |

TABLE 4

Predicted miR-197 target genes differentially expressed between FTC and FA

| | Gene Expression - HG-U133A | | | | Target Prediction[b] | |
|---|---|---|---|---|---|---|
| | | | Fold | | | |
| Gene | FA[a] | FTC[a] | Change | P value | Score[b] | P value |
| CHIC2 | 152.7 | 88.2 | -1.73 | 0.00010 | 16.49 | 0.00018 |
| CPNE6 | 78.7 | 32.4 | -2.43 | 0.00010 | 16.15 | 0.00591 |
| TSPN3[c] | 642.2 | 265.6 | -2.42 | 0.00033 | 15.90 | 0.00118 |
| HNF4A | 21.6 | 7.7 | -2.80 | 0.00220 | 15.53 | 0.00095 |
| WDR6 | 341.4 | 204.1 | -1.67 | 0.00052 | 17.87 | 0.00494 |
| ABCC3 | 59.0 | 9.4 | -6.28 | 0.02287 | 15.99 | 0.00031 |
| VDP | 225.4 | 80.4 | -2.80 | 0.00018 | 14.73 | 0.00068 |
| ZNF302 | 182.5 | 89.0 | -2.05 | 0.00005 | 16.46 | 0.03331 |
| FBXW7 | 74.3 | 33.0 | -2.25 | 0.00018 | 14.70 | 0.00011 |
| ACVRl[c] | 401.5 | 201.5 | -1.99 | 0.00004 | 16.57 | 0.03303 |
| PIPOX | 40.1 | 24.6 | -1.63 | 0.00180 | 16.65 | 0.00206 |
| RAD51 | 37.8 | 23.3 | -1.62 | 0.00007 | 17.04 | 0.02393 |
| PEX13 | 56.8 | 27.9 | -2.04 | 0.00047 | 15.47 | 0.00656 |
| TAF4B | 176.4 | 94.5 | -1.87 | 0.00001 | 15.97 | 0.04413 |
| RXRB | 37.6 | 17.0 | -2.22 | 0.01302 | 17.45 | 0.01921 |
| HNRPD | 819.5 | 528.0 | -1.55 | 0.00022 | 15.77 | 0.00163 |
| MMP23A | 37.9 | 18.4 | -2.06 | 0.00188 | 14.70 | 0.00144 |
| CPSF1 | 90.3 | 44.3 | -2.04 | 0.00387 | 15.76 | 0.00501 |
| DPH2L1 | 64.0 | 31.9 | -2.01 | 0.00011 | 15.17 | 0.01221 |
| RAB28 | 28.0 | 14.9 | -1.88 | 0.00144 | 16.38 | 0.03498 |
| DCBLD2 | 46.2 | 26.6 | -1.74 | 0.00934 | 15.35 | 0.00018 |
| AGR2 | 353.4 | 25.1 | -14.08 | 0.02230 | 15.69 | 0.00682 |
| THRAP5 | 33.7 | 21.6 | -1.56 | 0.03617 | 17.06 | 0.00035 |
| HMGN1 | 1583.2 | 1022.4 | -1.55 | 0.00014 | 15.43 | 0.00353 |
| CLIC1 | 885.3 | 560.7 | -1.58 | 0.00091 | 16.60 | 0.03277 |
| PRKD2 | 133.4 | 84.5 | -1.58 | 0.00015 | 14.94 | 0.00311 |
| NP_057452.1 | 127.6 | 77.2 | -1.65 | 0.00352 | 15.08 | 0.00087 |
| KNS2 | 113.8 | 69.2 | -1.65 | 0.00271 | 15.44 | 0.00391 |
| TSPYL1 | 985.5 | 530.9 | -1.86 | 0.00015 | 14.61 | 0.00821 |
| CREBL1 | 39.4 | 25.2 | -1.56 | 0.00908 | 18.72 | 0.00903 |
| ALMS1 | 100.4 | 64.6 | -1.55 | 0.00211 | 17.24 | 0.02302 |
| RBM4 | 447.1 | 284.4 | -1.57 | 0.00079 | 16.44 | 0.03364 |
| LRP4 | 167.6 | 42.4 | -3.95 | 0.03356 | 14.82 | 0.00220 |
| DPYSL3 | 61.6 | 15.4 | -4.00 | 0.04569 | 14.77 | 0.00187 |
| FUS | 450.8 | 300.0 | -1.50 | 0.00103 | 14.83 | 0.00010 |
| HPN | 196.1 | 109.7 | -1.79 | 0.01887 | 15.92 | 0.00830 |
| FOXO3A | 89.2 | 59.1 | -1.51 | 0.00284 | 16.39 | 0.00858 |
| EHD2 | 44.1 | 26.1 | -1.69 | 0.01074 | 15.27 | 0.00274 |
| IER3 | 284.7 | 137.4 | -2.07 | 0.01939 | 15.68 | 0.02243 |
| SNX1 | 598.5 | 339.3 | -1.76 | 0.00260 | 15.81 | 0.04812 |
| GOLGB1 | 254.8 | 165.2 | -1.54 | 0.00479 | 15.66 | 0.00317 |
| ZNF175 | 75.0 | 46.1 | -1.63 | 0.00225 | 15.95 | 0.04444 |
| IGF2AS | 52.3 | 22.9 | -2.28 | 0.04991 | 15.97 | 0.04085 |
| PHF20 | 143.1 | 94.8 | -1.51 | 0.00306 | 14.96 | 0.00102 |
| CES1 | 154.7 | 75.3 | -2.05 | 0.04815 | 16.15 | 0.03985 |
| GORS2 | 418.2 | 272.2 | -1.54 | 0.00133 | 15.40 | 0.00949 |
| CDK10 | 142.3 | 89.8 | -1.58 | 0.00952 | 14.72 | 0.00066 |
| RFX1 | 25.8 | 16.0 | -1.62 | 0.01539 | 14.93 | 0.00222 |
| GALT | 160.6 | 95.9 | -1.67 | 0.00501 | 15.83 | 0.04761 |
| CYLD | 153.4 | 96.3 | -1.59 | 0.00750 | 15.34 | 0.01079 |
| KLF10 | 323.8 | 178.5 | -1.81 | 0.00860 | 14.69 | 0.00913 |
| UMPS | 193.6 | 128.2 | -1.51 | 0.00311 | 14.99 | 0.00587 |
| ZNF208 | 22.8 | 14.6 | -1.57 | 0.01316 | 15.99 | 0.04344 |
| NEK4 | 100.5 | 66.2 | -1.52 | 0.00852 | 15.38 | 0.01313 |
| ICB1 | 70.9 | 47.1 | -1.51 | 0.02337 | 14.92 | 0.00351 |
| IL1R1 | 218.6 | 135.8 | -1.61 | 0.04093 | 14.74 | 0.01041 |
| PRKAR2A | 179.0 | 116.1 | -1.54 | 0.00735 | 14.58 | 0.01974 |

[a]Model Based Expression Index, dChip software;
[b]Target Sequence prediction score and p-value based on the MicroCosm version 2.0 Web Resource (Sanger Institute);
[c]Genes selected for in vitro analyses

TABLE 5

Predicted miR-346 target genes differentially expressed between FTC and FA

| Gene | FA[a] | FTC[a] | Fold Change | P value | Score[b] | P value |
|---|---|---|---|---|---|---|
| EFEMP2[c] | 338.9 | 120.2 | -2.82 | 0.00000 | 17.49 | 0.02557 |
| DHRS6 | 699.3 | 347.4 | -2.01 | 0.00009 | 16.97 | 0.00660 |
| GALT | 160.6 | 95.9 | -1.67 | 0.00501 | 18.10 | 0.00008 |
| SERHL | 280.4 | 165.4 | -1.70 | 0.00027 | 16.48 | 0.00060 |
| ENTPD1 | 262.7 | 30.7 | -8.56 | 0.00767 | 15.70 | 0.00068 |
| FNTB | 102.7 | 62.6 | -1.64 | 0.00481 | 17.51 | 0.00087 |
| GGTLA1 | 154.6 | 61.9 | -2.50 | 0.00118 | 16.91 | 0.03356 |
| GJA12 | 79.1 | 31.0 | -2.55 | 0.00012 | 15.38 | 0.00893 |
| C21 orf18 | 72.1 | 40.8 | -1.77 | 0.00116 | 15.18 | 0.00053 |
| TSTA 3 | 164.0 | 89.6 | -1.83 | 0.00122 | 16.52 | 0.00829 |
| CFLAR[c] | 295.9 | 194.5 | -1.52 | 0.00261 | 16.60 | 0.00182 |
| SSH3 | 52.2 | 27.4 | -1.90 | 0.00849 | 16.08 | 0.00268 |
| CRELD1 | 246.9 | 163.7 | -1.51 | 0.00247 | 17.31 | 0.00635 |
| INRC5 | 75.7 | 45.5 | -1.66 | 0.00472 | 15.72 | 0.00281 |
| NR2F6 | 81.3 | 40.0 | -2.03 | 0.01936 | 15.84 | 0.00701 |
| CD3Z | 35.2 | 18.2 | -1.93 | 0.00761 | 16.57 | 0.04112 |
| TERF1 | 126.0 | 65.9 | -1.91 | 0.00096 | 15.34 | 0.03542 |
| RXRB | 37.6 | 17.0 | -2.22 | 0.01302 | 15.20 | 0.00310 |
| DGCR2 | 411.8 | 225.4 | -1.83 | 0.00552 | 15.40 | 0.00687 |
| IL11RA | 215.0 | 130.9 | -1.64 | 0.00948 | 15.41 | 0.00009 |
| P1B5PA | 649.2 | 374.5 | -1.73 | 0.00944 | 15.61 | 0.00317 |
| MAPK8IP1 | 61.6 | 36.0 | -1.71 | 0.00351 | 15.29 | 0.02222 |
| THRAP5 | 33.7 | 21.6 | -1.56 | 0.03617 | 17.20 | 0.02810 |
| RFX1 | 25.8 | 16.0 | -1.62 | 0.01539 | 15.56 | 0.02250 |

[a]Model Based Expression Index, dChip software;
[b]Target Sequence prediction score and p-value based on the MicroCosm version 2.0 Web Resource (Sanger Institute);
[c]Genes selected for in vitro analyses

TABLE 6

Predicted miR-192 target genes differentially expressed between FTC and FA

| Gene | FA[a] | FTC[a] | Fold Change | P value | Score[b] | P value |
|---|---|---|---|---|---|---|
| CLIC1 | 885.3 | 560.7 | -1.58 | 0.00091 | 15.43 | 0.04719 |
| PANX1 | 83.8 | 49.3 | -1.70 | 0.00548 | 16.53 | 0.00718 |
| SPARC | 784.8 | 368.5 | -2.13 | 0.00429 | 14.31 | 0.00086 |
| ODC1 | 520.2 | 341.1 | -1.52 | 0.01096 | 15.54 | 0.00045 |
| DDOST | 1257.9 | 722.2 | -1.74 | 0.00106 | 14.53 | 0.00053 |
| ABCG2 | 96.1 | 54.5 | -1.76 | 0.04190 | 15.83 | 0.03715 |
| EGR1 | 1097.7 | 322.2 | -3.41 | 0.00842 | 15.06 | 0.01068 |
| TFG | 503.3 | 292.5 | -1.72 | 0.00111 | 14.92 | 0.00029 |
| DDX3X | 148.7 | 73.4 | -2.03 | 0.00241 | 15.42 | 0.00957 |
| WDR44 | 66.9 | 43.8 | -1.53 | 0.00734 | 14.45 | 0.00330 |
| E2F5 | 59.2 | 32.7 | -1.81 | 0.00902 | 14.70 | 0.00883 |
| LOXL2 | 87.9 | 51.6 | -1.70 | 0.00122 | 15.00 | 0.00660 |
| NP_065789.1 | 331.5 | 166.6 | -1.99 | 0.00009 | 14.28 | 0.00257 |
| XPA | 160.5 | 84.5 | -1.90 | 0.00160 | 16.78 | 0.00531 |
| BARD1 | 47.4 | 25.2 | -1.88 | 0.00668 | 16.29 | 0.02798 |
| RBL2 | 103.0 | 63.8 | -1.61 | 0.00495 | 15.52 | 0.04475 |
| RAB2 | 756.5 | 490.3 | -1.54 | 0.00346 | 19.08 | 0.00011 |
| CUL3 | 534.1 | 338.7 | -1.58 | 0.00008 | 14.27 | 0.00870 |
| MAP3K1 | 28.1 | 16.1 | -1.74 | 0.01657 | 14.69 | 0.04935 |
| PERP | 263.1 | 132.3 | -1.99 | 0.00795 | 14.25 | 0.00894 |
| TP5M1 | 229.4 | 128.4 | -1.79 | 0.00174 | 15.08 | 0.00845 |
| ABCA8 | 231.2 | 84.1 | -2.75 | 0.01449 | 15.35 | 0.04950 |
| ATP10D | 97.5 | 59.1 | -1.65 | 0.00891 | 15.12 | 0.04831 |
| MSN | 1045.7 | 662.2 | -1.58 | 0.00132 | 15.07 | 0.01406 |
| SPFH2 | 217.1 | 134.6 | -1.61 | 0.00212 | 15.25 | 0.00463 |
| ABCC3 | 59.0 | 9.4 | -6.28 | 0.02287 | 15.63 | 0.00204 |
| GRIA1 | 24.3 | 16.2 | -1.50 | 0.03581 | 15.89 | 0.03688 |
| ATXN7 | 111.6 | 65.7 | -1.70 | 0.00034 | 15.44 | 0.04787 |
| TRA1 | 4024.7 | 2291.2 | -1.76 | 0.00016 | 14.41 | 0.00100 |
| RRM1 | 114.5 | 75.1 | -1.53 | 0.00215 | 15.13 | 0.00533 |
| ENTPD3 | 95.6 | 54.5 | -1.75 | 0.02257 | 14.52 | 0.01229 |

TABLE 6-continued

Predicted miR-192 target genes differentially expressed between FTC and FA

| Gene | FA[a] | FTC[a] | Fold Change | P value | Score[b] | P value |
|---|---|---|---|---|---|---|
| B3GALT3 | 53.5 | 33.3 | -1.61 | 0.02072 | 17.95 | 0.01003 |
| BRD3 | 319.9 | 209.2 | -1.53 | 0.02485 | 17.46 | 0.00106 |
| ALC M | 1061.4 | 490.1 | -2.17 | 0.00012 | 14.58 | 0.00070 |
| STX7 | 225.1 | 148.7 | -1.51 | 0.00015 | 14.59 | 0.02461 |
| CD164 | 1605.8 | 1037.5 | -1.55 | 0.00378 | 14.83 | 0.02120 |
| PTP4A3 | 80.3 | 46.1 | -1.74 | 0.02645 | 17.05 | 0.01755 |
| IGSF4 | 1497.6 | 856.5 | -1.75 | 0.00702 | 16.26 | 0.02847 |
| C21 orf18 | 72.1 | 40.8 | -1.77 | 0.00116 | 14.83 | 0.03812 |
| PDE2A | 111.8 | 58.4 | -1.92 | 0.00111 | 14.36 | 0.01510 |
| AKAP9 | 241.5 | 152.5 | -1.58 | 0.00099 | 15.81 | 0.03756 |
| ENOSF1 | 200.2 | 133.1 | -1.50 | 0.01241 | 14.76 | 0.00003 |
| RANBP3 | 46.6 | 27.1 | -1.72 | 0.00693 | 14.54 | 0.00134 |
| GOLGA6 | 57.0 | 37.1 | -1.54 | 0.02277 | 15.12 | 0.01369 |
| RABGAP1 | 440.0 | 219.2 | -2.01 | 0.00009 | 14.28 | 0.00344 |
| NP_00101242 | 1827.9 | 746.0 | -2.45 | 0.00149 | 15.35 | 0.04964 |
| N_001111.2 | 204.0 | 100.0 | -2.04 | 0.00001 | 17.37 | 0.01431 |
| NP_006324.1 | 304.9 | 168.8 | -1.81 | 0.00292 | 16.77 | 0.02081 |
| SEMA4D | 95.3 | 56.3 | -1.69 | 0.00107 | 15.25 | 0.00174 |
| PIK3R4 | 208.1 | 103.3 | -2.02 | 0.00026 | 14.52 | 0.00674 |

[a]MODEL BASED EXPRESSION INDEX, DCHIP SOFTWARE;
[b]TARGET SEQUENCE PREDICTION SCORE AND P-VALUE BASED ON THE MICROCOSM VERSION 2.0 WEB RESOURCE (SANGER INSTITUTE)

Example 2

Detecting PTEN Hamartoma Tumor Syndrome (PHTS) Based on Haplotype Association

Materials and Methods

Study Subjects

A total of 447 unrelated subjects were included in the current analysis. 94 white control subjects, 148 white PHTS patients without detectable germline PTEN mutations (i.e., PTEN mutation negative patients), and 205 white PHTS patients with previously identified germline PTEN mutations/variations (i.e. PTEN mutation/variation positive patients). DNA for control subjects (Utah residents with ancestry from northern and western Europe) was acquired from the Coriell Institute for Medical Research (Camden, N.J.). All PHTS samples were enrolled by referral from centers located throughout the United States, Canada and Europe. Informed consent was acquired for all referred subjects in accordance with procedures approved by the Human Subjects Protection Committees of each respective institution.

Among the PTEN mutation negative patients, 94 were classic CS, 10 patients were classic BRRS, 4 patients exhibited features of both CS and BRRS (termed CS-BRRS overlap), and 39 patients exhibited a CS-like phenotype (i.e., patients with some features of CS, but not meeting operational diagnostic criteria). One PTEN mutation negative patient could not be classified.

The cohort of PTEN mutation/variation positive patients included 103 mutation positive samples (i.e. samples with pathogenic heterozygous missense or nonsense mutations) and 102 variation positive samples. This latter group consists primarily of individuals with identified variants of unknown significance (VUS) located in the PTEN core promoter region or within potential splice donor/acceptor sites. Among the PTEN mutation positive samples, 34 were classic CS, 18 were classic BRRS, 10 exhibited features of CS-BRRS overlap, and 40 were classified as CS-like. One PTEN mutation positive patient could not be classified. The PTEN variation positive samples included 39 patients with classic CS, 2 samples with classic BRRS, 6 samples with both CS and BRRS features, and 52 CS-like samples. Three PTEN variation positive patients could not be classified.

All patients classified as CS in the current study meet operational criteria established by the International Cowden Consortium and curated by the National Comprehensive Cancer Network (Pilarski, R., et al., *J. Med. Genet.*, 41:323-326 (2004)).

SNP Genotyping

SNPs spanning the PTEN locus and located approximately one every 5 kb were selected from the dbSNP database for validation and estimation of minor allele frequency in a 10-sample screening set consisting of 5 white control subjects and 5 white patient samples. 24 screened SNPs were found to have a minor allele frequency$\geq$0.10, and met our criteria for inclusion in this study. To achieve a uniformly spaced SNP map, 6 additional SNPs with a minor allele frequency$\geq$0.10 were identified by DNA resequencing in our screening set. All 30 SNPs were genotyped in our 447 sample cohort. Polymerase chain reactions (PCRs) included 12.5 µl HotStarTaq Master Mix (Qiagen, Valencia, Calif.), 10 mM forward primer, 10 mM reverse primer, and 20 ng of template DNA and used the following thermal cycling conditions: 95° C. for 15 min, 34 cycles of 95° C. for 30 s, 50-58° C. for 45 s, and 72° C. for 1 min, followed by a 72° C. final extension for 10 min. 29 SNPs were genotyped using either restriction fragment length polymorphism (RFLP), SNaPshot (Applied. Biosystems, Foster City, Calif.), or fragment analysis. SNaPshot and fragment analysis products were electorphoresed using an ABI 3730 DNA Analyzer (Applied Biosystems, Foster City, Calif.) and analyzed using GeneMapper v3.5 software (Applied Biosystems, Foster City, Calif.). rs12573787 was genotyped by direct DNA resequencing. Primer sequences and genotyping methodologies are provided in Table 12.

Hemizygous PTEN Deletion Analysis

Real-time quantitative PCR was used to investigate potential micro-deletions in both control (n=4) and PTEN mutation negative patient samples (n=14) where homozygosity was observed for all 30 SNPs. 15 PTEN mutation/variation positive samples were also homozygous for SNPs assayed in this region, however, by virtue of their heterozygous mutations/variations, these samples are assumed to carry two copies of the PTEN allele. Copy number determinations were made for our target gene, PTEN exons 2 and 5, and a control reference gene, GAPDH exon 7. 4 homozygous control samples and 4 homozygous PTEN mutation/variation positive samples were used as negative controls. Additionally, 2 samples previously determined to have PTEN deletions (one spanning the entire PTEN locus, the other spanning both the PTEN and BMPR1A genes) were assayed as positive controls. PCR efficiencies for each amplicon were determined by standard curve analysis using serial dilutions of genomic DNA from a control sample (100 ng, 50 ng, 25 ng, and 12.5 ng, respectively). The calculated PCR efficiencies for these amplicons ranged from 76-81%.

Determination of gene copy number was assayed using 12.5 µl iQ SYBR Green Supermix (Bio-Rad Laboratories, Hercules, Calif.), 10 mM forward primer, 10 mM reverse primer, and 20 ng of template DNA. Thermal cycling conditions comprised of 95° C. for 3 min and 40 cycles at 95° C. for 30 s followed by 58° C. for 30 s and 72° C. for 30 s using an ABI 7700 Sequence Detection System (Applied Biosystems, Foster City, Calif.). Target and reference genes were assayed in triplicate for each sample and subject to meltcurve analysis in order to determine amplicon specificity. The relative quantification of gene copy number for both PTEN amplicons was determined using the comparative delta Ct method ($2^{-\Delta\Delta C_T}$) as described by Livak et al, (Livak, K. J., et al., *Methods,* 25:402-408 (2001)).

Linkage Disequilibrium and Haplotype Analysis

Following assessment of Hardy-Weinberg equilibrium at each polymorphic locus, pairwise LD coefficients (Lewontin's D') were estimated using the LDmax software program and visualized using the GOLD graphical interface (Abecasis, G. R., et al., *Bioinformatics,* 16:182-183 (2000)). D' was calculated and plotted separately for each sample population (control subjects, PTEN mutation negative patients, and PTEN mutation/variation positive patients). LD blocks were determined using data from the control population and the dynamic programming algorithms implemented in the HapBlock software program (Empirical LD method, D'>0.90 for strong LD) (Zhang, K., et al., *Proc. Natl. Acad. Sci. USA,* 99:7335-7339 (2002); Gabriel, S. B., et al., *Science,* 296:2225-2229 (2002)). Following block partitioning, haplotype phase was reconstructed for each block and all genotyped samples using the SNPHap software program, based on pair-wise LD measurements and the expectation-maximization (EM) algorithm, and the PHASE v2.1 software program, based on a Bayesian approach (Clayton, D., et al., *Genet. Epidemiol,* 27:415-428 (2004); Stephens, M., et al., *Am. J. Hum. Genet.,* 68:978-989 (2001)). Additionally, haplotype phase was reconstructed for the extended 30 SNP haplotype for all samples.

Statistical Analysis

Allele and genotype frequencies were computed for each SNP. P-values for Hardy-Weinberg equilibrium (HWE) were obtained and Bonferroni adjustment was applied to control the overall type-I error rate at 0.05. Each patient group (sharing the same mutation status) was compared to the controls in their allele and genotype distributions for each SNP. Following haplotype reconstruction, haplotype from PHASE were selected for comparisons. For each block and the extended block, a number of tests were performed. First, haplotype frequencies in all phenotype groups with distinct mutation statuses were compared using a Pearson $\chi^2$ test, where rare haplotypes (expected frequency less than 5 for any group) were pooled together to make the chi-square approximation accurate as determined by the criterion of Cochran (Cochran, W., *Biometrics,* 10:417-451 (1954)). Bonferroni adjustment were applied to the four overall tests using the significance level of 0.05/4 (0.0125) for each test. Each pair of groups was then compared using a Pearson $\chi^2$ test with the same criterion of pooling rare haplotypes.

If the result of the overall test is statistically significant (P-value<0.0125), the subsequent pairwise tests provide more specific comparisons between groups. The first $\chi^2$ test controls the overall type-1 error rate but further adjustment were made for multiple tests between pairs of groups by using 0.05/6 (0.0083) as the significant level for each such test.

Figure 7:
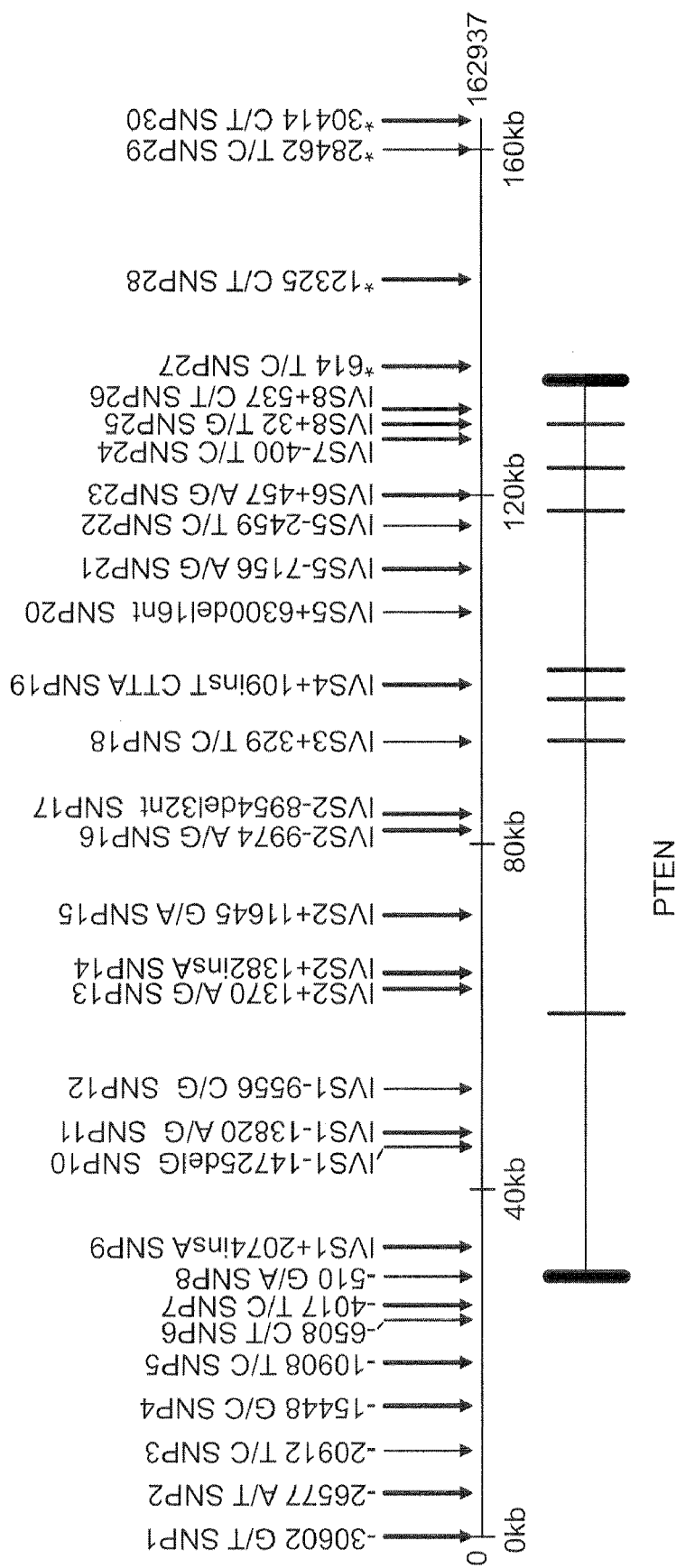
FIG. 7 Schematic diagram of the PTEN locus and SNPs included in the current analysis.
Figure 8:
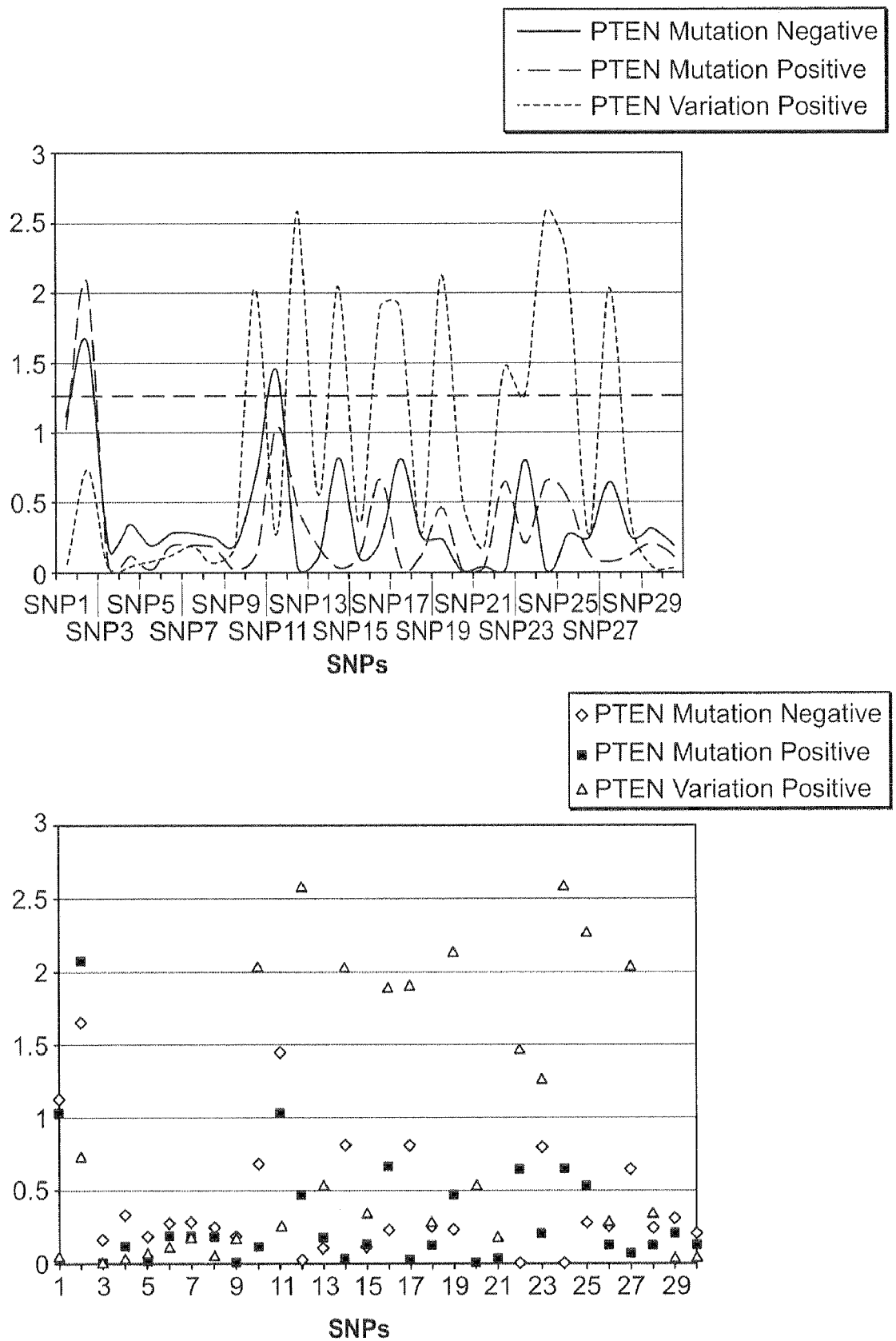
FIG. 8 Summary of SNP Allele Frequency P-Values for PHTS Patient Population Groups Versus Control Population. Allele frequencies among three PHTS patient populations (PTEN mutation negative, PTEN mutation positive and PTEN variation positive) were compared to the control population for all 30 SNPs using a Pearson $\chi^2$ test. −log 10 of the P-values were plotted for each comparison and for all SNPs. Note: −log 10 P-value 1=P-value 0.1, −log 10 P-value 2=value 0.01, and −log 10 P-value 3=P-value 0.001.

Following this, groups with different clinical features were compared in terms of the haplotype frequencies using the same approach of an overall Pearson $\chi^2$ tests and subsequent comparisons of each group (one at a time) with the controls, pooling rare haplotypes in each test as described above. The same set of tests was performed for the controls and the subset of patients classified as mutation positive or mutation negative. Similarly to the first group of test, we use 0.0125 as the significance level for each overall test to adjust for the total number of blocks (4, including 3 haplotype blocks and the extended block), and 0.0125 as the significance level for each subsequent pairwise comparison to adjust for the number of groups being compared with the control group in turn.
Results
SNP Analysis and Identification of Hemizygous Deletions As described herein, an informative marker set comprised of 30 relatively evenly spaced SNPs (one SNP every 5.6 kb, with a minor allele frequency greater than 10%) across a 163 kb region spanning the entire PTEN locus and including 30 kb of flanking sequence was developed (FIG. 7 and Table 7). The majority of identified SNPs are intronic (18/30); 11 are outside of the gene (7 upstream and 4 downstream), and one SNP is located in PTEN's 5' untranslated region (UTR). These include 19 transitions, 5 transversions, and 6 insertion/deletion polymorphisms. Table 8 shows the allele frequencies for all 30 polymorphisms genotyped in the control and PHTS patient populations. No significant departures from HWE were observed. FIG. 8 summarizes the −log 10 P-values from comparisons of allele frequencies among PTEN mutation negative, PTEN mutation positive, and PTEN variation positive groups versus the control population. Overall, results from 13/90 comparisons (14%) were significant at the 0.05 level. Specifically, the allele frequency of SNP2 differed significantly among PTEN mutation positive samples and control samples (P-value=0.0083). More strikingly, the allele frequencies of SNPs 10, 12, 14, 19, 24, 25 and 27 were all significantly different from the control population among the PTEN variation positive group (P-values<0.01). Additionally, SNPs 16 and 17 both achieved statistical significance for this same comparison (P-values=0.0127 and 0.0123, respectively).

Figure 9:
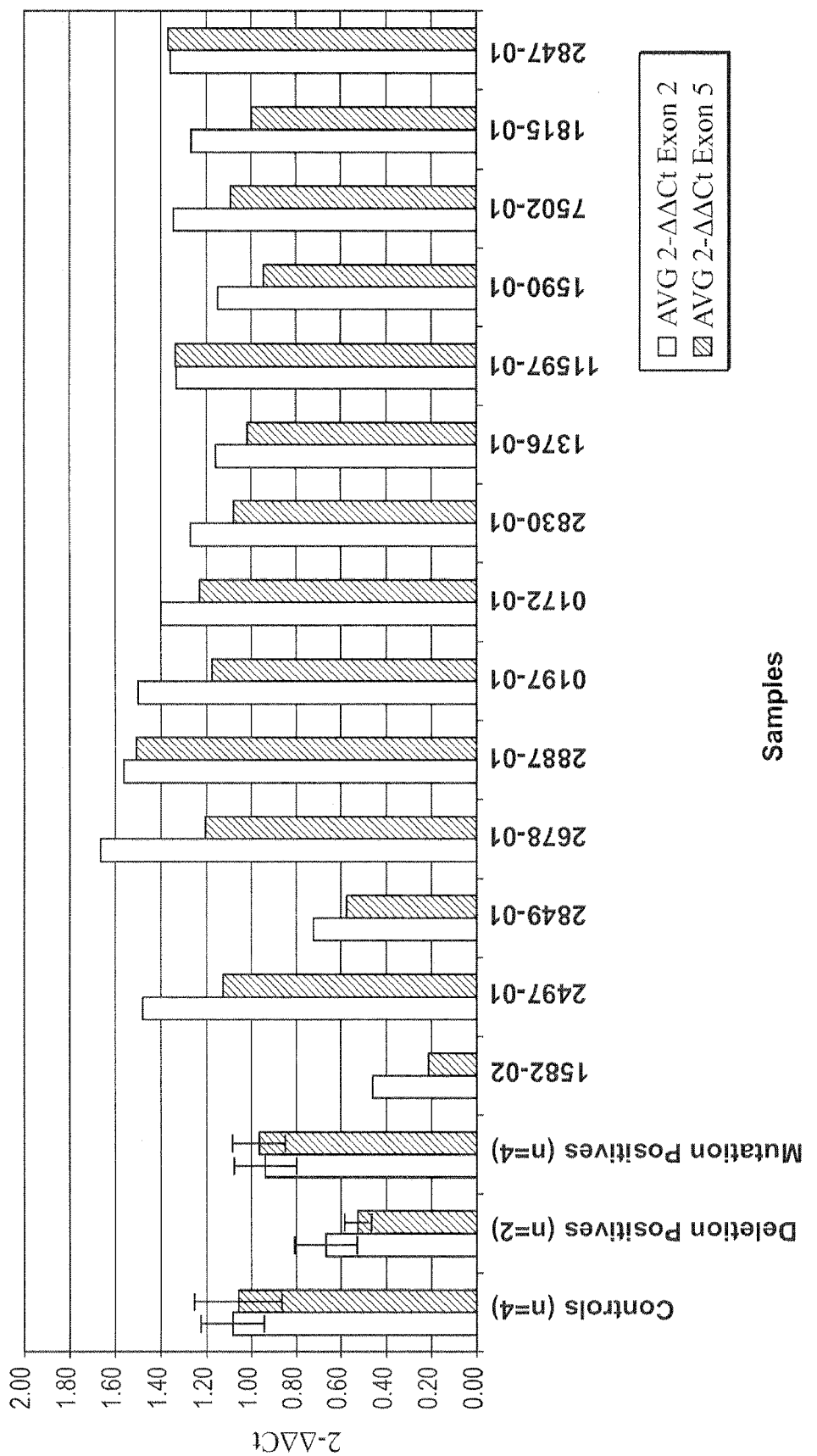
FIG. 9 Hemizygous PTEN Deletion Analysis. PTEN copy number was estimated at exons 2 and 5 using the Livak method for control (n=4), PTEN mutation/variation positive (n=4), and PTEN mutation negative samples (n=14) found to be homozygous for all 30 genotyped SNPs, as well as for known PTEN deletion positive samples (n=2). $2^{-\Delta\Delta Ct}$ values for the control samples ranged from 0.87 to 1.38. PTEN mutation/variation positive samples (known to have heterozygous PTEN mutations/variations) displayed values between 0.75 and 1.13. PTEN deletion positive samples had average $2^{-\Delta\Delta Ct}$ values of 0.67 and 0.53 for exons 2 and 5, respectively. 12 PTEN mutation negative samples had values similar to the control and PTEN mutation positive samples (0.95 to 1.66). 2 PTEN mutation negative samples (1582-02 and 2849-01) displayed $2^{-\Delta\Delta Ct}$ values similar to the PTEN deletion positive samples, ranging from 0.21 to 0.72.
Figures 10A, 10B, 10C:
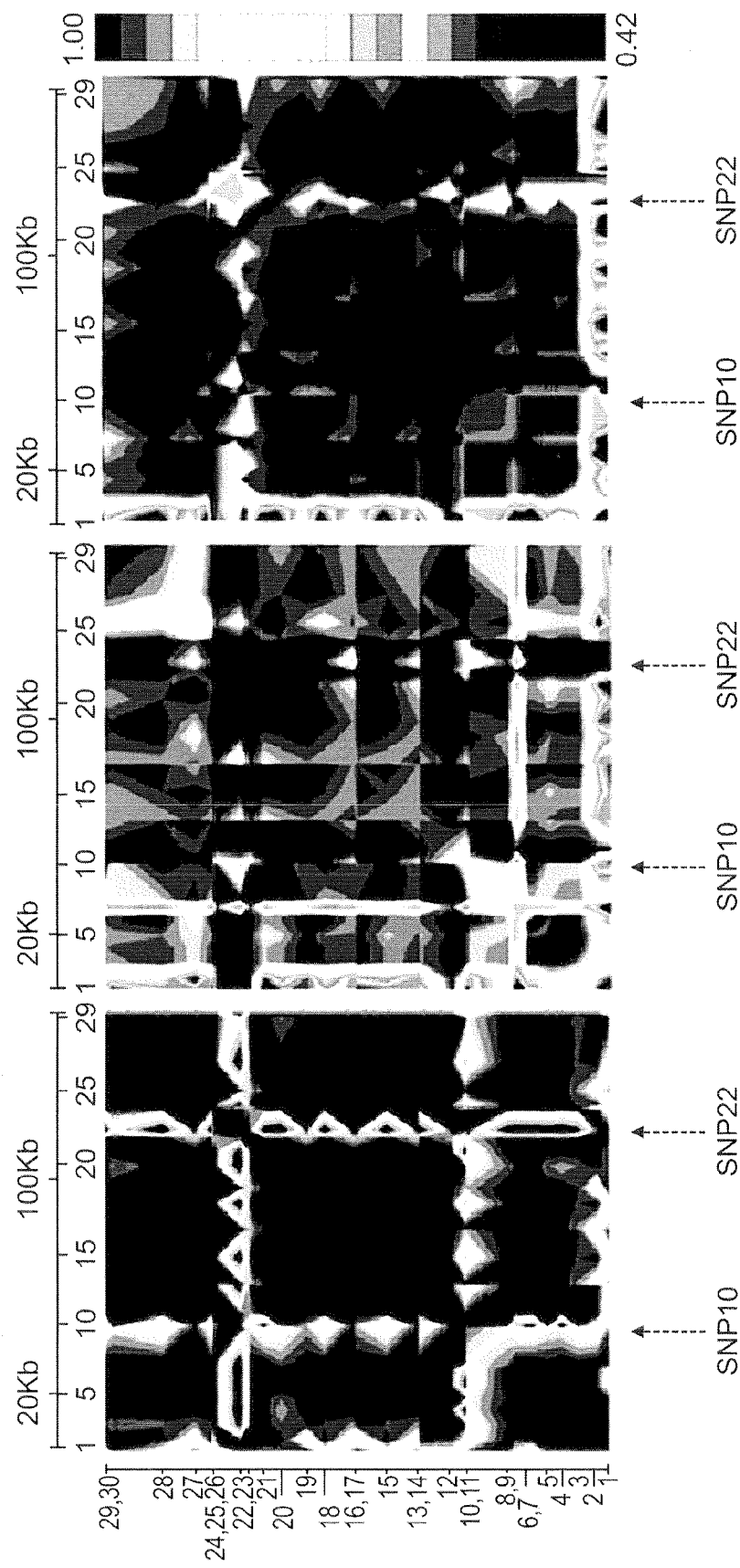
FIGS. 10A-10C GOLD plot of pairwise LD between 30 SNPs. D' values are reported for all three sample groups.

33/447 samples (7.4%) were found to be homozygous for all 30 SNPs in our panel, including: 4/94 control samples (4.3%), 14/148 PTEN mutation negative samples (9.5%), and 15/205 PTEN mutation/variation positive samples (7.3%). Because heterozygosity has previously been identified in the PTEN mutation/variation positive samples, PTEN copy number determinations were only made for the control and PTEN mutation negative samples. Previously we reported that $2^{-\Delta\Delta Ct}$ values close to 1 indicates the presence of two PTEN alleles, while values close to 0.5 are indicative of hemizygous PTEN deletions (Zhou, X. P., et al., *Am. J. Hum. Genet.*, 73:404-411 (2003)). As shown in FIG. 9, the control samples were found to have average $2^{-\Delta\Delta Ct}$ values of 1.09±0.14 for PTEN exon 2 and 1.06±0.20 for PTEN exon 5, confirming that these samples retain two copies of PTEN. Similarly, a subset of PTEN mutation/variation positive samples had average $2^{-\Delta\Delta Ct}$ values of 0.94±0.14 for PTEN exon 2 and 0.97±0.12 for PTEN exon 5. Two samples known to harbor hemizygous germline deletions spanning the entire PTEN locus displayed average values of 0.67 and 0.53 for the two PTEN amplicons, respectively. 12 homozygous PTEN mutation negative samples exhibited $2^{-\Delta\Delta Ct}$ values similar to those observed in the control and PTEN mutation/variation positive samples (1.14-1.66 for PTEN exon 2 and 0.95-1.51 for PTEN exon 5). Two samples, 1582-02 (0.46 for PTEN exon 2 and 0.21 for PTEN exon 5) and 2849-01 (0.72 for PTEN exon 2 and 0.57 for PTEN exon 5) had $2^{-\Delta\Delta Ct}$ values that were consistent with hemizygous deletions. Because of their hemizygous status at this locus, both 1582-02 and 2849-01 were excluded from the subsequent LD and haplotype analyses.
Linkage Disequilibrium Along the PTEN Locus Three distinct haplotype blocks characterized by strong LD in the control population were found (FIG. 10A). Block 1 spans SNP1 (−30602 G/T) to SNP9 (IVS1+2074insA) (33 kb), block 2 spans SNP11 (IVS1−13820 A/G) to SNP21 (IVS5−7156 A/G) (65 kb), and block 3 spans SNP23 (IVS6+457 A/G) to SNP30 (*30414 C/T) (43 kb). Adjacent to each partitioned block, LD decays. SNP10 (IVS1−14725delG) displayed average D' values of 0.75 and 0.85 with blocks 1 and 2, respectively, and could not be assigned to either block. Similarly, SNP22 (IVS5−2459 TIC) had an average D'<0.90 and was not in strong LD with either adjacent block, suggesting that both SNPs lie in/near putative recombination hotspots. The PTEN haplotype structure in two PHTS patient populations (146 unrelated PTEN mutation negative and 205 unrelated PTEN mutation/variation positive PHTS patient samples) are shown in FIGS. 10B and 10C, respectively. Similar to the control population, significant LD was observed for the entire region. However, compared to controls, the overall LD patterns observed in the PHTS patient samples appear to be distinct. LD in these samples suggests less recombination of the adjacent blocks and the presence of extended haplotypes across this locus.
Haplotype Association Analysis at the PTEN Locus Having identified three regions of strong LD flanked by two apparent recombination hot-spots, the haplotypes contained within each LD block were investigated next. Haplotype phase was reconstructed using both the SNPHap and PHASE software programs. The two algorithms performed similarly, agreement was reached for 98.8% of the reconstructed haplotype blocks and for 96.5% of the reconstructed chromosomes (i.e., extended haplotypes) (data not shown). PHASE haplotype blocks and haplotype block frequencies for all chromosomes are shown in Table 9. The number of common haplotypes accounting for >80% of the observed chromosomes varied among the three blocks. We identified 5 common haplotypes for both blocks 1 and 2 and a total of 7 common haplotypes for block 3. For block 3, the number of common haplotypes also varied among sample groups. The haplotype distributions for each block differed significantly among the examined groups (Table 9).

The distribution of the 5 block 1-haplotypes amongst controls, PTEN mutation negative patients, mutation positive patients and variation positive patients was significantly different ($\chi^2$=30.66; P-value=0.0098). Haplotype 1 was found to be under-represented in PTEN mutation negative samples (49.7%) and over-represented in the control population (63.8%). Haplotype 2 was over-represented in PTEN mutation negative and PTEN mutation positive samples compared to both control and PTEN variation positive samples, 18.2% and 16.5% versus 12.2% and 12.3%, respectively. Interestingly, the percentage of low frequency haplotypes was also over-represented among both PTEN mutation negative and PTEN variation positive samples (10.3% and 8.8%, respectively) compared to controls (2.7%).

Statistically significant differences were also observed for the haplotype distributions of blocks 2 and 3 between the examined sample populations ($\chi^2$=45.31 and 62.53, respectively; P-values<0.0001 for both comparisons). For block 2, haplotype 1 was under-represented in both the PTEN mutation negative samples (19.2%) and the PTEN mutation positive samples (21.4%) compared to control subjects (29.3%). Haplotype 2 was the most frequent haplotype among the PTEN variation positive samples (32.4%) and over-represented in this group compared to both the control and PTEN mutation negative samples (15.4% and 16.4%, respectively). The converse was observed for haplotype 4; a 9.8% haplotype frequency was seen in the PTEN variation positive samples compared to 21.3% and 20.2% for the control and PTEN mutation negative samples, respectively.

As observed for block 1, low frequency haplotypes were also over-represented in PHTS samples. These haplotypes were over-represented in both PTEN mutation negative and PTEN mutation positive samples compared to controls for block 2: 8.9% and 9.2% versus 3.7%. For block 3, low frequency haplotypes are only represented in the three PHTS sample groups (2.7% in PTEN mutation negative samples, 2.4% in PTEN mutation positive samples, and 5.4% in PTEN variation positive samples).

Block 3-haplotype 2 was under-represented in PTEN variation positive samples (9.8%) and over-represented in the control (21.3%) and PTEN mutation negative populations (20.5%). As discussed above for block 2-haplotypes 2 and 4 among these same three sample populations, block 3-haplotype 6 also displayed an inverse relationship with block 3-haplotype 2: PTEN variation positive samples (19.1%) compared to the control (6.9%) and PTEN mutation negative (6.5%) samples. This observation suggests that a founder haplotype is formed by the extended haplotype between blocks 2 and 3 (haplotypes 4 and 2, respectively). Furthermore, an extended haplotype may also exist between block 2-haplotype 2 and block 3-haplotype 6, however, the former appears to be associated with more haplotype diversity (see Table 10).

To explore genetic associations pertaining to extended haplotypes, we also reconstructed haplotypes spanning all 30 SNPs (Table 10). 10 extended haplotypes represented 81.9% of all haplotypes observed in our cohort, while 71 additional 'rare' extended haplotypes accounted for the remaining 18.1% (data not shown). Statistically significant differences were observed between the sample populations ($\chi^2$=77.64; P-value=0.0001). Haplotype 2 was observed to be under-represented in both the PTEN mutation negative (8.6%) and PTEN mutation positive (8.7%) samples. This same haplotype was over-represented in the PTEN variation positive samples (18.6%). Haplotype 5 was over-represented in the control population, 13.8%, and under-represented in both the PTEN mutation negative and PTEN variation positive groups, 7.5% and 5.9% respectively. Interestingly, extended haplotype 1, the most frequent haplotype observed in all sampled chromosomes (16.0%), was under-represented in PTEN variation positive samples (9.3%) compared to both control (18.6%) and PTEN mutation negative (19.2%) samples. This haplotype is comprised of block 2-haplotype 4 and block 3-haplotype 2, as well as block 1-haplotype 1 (the most common haplotype observed in this block, 50% in all sample populations). This strongly suggests that, despite the presence of two recombination hot-spots, a founder haplotype likely exists for this region of 10q. Two additional extended haplotypes, 2 and 5, were also observed to be over-represented in the control population (13.3% and 13.8%, respectively) compared to the PTEN mutation negative group (8.6% and 7.5%, respectively). Haplotype 2 was also under-represented in PTEN mutation positive samples (8.7%).

Additionally, as observed for each of the three individual blocks, the frequencies of 'rare' extended haplotypes were different among the different sample populations, accounting for only 12.8% of control chromosomes, compared to 22.6% and 18.6% of PTEN mutation negative and PTEN variation positive chromosomes, respectively. These data suggest that rare alleles may underlie the disease etiology in these sample populations and, more specifically in the case of the PTEN mutation negative group, may harbor pathogenic variant(s) which escaped detection by 'standard' PTEN mutation scanning methodologies.

To examine these associations further, a series of comparative haplotype analyses among PHTS and control samples for haplotype blocks and the extended haplotypes were examined (see Table 11). A significant difference was observed for block 1 between the PTEN mutation negative and control samples ($\chi^2$=18.20; P-value=0.0027) (Table 11). For PTEN variation positive samples, block 2, block 3, and the extended haplotype all differed significantly from the control population ($\chi^2$=22.06; P-value=0.0005; $\chi^2$=37.96; P-value=<0.0001, and $\chi^2$=38.84; P-value=<0.0001, respectively). Notably, the allele frequencies of several individual SNPs comprising these haplotype blocks were significantly different among these same two groups (Table 8 and FIG. 8). A comparison among PTEN mutation negative and PTEN variation positive samples revealed significant differences at these same genomic regions: block 2 ($\chi^2$=28.65; P-value=<0.0001), block 3 ($\chi^2$=39.97; P-value=<0.0001), and the extended haplotype ($\chi^2$=44.13; P-value=<0.0001). In a comparison based on stratification by clinical diagnoses (Table 11), block 2, block 3 and the extended haplotype were also associated with CS-like patients, reaching statistical significance for each of these comparisons ($\chi^2$=18.46; P-value=<0.0024, ($\chi^2$=24.35; P-value=<0.0010, ($\chi^2$=28.02; P-value=<0.0018, respectively). A similar trend was observed for this phenotype when the PTEN mutation negative and PTEN mutation positive groups were combined (block 2: ($\chi^2$=13.60; P-value=<0.0587, block 3: ($\chi^2$=12.61; P-value=<0.0273, and the extended haplotype: ($\chi^2$=21.81; P-value=<0.0095) (Table 11). While interesting, only the comparison of the extended haplotype was statistically significant. Additionally, among PTEN mutation negative and PTEN mutation positive CS patients, block 1 appeared to show an association with this phenotype ($\chi^2$=14.16; P-value=<0.0146), although tis result did not reach statistical significance following Bonferroni adjustment Discussion PHTS represents an assemblage of phenotypically diverse syndromes manifested by germline pathogenic mutations in the PTEN gene. Standard germline mutation scanning has identified causal variants in a majority of patients diagnosed with this complex disorder, particularly for patients diagnosed with CS or BRRS (Eng, C., *Hum. Mutat*, 22:183-198 (2003); Pilarski, R., et al., *J. Med. Genet.*, 41:323-326 (2004)). Despite extensive mutation scanning, however, the etiologic variant(s) have yet to be identified in 15% and 35% of patients with these syndromes, respectively. To investigate genetic associations with PTEN in this subset of patients, as well as to characterize the haplotype architecture of this locus, a case-control haplotype-based approach was utilized.

Similar approaches have been used to examine genetic associations at a growing number of candidate genes (Drysdale, C. M., et al., *Proc. Natl. Acad. Sci. USA.*, 97:10483-10488 (2000); Greenwood, T. A., et al., *Genomics*, 82:511-520 (2003); Yu, C., et al., *Cancer Res.*, 64:7622-7628 (2004)). Haplotype-based approaches are of particular interest as most reports of disease-associated mutations describe variants that directly alter the protein coding sequence of a gene. These studies fail to consider other mechanisms that may alter gene function and, where mutations are not found, may overlook polymorphisms that reside outside of the coding region. Such mechanisms include alterations of gene regulation through the disruption of trans-acting factor(s) and cis-acting sequence element interactions, resulting in a pathologic state (Kleinjan, D. A., et al., *Am. J. Hum. Genet.*, 76:8-32 (2005)).

While the mutation spectrum of PTEN in PHTS has been well studied, its haplotype architecture has not. The extent of LD across this regions has been examined in three previous studies (Haiman, C. A., et al., *Cancer Epidemiol Biomarkers Prev.*, 15:1021-1025 (2006); Hamilton, J. A., et al., *Br. J. Cancer*, 82:1671-1676 (2000); Zhang, L., et al., *Am. J. Med. Genet. B Neuropsychiatr. Genet.*, 141:10-14 (2006)). Hamilton et al. first reported the existence of two distinct four-marker haplotypes in the general population, but found no association with prostate cancer and benign prostatic hyperplasia (Hamilton, J. A., et al., *Br. J. Cancer,* 82:1671-1676 (2000)). A study by Zhang et al. examined the association of this same locus with smoking initiation and nicotine addiction using 5 haplotype tagging SNPs (htSNPs) selected using the SNPbrowser software program (Applied Biosystems, Forster City, Calif.) (Zhang, L., et al., *Am. J. Med. Genet. B Neuropsychiatr. Genet.,* 141:10-14 (2006)). In this study, three haplotype blocks were observed; block 1 spanned 41 kb (from nucleotide position 89,606,485 to 89,647,130), block 2 spanned 16 kb (from nucleotide position 89,679,301 to 89,695,409), and block 3 included a single SNP located at position 89,716,724. As the authors noted, this differed slightly from the PTEN haplotype structure observed by the International HapMap Project. Most recently, Haiman et al. investigated the influence of common variations across this region and the risk of sporadic breast and prostate cancer (Haiman, C. A., et al., *Cancer Epidemiol Biomarkers Prev.,* 15:1021-1025 (2006)). Also employing a htSNP approach, these authors identified 9 common haplotypes representing >87% of all chromosomes across 123 kb of the PTEN locus. Among these common haplotypes, no strong association was found with either sporadic cancer.

For the present study, haplotype phase was reconstructed for samples using the SNPHap software program, based on pair-wise LD measurements and the EM algorithm (Excoffier, L., et al., *Mol. Biol, Evol.,* 12:921-927 (1995); Lewontin, R. C., *Genetics,* 50:757-782 (1964)). Previous studies have demonstrated the appropriateness of the EM algorithm for inferring haplotypes from data obtained from unrelated individuals (Excoffier, L., et al., *Mol. Biol. Evol.,* 12:921-927 (1995); Bonnen, P. E., et al., *Genome Res.,* 12:1846-1853 (2002); Niu, T., et al., *Am. J. Hum. Genet.,* 70:157-169 (2002); Tishkoff, S. A., et al., *Am. J. Hum, Genet.,* 67:518-522 (2000)). Because the analysis described herein relied on statistical inferences of haplotypes from unphased data, this reconstruction was validated using a second algorithm based on a Bayesian approach as implemented in the PHASE software program (Stephens, M., et al., *Am. J. Hum. Genet.,* 68:978-989 (2001); Stephens, M., et al., *Am. J. Hum. Genet.,* 73:1162-1169 (2003)) Although the two programs rely on different mathematical approaches, both algorithms performed remarkably similarly.

The analysis of the LD structure across this region of 10q revealed three distinct haplotype blocks; block 1 spans 33 kb (from nucleotide position 89,583,605 to 89,616,359), block 2 spans 65 kb (from nucleotide position 89,629,942 to 89,694,699), and block 3 spans 43 kb (from nucleotide position 89,702,453 to 89,745,623). Block 2 is flanked by regions of decreased LD, suggesting that SNPs at these sites lie within areas of chromosome recombination. The block partitioning, based on the method by Gabriel et al., partially agreed with that described by Zhang et al. However, based on the data, herein block 1 described by Zhang et al. is actually made up of two distinct blocks. As previously mentioned, these authors defined this region using two htSNPs. To ensure the accurate characterization of this region, it was decided to empirically assess its haplotype architecture using a high-density set of polymorphic markers. Because the extent of LD is variable in this region, the htSNP approach failed to capture all pertinent information regarding the locus in question, specifically regarding the breakdown of LD observed at SNP10 (IVS1–14725delG) and SNP22 (IVS5–2459 T/C). Therefore, a more dense marker set is required. htSNP approaches are capable of capturing most haplotype diversity within a population, i.e., approximately 90% of all chromosomes in a given population (Gabriel, S. B., et al., *Science,* 296:2225-2229 (2002)). However, for uncommon haplotypes, particularly in cases where the causal allele is under-represented, this approach is limited. The finding that 'rare' haplotype blocks account for 2- to 3-fold more PHTS chromosomes compared to control chromosomes and 'rare' extended haplotypes account for nearly 2-fold more PTEN mutation negative and PTEN variation positive chromosomes, indicates that for rare diseases, such as PHTS, low frequency, or 'rare', haplotypes are the ones associated with disease and may harbor pathogenic variants.

Herein, in the effort to characterize the haplotype architecture of the PTEN locus, two PHTS patients, 1582-02 and 2849-01, with hemizygous micro-deletions were identified. Each sample retained only a single copy of the PTEN allele; 1582-02 retained extended haplotype 4 and 2849-01 retained extended haplotype 5. These haplotypes had allele frequencies of 9.9% and 9.2%, respectively, in the entire sample population, resulting in less than a 1% chance of homozygosity for these alleles. By contrast, three of the four homozygous control samples were homozygous for the most frequent haplotype observed in our study. Based on the analysis of microsatellite markers, these deletions span less than approximately 312 kb to 390 kb, respectively (data not shown). Previously, PTEN deletions in only three PHTS patients, all of whom were clinically diagnosed with BRRS or CS/BRRS overlap were identified (Zhou, X. P., et al., *Am. J. Hum. Genet.,* 73:404-411 (2003)). The patients identified in the current study have diagnoses of classic CS (2849-01) and CS-like (1582-02). Implications from these data extend to the clinical realm, indicating that PTEN deletion analysis is warranted in all PHTS patients with CS, BRRS, CS/BRRS, and CS-like phenotypes who lack apparent germline mutations.

Interestingly, one PTEN mutation negative sample was homozygous for a 'rare' extended haplotype with an allele frequency<0.7% in the entire study population. Close inspection of this haplotype revealed that blocks 2 and 3 were relatively common, while block 1 consisted of a low frequency block. This low frequency haplotype block, GACCCTCGI (SEQ ID NO. 19), was only observed in 8 samples; seven PTEN mutation negative samples and one PTEN variation positive sample. Carriers of this allele include 4 CS patients, 3 CS-like patients, and 1 CS/BRRS patient. For the homozygous sample, this indicates that, because of the locations of our amplicons, the deletion analysis may have been unable to detect a possible deletion of the 5' region of this locus. This data implicates the GACCCTCGI (SEQ ID NO. 19) block as a low frequency, highly penetrant PHTS susceptibility allele. Furthermore, all 8 samples have similar 'rare' extended haplotypes; 5 (3 CS and 2 CS-like) share the same haplotype, 1 (CS/BRRS) deviates from this haplotype by a single variation in block 2, and 2 (1 CS and 1 CS-like) are variable for both blocks 2 and 3. Although the SNPs which make up this block and extended haplotype are not causal (based on their frequency in the control population), they are likely in LD with an unknown functional variant conferring disease susceptibility. This further supports the notion that 'rare', low frequency alleles (LD blocks and/or extended haplotypes) may be associated with disease and should therefore be considered as candidate susceptibility alleles in rare disorders.

In addition to an association with rare haplotypes, the analysis of haplotype blocks and extended haplotypes revealed significant differences among the control group and various patient sample populations. The number and frequency of common haplotypes needed to cover >80% of the observed chromosomes varied for each of the three blocks and the extended haplotype. Similar to the association with rare alleles, these data indicate greater haplotype diversity among the PHTS patient populations compared to the control group and are indicative of a higher degree of recombination of the 'ancient haplotype'. Interestingly, the overall LD pattern observed in the patient samples appears to indicate the presence of extended haplotypes. This effect seemed most apparent when PTEN variation positive patients were compared to controls, revealing significant differences between these groups for blocks 2 and 3, as well as for the extended haplotype, and suggesting less recombination among PHTS patients. Furthermore, a pairwise comparisons between groups revealed that the PTEN mutation negative and PTEN mutation positive groups were most similar, suggesting that different pathogenic variants may have arisen from similar haplotypic backgrounds. Taken together, these data indicate that some PHTS patients, i.e., PTEN mutation positive individuals, and perhaps PTEN variation positive individuals, exhibit a haplotype-founder effect, while others, i.e., PTEN mutation negative individuals, harbor rare extended haplotypes which have undergone extensive 'shuffling' of the LD blocks across this region.

Interestingly, among PTEN mutation negative samples, the strongest genetic effect appears to be associated with haplotypes forming block 1 (a block spanning at least 30 kb upstream of PTEN and which includes several kilo-basepairs of the gene's first intron). With the exception of PTEN's core promoter and exon 1, this region has not been well characterized. Screening efforts which have failed to identify mutations/variations at these sites in this group of patients suggest that alterations in this region may have a role in PTEN's regulation. These likely involving novel regulatory elements and contribute to its deregulation.

Various PHTSs, such as BRRS and CS, appear to be caused by the same PTEN mutations, despite clear differences in phenotypic presentation (Eng, C., Hum. Mutat., 22:183-198 (2003)). The R130X mutation in exon 5, for example, occurs in 8 PTEN mutation positive patients included in this study. Among these individuals, 3 have a clinical diagnosis of CS, 2 have a clinical diagnosis of BRRS, and 3 have a clinical diagnosis of CS/BRRS. Both BRRS individuals are carriers of extended haplotypes 3 and 10 and exhibit classic features of BRRS including macrocephaly, lipomas, and pigmented macules of the penis. The probability of this genotype in the general population is <0.3%, suggesting that this infrequent allelic combination likely contributes to their phenotype and that low-penetrant functional variants reside on these loci. Furthermore, although stratification by clinical phenotype was only minimally associated with our haplotypes, correlations from these data become more apparent when the patient's mutation status is considered.

In addition to providing a panel of informative markers for testing genetic associations at the PTEN locus, the data strongly indicate that specific haplotypes along this region are associated with increased PHTS susceptibility. 'PTEN mutation negative' samples lacking traditional mutations in the PTEN coding sequence possess a significantly different haplotype architecture compared to control samples. Along with an association to block 1 of this locus, 'rare' alleles comprise this architecture and may underlie the disease etiology in these patients. Furthermore, haplotype profiles in PHTS patients with known mutations/variations contribute to the phenotypic complexity of this syndrome. Although the mechanisms underlying these relationships have yet to be elucidated, these data indicate that associated chromosomal segments likely harbor variants, potentially involved in the transcriptional regulation of PTEN, which are both pathogenic and/or modifying in nature, the manifest as low-penetrant disease susceptibility alleles.

TABLE 7

Characteristics of 30 SNP panel.

| SNP | dbSNP ID | Position[a] | Variation (major/minor allele) | Minor Allele Frequency[b] | Location[c] |
|---|---|---|---|---|---|
| 1 | rs7085791 | 89,583,605 | G/T | 0.12 | −30602 |
| 2 | rs10887756 | 89,587,630 | A/T | 0.15 | −26577 |
| 3 | rs10887758 | 89,593,295 | T/C | 0.20 | −20912 |
| 4 | rs11202585 | 89,598,759 | G/C | 0.19 | −15448 |
| 5 | ss52090924[d] | 89,603,299 | T/C | 0.20 | −10908 |
| 6 | rs11202590 | 89,607,699 | C/T | 0.14 | −6508 |
| 7 | rs1903860 | 89,610,190 | T/C | 0.13 | −4017 |
| 8 | rs12573787 | 89,613,696 | G/A | 0.14 | −510 |
| 9 | rs3216482 | 89,616,359 | ins/del A | 0.20 | IVS1+2074 |
| 10 | rs11355437 | 89,629,037 | del/ins G | 0.40 | IVS1−14725 |
| 11 | rs2673836 | 89,629,942 | A/G | 0.29 | IVS1−13820 |
| 12 | ss52090925[d] | 89,634,206 | C/G | 0.21 | IVS1−9556 |
| 13 | rs10887763 | 89,645,216 | A/G | 0.14 | IVS2+1370 |
| 14 | rs3831732 | 89,645,229 | ins/del A | 0.39 | IVS2+1382 |
| 15 | rs12569872 | 89,655,492 | G/A | 0.14 | IVS2+11645 |
| 16 | rs1234224 | 89,665,276 | A/G | 0.32 | IVS2−9974 |
| 17 | ss52090926[d] | 89,666,296 | del/ins 32nt | 0.39 | IVS2−8954 |
| 18 | rs10490920 | 89,675,623 | T/C | 0.14 | IVS3+329 |
| 19 | rs3830675 | 89,680,936 | ins/del TCTTA | 0.31 | IVS4+109 |
| 20 | ss52090927[d] | 89,689,289 | del/ins 16nt | 0.15 | IVS5+6300 |
| 21 | rs2299941 | 89,694,699 | A/G | 0.12 | IVS5−7156 |
| 22 | ss52090928[d] | 89,699,396 | T/C | 0.21 | IVS5−2459 |
| 23 | rs2673832 | 89,702,453 | A/G | 0.14 | IVS6+457 |
| 24 | ss52090929[d] | 89,710,231 | T/C | 0.22 | IVS7−400 |
| 25 | rs555895 | 89,710,887 | T/G | 0.31 | IVS8+32 |
| 26 | rs926091 | 89,711,392 | C/T | 0.14 | IVS8+537 |
| 27 | rs701848 | 89,716,725 | T/C | 0.39 | *614 |
| 28 | rs10509532 | 89,727,534 | C/T | 0.14 | *12325 |
| 29 | rs7908337 | 89,743,671 | T/C | 0.24 | *28462 |
| 30 | rs11202614 | 89,745,623 | C/T | 0.14 | *30414 |

[a]SNP position on chromosome 10, Mar. 2006 Human Genome assembly, NCBI Build 36.1, (hg18)
[b]Frequency in control population
[c]Location relative to translation start codon (−), PTEN exons (IVS), or translation stop codon (*)
[d]SNPs identified by DNA resequencing in our screening set

TABLE 8

Summary of SNP allele frequency data for control sample and PHTS patient populations.

| SNP | n | Allele Frequency | | P-value |
|---|---|---|---|---|
| 1 | | G | T | |
| Ctrl | 94 | 0.88 | 0.12 | — |
| Mut− | 146 | 0.81 | 0.19 | 0.0739 |
| Mut+ | 103 | 0.81 | 0.19 | 0.0920 |
| Var+ | 102 | 0.87 | 0.13 | 0.8844 |
| 2 | | A | T | |
| Ctrl | 94 | 0.85 | 0.15 | — |
| Mut− | 146 | 0.76 | 0.24 | 0.0219 |
| Mut+ | 103 | 0.74 | 0.26 | 0.0083 |
| Var+ | 102 | 0.79 | 0.21 | 0.1807 |
| 3 | | T | C | |
| Ctrl | 94 | 0.80 | 0.20 | — |
| Mut− | 146 | 0.78 | 0.22 | 0.6749 |
| Mut+ | 103 | 0.80 | 0.20 | 0.9607 |
| Var+ | 102 | 0.79 | 0.21 | 0.9735 |

TABLE 8-continued

Summary of SNP allele frequency data for control sample and PHTS patient populations.

| SNP | n | Allele Frequency | | P-value |
|---|---|---|---|---|
| 4 | | G | C | |
| Ctrl | 94 | 0.81 | 0.19 | — |
| Mut− | 146 | 0.78 | 0.22 | 0.4491 |
| Mut+ | 103 | 0.80 | 0.20 | 0.7522 |
| Var+ | 102 | 0.82 | 0.18 | 0.9062 |
| 5 | | T | C | |
| Ctrl | 94 | 0.80 | 0.20 | — |
| Mut− | 146 | 0.78 | 0.22 | 0.6368 |
| Mut+ | 103 | 0.80 | 0.20 | 0.9431 |
| Var+ | 102 | 0.79 | 0.21 | 0.8278 |
| 6 | | C | T | |
| Ctrl | 94 | 0.86 | 0.14 | — |
| Mut− | 146 | 0.84 | 0.16 | 0.5202 |
| Mut+ | 103 | 0.84 | 0.16 | 0.6405 |
| Var+ | 102 | 0.88 | 0.12 | 0.7544 |
| 7 | | T | C | |
| Ctrl | 94 | 0.86 | 0.14 | — |
| Mut− | 146 | 0.84 | 0.16 | 0.5202 |
| Mut+ | 103 | 0.84 | 0.16 | 0.6405 |
| Var+ | 102 | 0.88 | 0.12 | 0.6450 |
| 8 | | G | A | |
| Ctrl | 94 | 0.86 | 0.14 | — |
| Mut− | 146 | 0.83 | 0.17 | 0.5615 |
| Mut+ | 103 | 0.83 | 0.17 | 0.6542 |
| Var+ | 102 | 0.87 | 0.13 | 0.8598 |
| 9 | | D | I | |
| Ctrl | 94 | 0.80 | 0.20 | — |
| Mut− | 146 | 0.78 | 0.22 | 0.6368 |
| Mut+ | 103 | 0.80 | 0.20 | 0.9607 |
| Var+ | 102 | 0.78 | 0.22 | 0.6498 |
| 10 | | D | I | |
| Ctrl | 94 | 0.60 | 0.40 | — |
| Mut− | 146 | 0.54 | 0.46 | 0.2033 |
| Mut+ | 103 | 0.62 | 0.38 | 0.7570 |
| Var+ | 102 | 0.73 | 0.27 | 0.0091 |
| 11 | | A | G | |
| Ctrl | 94 | 0.70 | 0.30 | — |
| Mut− | 146 | 0.79 | 0.21 | 0.0351 |
| Mut+ | 103 | 0.78 | 0.22 | 0.0914 |
| Var+ | 102 | 0.74 | 0.26 | 0.5368 |
| 12 | | G | C | |
| Ctrl | 94 | 0.79 | 0.21 | — |
| Mut− | 146 | 0.79 | 0.21 | 0.9388 |
| Mut+ | 103 | 0.83 | 0.17 | 0.3401 |
| Var+ | 102 | 0.90 | 0.10 | 0.0026 |
| 13 | | A | G | |
| Ctrl | 94 | 0.86 | 0.14 | — |
| Mut− | 146 | 0.84 | 0.16 | 0.7762 |
| Mut+ | 103 | 0.83 | 0.17 | 0.6542 |
| Var+ | 102 | 0.90 | 0.10 | 0.2832 |
| 14 | | I | D | |
| Ctrl | 94 | 0.61 | 0.39 | — |
| Mut− | 146 | 0.54 | 0.46 | 0.1526 |
| Mut+ | 103 | 0.62 | 0.38 | 0.9257 |
| Var+ | 102 | 0.74 | 0.26 | 0.0090 |
| 15 | | G | A | |
| Ctrl | 94 | 0.86 | 0.14 | — |
| Mut− | 146 | 0.84 | 0.16 | 0.7762 |
| Mut+ | 103 | 0.84 | 0.16 | 0.7512 |
| Var+ | 102 | 0.89 | 0.11 | 0.445 |
| 16 | | A | G | |
| Ctrl | 94 | 0.69 | 0.31 | — |
| Mut− | 146 | 0.66 | 0.34 | 0.5814 |
| Mut+ | 103 | 0.62 | 0.38 | 0.2137 |
| Var+ | 102 | 0.56 | 0.44 | 0.0127 |
| 17 | | D | I | |
| Ctrl | 94 | 0.61 | 0.39 | — |
| Mut− | 146 | 0.54 | 0.46 | 0.1526 |
| Mut+ | 103 | 0.62 | 0.38 | 0.9257 |
| Var+ | 102 | 0.74 | 0.26 | 0.0123 |
| 18 | | T | C | |
| Ctrl | 94 | 0.86 | 0.14 | — |
| Mut− | 146 | 0.83 | 0.17 | 0.5615 |
| Mut+ | 103 | 0.84 | 0.16 | 0.7512 |
| Var+ | 102 | 0.88 | 0.12 | 0.5397 |
| 19 | | D | I | |
| Ctrl | 94 | 0.69 | 0.31 | — |
| Mut− | 146 | 0.66 | 0.34 | 0.5814 |
| Mut+ | 103 | 0.64 | 0.36 | 0.3446 |
| Var+ | 102 | 0.55 | 0.45 | 0.0073 |
| 20 | | I | D | |
| Ctrl | 94 | 0.85 | 0.15 | — |
| Mut− | 146 | 0.84 | 0.16 | 0.9743 |
| Mut+ | 103 | 0.84 | 0.16 | 0.9815 |
| Var+ | 102 | 0.89 | 0.11 | 0.2885 |
| 21 | | A | G | |
| Ctrl | 94 | 0.87 | 0.13 | — |
| Mut− | 146 | 0.88 | 0.12 | 0.9112 |
| Mut+ | 103 | 0.86 | 0.14 | 0.9259 |
| Var+ | 102 | 0.89 | 0.11 | 0.6513 |
| 22 | | C | T | |
| Ctrl | 94 | 0.79 | 0.21 | — |
| Mut− | 146 | 0.79 | 0.21 | 0.9893 |
| Mut+ | 103 | 0.84 | 0.16 | 0.2256 |
| Var+ | 102 | 0.87 | 0.13 | 0.0340 |
| 23 | | G | A | |
| Ctrl | 94 | 0.86 | 0.14 | — |
| Mut− | 146 | 0.91 | 0.09 | 0.1572 |
| Mut+ | 103 | 0.88 | 0.12 | 0.6188 |
| Var+ | 102 | 0.93 | 0.07 | 0.0538 |
| 24 | | C | T | |
| Ctrl | 94 | 0.79 | 0.21 | — |
| Mut− | 146 | 0.79 | 0.21 | 0.9893 |
| Mut+ | 103 | 0.84 | 0.16 | 0.2256 |
| Var+ | 102 | 0.90 | 0.10 | 0.0026 |

TABLE 8-continued

Summary of SNP allele frequency data for control sample and PHTS patient populations.

| SNP | n | Allele Frequency | | P-value |
|---|---|---|---|---|
| 25 | | T | G | |
| Ctrl | 94 | 0.69 | 0.31 | — |
| Mut− | 146 | 0.65 | 0.35 | 0.5299 |
| Mut+ | 103 | 0.63 | 0.37 | 0.2961 |
| Var+ | 102 | 0.54 | 0.46 | 0.0054 |
| 26 | | C | T | |
| Ctrl | 94 | 0.86 | 0.14 | — |
| Mut− | 146 | 0.83 | 0.17 | 0.5615 |
| Mut+ | 103 | 0.84 | 0.16 | 0.7512 |
| Var+ | 102 | 0.88 | 0.12 | 0.5397 |
| 27 | | T | C | |
| Ctrl | 94 | 0.61 | 0.39 | — |
| Mut− | 146 | 0.55 | 0.45 | 0.2260 |
| Mut+ | 103 | 0.63 | 0.37 | 0.8474 |
| Var+ | 102 | 0.74 | 0.26 | 0.0090 |
| 28 | | C | T | |
| Ctrl | 94 | 0.86 | 0.14 | — |
| Mut− | 146 | 0.83 | 0.17 | 0.5615 |
| Mut+ | 103 | 0.84 | 0.16 | 0.7512 |
| Var+ | 102 | 0.89 | 0.11 | 0.4450 |
| 29 | | T | C | |
| Ctrl | 94 | 0.76 | 0.24 | — |
| Mut− | 146 | 0.72 | 0.28 | 0.4920 |
| Mut+ | 103 | 0.73 | 0.27 | 0.6173 |
| Var+ | 102 | 0.75 | 0.25 | 0.9071 |
| 30 | | C | T | |
| Ctrl | 94 | 0.86 | 0.14 | — |
| Mut− | 146 | 0.84 | 0.16 | 0.6292 |
| Mut+ | 103 | 0.84 | 0.16 | 0.7512 |
| Var+ | 102 | 0.85 | 0.15 | 0.9282 |

TABLE 9

Haplotype blocks across the PTEN locus.

A.

| Block 1 Haplotypes | Controls (n = 188)[a] | PTEN Mutation − (n = 292)[a] | PTEN Mutation + (n = 206)[a] | PTEN Variation + (n = 204)[a] |
|---|---|---|---|---|
| 1 GATGTCTGD (SEQ ID NO. 20) | 0.638 | 0.497 | 0.549 | 0.559 |
| 2 TTTGTCTGD (SEQ ID NO. 21) | 0.122 | 0.182 | 0.165 | 0.123 |
| 3 GACCCTCAI (SEQ ID NO. 22) | 0.138 | 0.120 | 0.141 | 0.108 |
| 4 GTTGTCTGD (SEQ ID NO. 23) | 0.027 | 0.055 | 0.073 | 0.074 |
| 5 GACCCCTGI (SEQ ID NO. 19) | 0.048 | 0.045 | 0.044 | 0.049 |
| Low Frequency | 0.027 | 0.103 | 0.029 | 0.088 |
| $\chi^2$ statistic | 30.66 | | | |
| P-value | 0.0098 | | | |

B.

| Block 2 Haplotypes | Controls (n = 188)[a] | PTEN Mutation − (n = 292)[a] | PTEN Mutation + (n = 206)[a] | PTEN Variation + (n = 204)[a] |
|---|---|---|---|---|
| 1 GCADGAITDIA (SEQ ID NO. 24) | 0.293 | 0.192 | 0.214 | 0.255 |
| 2 ACADGGITIIA (SEQ ID NO. 25) | 0.154 | 0.164 | 0.199 | 0.324 |
| 3 ACAIGADTDIA (SEQ ID NO. 26) | 0.176 | 0.240 | 0.204 | 0.162 |
| 4 AGAIGADTDIA (SEQ ID NO. 27) | 0.213 | 0.202 | 0.165 | 0.098 |
| 5 ACGDAGICIDG (SEQ ID NO. 28) | 0.128 | 0.113 | 0.126 | 0.103 |

TABLE 9-continued

Haplotype blocks across the PTEN locus.

| | | | | |
|---|---|---|---|---|
| Low Frequency | 0.037 | 0.089 | 0.092 | 0.059 |
| $\chi^2$ statistic | 45.31 | | | |
| P-value | <0.0001 | | | |

C.

| Block 3 Haplotypes | Controls (n = 188)[a] | PTEN Mutation − (n = 292)[a] | PTEN Mutation + (n = 206)[a] | PTEN Variation + (n = 204)[a] |
|---|---|---|---|---|
| 1 ATTCCCTC (SEQ ID NO. 29) | 0.176 | 0.226 | 0.214 | 0.157 |
| 2 ACTCCCTC (SEQ ID NO. 30) | 0.213 | 0.205 | 0.160 | 0.098 |
| 3 ATTCTCTC (SEQ ID NO. 31) | 0.160 | 0.123 | 0.136 | 0.216 |
| 4 ATGTTTCT (SEQ ID NO. 32) | 0.144 | 0.154 | 0.150 | 0.098 |
| 5 ATGCTCTC (SEQ ID NO. 33) | 0.101 | 0.110 | 0.107 | 0.118 |
| 6 ATGCTCTC (SEQ ID NO. 34) | 0.069 | 0.065 | 0.097 | 0.191 |
| 7 GTTCTCTC (SEQ ID NO. 35) | 0.138 | 0.089 | 0.117 | 0.069 |
| Low Frequency | 0.000 | 0.027 | 0.024 | 0.054 |
| $\chi^2$ statistic | 62.53 | | | |
| P-value | <0.0001 | | | |

[a] n = Number of Haplotypes

TABLE 10

Extended haplotypes for all 30 SNPs across the PTEN locus.

| PTEN Extended Haplotypes | Total (n = 890)[a] | Controls (n = 188)[a] | PTEN Mutation − (n = 292)[a] | PTEN Mutation + (n = 206)[a] | PTEN Variation + (n = 204)[a] |
|---|---|---|---|---|---|
| 1 GATGTCTGDDAGAIGADTDIACACTCCCTC (SEQ ID NO. 36) | 0.160 | 0.186 | 0.192 | 0.155 | 0.093 |
| 2 GATGTCTGDIGCADGAITDIATATTCTCTC (SEQ ID NO. 37) | 0.119 | 0.133 | 0.086 | 0.087 | 0.186 |
| 3 TTTGTCTGDDACAIGADTDIATATTCCCTC (SEQ ID NO. 38) | 0.113 | 0.101 | 0.137 | 0.121 | 0.083 |
| 4 GACCCTCAIIACGDAGICIDGTATGTTTCT (SEQ ID NO. 39) | 0.099 | 0.117 | 0.082 | 0.117 | 0.088 |
| 5 GATGTCTGDIGCADGAITDIATGTTCTCTC (SEQ ID NO. 40) | 0.092 | 0.138 | 0.075 | 0.107 | 0.059 |
| 6 GATGTCTGDIACADGGITIIATATGCTCTC (SEQ ID NO. 41) | 0.064 | 0.027 | 0.031 | 0.073 | 0.137 |
| 7 GATGTCTGDIACADGGITIIATATGCTCTC (SEQ ID NO. 42) | 0.054 | 0.048 | 0.055 | 0.063 | 0.049 |
| 8 GACCCCTGIIACADGGITIIATATGCTCCC (SEQ ID NO. 43) | 0.044 | 0.048 | 0.038 | 0.044 | 0.049 |
| 9 GATGTCTGDDACAIGADTDIATATTCCCTC (SEQ ID NO. 44) | 0.039 | 0.059 | 0.048 | 0.029 | 0.020 |

TABLE 10-continued

Extended haplotypes for all 30 SNPs across the PTEN locus.

| PTEN Extended Haplotypes | Total (n = 890)[a] | Controls (n = 188)[a] | PTEN Mutation −(n = 292)[a] | PTEN −Mutation (n = 206)[a] | PTEN +Variation + (n = 204)[a] |
|---|---|---|---|---|---|
| 10 GTTGTCTGDDACAIGADTDIATATTCCCTC (SEQ ID NO. 45) | 0.035 | 0.016 | 0.031 | 0.044 | 0.049 |
| Low Frequency | 0.181 | 0.128 | 0.226 | 0.16 | 0.186 |
| $\chi^2$ statistic | 77.64 | | | | |
| P-value | <0.0001 | | | | |

[a] n = Number of Haplotypes

TABLES 11

Comparative Haplotype Analysis.

| Comparison | Block 1 $\chi^2$ statistic | Block 1 P-value | Block 2 $\chi^2$ statistic | Block 2 P-value | Block 3 $\chi^2$ statistic | Block 3 P-value | Extended Haplotype $\chi^2$ statistic | Extended Haplotype P-value |
|---|---|---|---|---|---|---|---|---|
| PTEN Mutation − vs. Ctrl | 18.20 | 0.0027 | 12.03 | 0.0614 | 10.44 | 0.1649 | 17.27 | 0.0447 |
| PTEN Mutation + vs. Ctrl | 6.78 | 0.2376 | 9.66 | 0.0854 | 8.67 | 0.2771 | 13.34 | 0.2054 |
| PTEN Variation + vs. Ctrl | 12.34 | 0.0304 | 22.06 | 0.0005 | 37.96 | <0.0001 | 38.84 | <0.0001 |
| PTEN Mutation − vs. PTEN Mutation + | 10.91 | 0.0531 | 3.41 | 0.7566 | 3.83 | 0.7987 | 13.05 | 0.2899 |
| PTEN Mutation − vs. PTEN Variation + | 5.02 | 0.5415 | 28.65 | <0.0001 | 39.97 | <0.0001 | 44.13 | <0.0001 |
| PTEN Mutation + vs. PTEN Variation + | 8.38 | 0.1364 | 13.82 | 0.0318 | 21.65 | 0.0029 | 20.31 | 0.0161 |
| Clinical Features: Overall | 9.32 | 0.3162 | 29.76 | 0.0193 | 26.42 | 0.0484 | 7.98 | 0.0924 |
| CS vs. Ctrl | 12.36 | 0.0302 | 7.61 | 0.1788 | 10.08 | 0.1841 | 15.51 | 0.1147 |
| BRRS vs. Ctrl | 1.57 | 0.6667 | 9.87 | 0.0789 | 10.03 | 0.1233 | 5.07 | 0.4065 |
| CS/BRRS vs. Ctrl | 1.87 | 0.3932 | 9.19 | 0.0564 | 1.31 | 0.8600 | 0.49 | 0.4825 |
| CS-like vs. Ctrl | 12.94 | 0.0240 | 18.46 | 0.0024 | 24.35 | 0.0010 | 28.02 | 0.0018 |
| PTEN Mut. − and + Clinical Features: Overall | 8.82 | 0.0659 | 13.41 | 0.0984 | 23.70 | 0.0220 | 3.58 | 0.4700 |
| PTEN Mut. − and + CS vs. Ctrl | 14.16 | 0.0146 | 12.40 | 0.0883 | 10.12 | 0.0720 | 11.98 | 0.1519 |
| PTEN Mut. − and + BRRS vs. Ctrl | 0.96 | 0.8107 | 9.04 | 0.1715 | 9.02 | 0.1083 | 4.11 | 0.5339 |
| PTEN Mut. − and + CS/BRRS vs. Ctrl | 1.70 | 0.4027 | 0.04 | 0.8415 | 4.32 | 0.1155 | 0.29 | 0.5890 |
| PTEN Mut. − and + CS-like vs. Ctrl | 11.35 | 0.0449 | 13.60 | 0.0587 | 12.61 | 0.0273 | 21.81 | 0.0095 |

Note:
PHTS patients were stratified based on their PTEN mutation status and compared to controls, as well as each other. The Bonferroni-adjusted nominal significance level used for this comparison was P-value <0.0083. Significant results are indicated in bold.

Note:
An overall Comparison was made based on stratification of clinical features followed by comparisons based on clinical diagnoses (CS, BRRS, CS/BRRS, or CS-like) for all patient samples, irrespective of their mutation status, and compared to controls. The Bonferroni-adjusted nominal significance level used for this comparison was P-value <0.0125. Significant results are indicated in bold.

Note:
Overall comparisons of patient clinical diagnoses among PTEN mutation negative and PTEN mutation positive samples were performed followed by comparisons made among this group versus control samples based on patient clinical diagnosis. The Bonferroni-adjusted nominal significance level used for this comparison was P-value <0.0125. Significant results are indicated in bold.

SUPPLEMENTAL TABLE 1

Primer sequences and genotyping methodologies for all SNP and quantitative real-time PCR reactions

| SNP | Forward Primer | Reverse Primer | Genotyping Methodology |
|---|---|---|---|
| 1 | GATAGAGTCTTGCTCTGTAG (SEQ ID NO. 46) | ACCATACAATATCTGCCTTG (SEQ ID NO. 47) | SNaPshot |
|  | SBE primer: tgccacgtcgtgaaagtctgacaaGAGTAGCTGGGACTACAG (SEQ ID NO. 48) | | |
| 2 | GCTGTGGTATGTACTTTCTG (SEQ ID NO. 49) | ATGCATGAAACAGCTACTTG (SEQ ID NO. 50) | RFLP(BanI) |
| 3 | TAAGTGGATCATGCCTGTAG (SEQ ID NO. 51) | CTTAATGGATGCAGACTCAG (SEQ ID NO. 52) | RFLP (BsiIIKAI) |
| 4 | CATTCTCAAGCAGGACTCAG (SEQ ID NO. 53) | AATCCACCTGCTTCAGCTTC (SEQ ID NO. 54) | RFLP (HincII) |
| 5 | ACTGCAACTTTGACCTCCTG (SEQ ID NO. 55) | GCAGAATCTCACTCTGTCAG (SEQ ID NO. 56) | RFLP(DpnII) |
| 6 | GCTGTGGTTGCTCATCATTC (SEQ ID NO. 57) | CAATAGGAAGATACCCTGAC (SEQ ID NO. 58) | RFLP (AciI) |
| 7 | CCTGATGTTTAGACAAGCAG (SEQ ID NO. 59) | CTTAGATTGCTGATCTTGTCTCC (SEQ ID NO. 60) | RFLP(BfaI) |
| 8 | ACTGGGCATGCTCAGTAGAG (SEQ ID NO. 61) | AGACCAACTCTCCGGCGTTC (SEQ ID NO. 62) | DNA resequencing |
| 9 | TTACTAAGGCTAAACTGGAC (SEQ ID NO. 63) | /FAM/-gcgaatcGTCATGTCACAGCTCACATG (SEQ ID NO. 64) | Fragment Analysis |
| 10 | GGATCACAGATGTAGGCTTG (SEQ ID NO. 65) | /FAM/-catcgccTAGCTGAGAGTGTACTAGAC (SEQ ID NO. 66) | Fragment Analysis |
| 11 | AGTTGAGAAGTCTAGTACAC (SEQ ID NO. 67) | ATCCTGTAATCCCACTCTAG (SEQ ID NO. 68) | SNaPshot |
|  | SBE primer: atcgagatcgacccacaatccactggtcCTATAGTTGTGAATATGTTTAT (SEQ ID NO. 69) | | |
| 12 | GCAAGATAGCTAGTACCATG (SEQ ID NO. 70) | AATGCCATATGCTAGCACAG (SEQ ID NO. 71) | RFLP (MboII) |
| 13 | AGGAATTCATGTCTGATGTG (SEQ ID NO. 72) | GTGACTGTACTGCTCACTTC (SEQ ID NO. 73) | SNaPshot |
|  | SBE primer: gtgcAATCAATTTTTGTACCTACAAA (SEQ ID NO. 74) | | |
| 14 | /HEX/-cgtccgaCATTATGCAGATGTAGACTC (SEQ ID NO. 75) | TAAACAGTCCTTCTGGCATC (SEQ ID NO. 76) | Fragment Analysis |
| 15 | TAGCATATTCTGACTCCTTC (SEQ ID NO. 77) | GATTAGCCCAAGAGTTGTAC (SEQ ID NO. 78) | SNaPshot |
|  | SBE primer: agtcttcgagatccagccatcatcgactggtcAGTGCTGGGATTATAGGC (SEQ ID NO. 79) | | |
| 16 | TGTAACCTGCAGGAGGCATC (SEQ ID NO. 80) | AAAGCAGAGAGGTAATACTC (SEQ ID NO. 81) | SNaPshot |
|  | SBE primer: attacgtaGACTACGACCCAGGTAGG (SEQ ID NO. 82) | | |
| 17 | ACAGTTGTTCACAGTGGTAG (SEQ ID NO. 83) | /FAM/-gtaccgtTCCTAAGCAGATTGCTCCTG (SEQ ID NO. 84) | Fragment Analysis |
| 18 | TGCTTGTTAGAGTGAGGTAG (SEQ ID NO. 85) | CTAGCTCTATCAATCAGGTG (SEQ ID NO. 86) | RFLP (NcoI) |

SUPPLEMENTAL TABLE 1-continued

Primer sequences and genotyping methodologies for all SNP and quantitative real-time PCR reactions

| SNP | Forward Primer | Reverse Primer | Genotyping Methodology |
|---|---|---|---|
| 19 | AGGTAGGTATGAATGTACTG (SEQ ID NO. 87) | /HEX/ agtcgatATCAGACTCCTCTTATCAAC (SEQ ID NO. 88) | Fragment Analysis |
| 20 | ACTGCAACCTCTACCTCCTG (SEQ ID NO. 89) | /FAM/- cgtccgcAGCTCAATGAACTCATGTAC (SEQ ID NO. 90) | Fragment Analysis |
| 21 | GCAACTGAATAGATGCGTAG (SEQ ID NO. 91) SBE primer: cttaatccgtagtcaCCATTACTTCACCTCATCT (SEQ ID NO. 93) | ATAACTAACACCATCGTCAC (SEQ ID NO. 92) | 26 SNaPshot |
| 22 | GGTACACTACTAATCACTTG (SEQ ID NO. 94) | TCACCGTGTTAGCCAGGATG (SEQ ID NO. 95) | RFLP (DraI) |
| 23 | GGAAGACTAGGTATTGACAG (SEQ ID NO. 96) | AAAGAGCATCAATGAGACTC (SEQ ID NO. 97) | RFLP (NlaIII) |
| 24 | AGAAACTGGAGCTTCTCATG (SEQ ID NO. 98) | AAGGCAATCTGAGTTATCTG (SEQ ID NO. 99) | RFLP (HpyCH4IV) |
| 25 | AAGACAAAGCCAACCGATACTT (SEQ ID NO. 100) | GGAAAGACTAGAAGAGGCAGAAGC (SEQ ID NO. 101) | RFLP (HincII) |
| 26 | Same as SNP25 | Same as SNP25 | RFLP (BsaXI) |
| 27 | CATAATACCTGCTGTGGATG (SEQ ID NO. 102) SBE primer: aagctaggtgccacgacgagatagtctgagaaCCGAGTTGGGACTAGGGC (SEQ ID NO. 104) | TCAGACCACAGCTAGTGAAC (SEQ ID NO. 103) | SNaPshot |
| 28 | ATTGCTTCGCTCACCTGCTC (SEQ ID NO. 105) | CCTTTGAGATCCTCAGTAAG (SEQ ID NO. 106) | RFLP (HpyCH4IV) |
| 29 | TAATTCTGGAGCTTCCTGAG (SEQ ID NO. 107) SBE primer: atctagatccacccatactccgactatcAGGCTGAGGCATGAGAAT (SEQ ID NO. 109) | CTGACTCTATACTCTGTGAG (SEQ ID NO. 108) | SNaPshot |
| 30 | TTGGCTACAAATGTCTCTAG (SEQ ID NO. 110) | GGTGCTGCTGTTTACTGAG (SEQ ID NO. 111) | RFLP (Bsu36 I) |
| Quantitative Real-time PCR Primers | | | |
| GAPDH exon 7 | GTATCGTGGAAGGACTCATG (SEQ ID NO. 112) | GGAAATTATGGGAAAGCCAG (SEQ ID NO. 113) | |
| PTEN exon 2 | GTTTGATTGCTGCATATTTCAG (SEQ ID NO. 114) | CCTGTATACGCCTTCAAGTC (SEQ ID NO. 115) | |
| PTEN exon 5 | CGAACTGGTGTAATGATATG (SEQ ID NO. 116) | TCCAGGAAGAGGAAAGGAAA (SEQ ID NO. 117) | |

SBE Primer = Single base extension primer used in SNaPshot assay.
Lower-case indicates non-homologous tail.

Example 3

Targets for Use in Prognosis and Therapy of Head and Neck Squamous Cell Carcinomas (HNSCC)

Methods
HNSCC Samples

A total of 122 consecutively obtained formalin-fixed, paraffin-embedded, primary squamous cell carcinomas of the head and neck (HNSCC) from 122 patients, who have not been previously treated and who had not been on a clinical trial, have been analyzed in this study (Table 13). Of these, 63 (53.4%) were pharyngeal carcinoma and 55 (46.6%) were oral squamous cell carcinoma (mainly lingual carcinomas). In addition, 1 laryngeal cancer and 2 carcinomas of unknown primary were analyzed. Among the pharyngeal SCC, 38.1% (n=24) were located in the oro-pharynx and the remaining (n=39) in the hypo-pharynx. The distribution according to pTNM classification was as follows: 20.9% T1, 40% T2, 17.27% T3 and 21.8% T4, which is similar to that obtained for all corners at academic institutions. The clinical staging followed the guidelines by the American Joint Committee of Cancer (6th edition) (Table 13). The study, which utilized anonymized unlinked samples, was approved, under exempt status, by the participating institutional Review Boards for Human Subjects' Protection. Examination of Cancer Registry information revealed that the subjects happened to have been smokers.

LCM and DNA Extraction

Laser capture microdissection (LCM) was performed using the Arcturus PixCell II microscope (Arcturus Engineering Inc., Mountain View, Calif.) in order to isolate the two compartments of the neoplastic tissue (epithelium and stroma) separately (FIGS. 11A, 11B) (Fukino, K., et al., Cancer Res., 64:7231-7236 (2004)). Specifically captured were stromal fibroblasts adjacent to malignant epithelium (i.e., the tumor stroma) under direct microscopic observation. These stromal fibroblasts resided either in between aggregations of epithelial tumor cells or no more than 0.5 cm distant from a tumor nodule. Corresponding normal DNA for each case was procured from normal tissue (preferentially tumor negative lymph node), obtained from a different tissue block containing only normal tissue.

Genome Wide Loss of Heterozygosity/Allelic Imbalance (LOH/AI) Scan

Genomic DNA was extracted as previously described by us in detail (Weber, F., et al., Am. J. Hum. Genet. J., 78(6):961-72 (2006); Fukino, K., et al., Cancer Res., 64:7231-7236 (2004)). Polymerase chain reaction (PCR) was performed using DNA from each compartment (normal control, tumor epithelium and tumor stroma) of each sample and one of 72 multiplex primer panels, which comprises 366 fluorescent labeled microsatellite markers. Genomic location is based on the MapPairs® genome-wide Human Markers set (version 10) (Invitrogen, CA) developed at the Marshfield Institute. This whole genome panel has an average 16.2 markers per chromosome (ranging from 7 to 29 markers per chromosome) or approximately a 9cM inter-marker distance. Genotyping was performed with the ABI 377×1 or 3700 semi-automated sequencer (Applied Biosystems, Perkin-Elmer Corp., Norwalk, Conn.). The results were analyzed by automated fluorescence detection using the GeneScan collection and analysis software (GeneScan, ABI). Scoring of LOH/AI was performed by manual inspection of the GeneScan output (FIG. 11C). A ratio of peak heights of alleles between germline and somatic DNA$\geq$1.5 was used to define LOH/AI as previously described by us and others (Weber, F., et al., Am. J. Hum. Genet. J., 78(6):961-72 (2006); Marsh, D. J., et al., Cancer Res., 57:500-503 (1997); Nelson, H. H., et al., Carcinogenesis, 26:1770-1773 (2005); Dacic, S., et al., Am. J. Surg. Pathol., 29:897-902 (2005)). As described previously, the methodological veracity of LOH/AI using Multiplex-PCR on archived tissue was extensively validated (Weber, F., et al., Am. J. Hum. Genet. J., 78(6):961-72 (2006); Fukino, K., et al., Cancer Res., 64:7231-7236 (2004)).

Statistical Analysis

In total, 366 microsatellite markers were analyzed in both epithelium and stroma samples from the 122 patients. First, regional LOH "hot-spots", defined as a significantly higher frequency of LOH at a marker or markers compared to other markers along the same chromosome, were determined. Towards those ends, for each marker, the statistical significance of overall (across all samples) LOH frequency compared to the chromosome average was analyzed using the exact test of binomial proportions (R base package binom.test.; http://www.r-project.org). Second, the association of LOH/ROH in epithelium and stroma samples with presenting clinico-pathologic parameters such as location, pT, pN, grade, clinical stage, age and sex, were analyzed using a binomial model with nested structures (McCullagh, P., et al., Generalized Linear Models: Chapman and Hall; 1983; Faraway, J. J., Extending Linear Models with R: Generalized Linear, Mixed Effects and Nonparametric Regression Models: Chapman and Hall; 2006). Of note, the age was dichotomized into 2 classes using age of 40 years as the cutoff. For associations with clinical stage, pT or pN, the statistical significance was tested using the test of trend for multiple proportions. Multiple testing adjustment has been applied by using False Positive Report Probability (FPRP) (Wacholder, S., et al., J. Natl. Cancer Inst., 96:434-42 (2004)) with a prior probability of 0.05 and 0.01, denoted as $FPRP_{0.05}$ and $FPRP_{0.01}$, respectively. FPRP indicates the probability that a statistically significant finding is a false-positive by considering three factors: the p-value magnitude, the statistical power, and the prior probability of true associations. Only those with p-values<0.05 and estimated FPRP values less than 50% (or P<0.5), indicating a small probability of being a false positive, are reported as statistically significant findings. For example, a significant value with a prior probability of 0.01 and an FPRP value less than 50% is denoted $FPRP_{0.01}<0.5$. The hierarchical clustering and pattern visualization were performed using PfCluster (Xu, Y., et al., PfCluster: a new cluster analysis procedure for gene expression profiles. Paper presented at: A Conference on Nonparametric Inference and Probability with Applications to Science (Honoring Michael Woodroofe), Ann Arbor, Mich., 2005). The R package (http://www.r-project.org) was used for the data mining and statistical analysis.

Results

The study described herein included predominantly (97.5%) squamous cell carcinoma (SCC) of the oral cavity and pharynx of patients with a history of smoking. Overall, 244 test samples (122 epithelium and 122 stroma samples compared against 122 corresponding normal tissue of 122 patients) were analyzed for genomic instability using 366 microsatellite markers. LOH/AI is called in stroma or epithelium when the genotyping data at each marker is compared to data from the corresponding normal tissue from each subject. In total, 43,591 informative (non-homozygous) data points were obtained. Of these, 28,320 markers (65%) showed loss of heterozygosity/allelic imbalance (LOH/AI) and 15,271 markers (35%) retained heterozygosity (ROH). There was no difference in the number of informative markers between the stroma and epithelium (48.4% vs. 48.9%). For the epithelium, the frequency of LOH/AI per sample was 69.0% (ranging from 33.3 to 93.7%) compared to an LOH/AI frequency of 64.4% (ranging from 25.8% to 90.3%) observed in the stroma (p=0.10). In order to confirm that the high frequency of LOH/AI observed in the stroma is not a result of epithelial contamination, a multi-level approach was taken to provide conclusive evidence against an erroneous or artifactual finding (FIG. 11A-11C). First, for several cases, markers with opposing LOH/AI calls in each compartment of a given tumor (ie. LOH/AI observed in the epithelium but not stroma, and vise versa) were noted. Second, in some cases with concordant LOH/AI calls, it was found that different alleles are lost in a compartment-specific manner. Third, somatic mutations in some of these cases that were confined to either the epithelium or stroma but not in both were identified (data not shown). Since all analyses have been performed from the same pool of extracted DNA, such observations exclude to a very high probability the possibility of tissue admixture or inter-compartmental contamination.

Validating Previous Loci of Allelic Imbalance Associated with HNSCC Oncogenesis

As a control, the samples were examined for compartment-specific LOH/AI in the markers residing in the previously reported regions of LOH/AI on 3p, 9p and 17p with LOH frequencies>50% in "whole" or epithelium-only HNSCC. In this study, "strong" hot-spots of LOH/AI were observed in the microdissected tumor epithelium for two distinct regions on chromosome 3. The first chromosome 3 hot-spot maps to sub-band p25.2-25.3 (Tables 14 and 15). The second 3p hotspot maps to 3p14.2 (D3S1766) and is even more significantly associated with stroma (Table 14). The stroma also had this same hot-spot mapping to sub-band p25.2, and perhaps a broader region defined by markers D3S2432 and D3S2409 (Table 16). Among all loci, chromosome 9 harbored the second highest frequency of LOH/AI (95%) for the epithelium at 9p21.3-p23 (84% to 95%, Data not shown). Interestingly, in this study, besides a hot-spot at 17p13.1-p13.3 (TP53 locus), a hot-spot of LOH/AI was noticed at 17p13.3 (D17S1308), telomeric of the TP53 locus (Table 16). Of the 27 loci with the most significant LOH/AI in the epithelial component, 11 have been reported by other groups to harbor regional losses by CGH (Bockmuhl, U., et al., *Head Neck*, 20:145-51 (1998); Bockmuhl, U., et al., *Genes Chrom. Cancer*, 33:29-35 (2002); Huang, Q., et al., *Genes Chrom. Cancer*, 34:224-33 (2002)). Thus, of the previously reported regions of LOH/AI, all were identified in our compartment-specific study, and served as a positive control.

Novel HNSCC Compartment-Related Hot-Spots of Genomic Alterations

Hot-spots are defined as markers that show a significantly higher frequency of LOH/AI compared to all other loci on the same chromosome. In total, 70 hot-spots (at $p<0.05$ and $FPRP_{0.05}<0.5$) were identified, 17 occurring only in the epithelium, 43 only in the stroma and 10 in both epithelium and stroma (Tables 14, 15, and 16). The most significant hot-spot ($p<0.001$; $FPRP_{0.05}<0.5$) of LOH/AI observed exclusively in the epithelium was defined by D16S422 mapping to 16q23.3 (Table 15). Eight additional highly significant hot-spots of genomic instability ($p<0.01$) were identified at 1q31.1 (D1S518), 1q43 (D1S1594), 3q13.3 (D3S2460), 15q25.3 (D15S655), 16p13.3 (D16S1616), 20p12.2 (D20S851), 21q22.2 (D21S2055) and 3p25.2 (D3S4545, see above) [Table 15]. Among the 43 hot-spots of LOH/AI that were restricted to the stroma, 30 loci were highly significant ($p<0.01$, $FPRP_{0.05}<0.5$, Table 16). Highest ranked among these were D17S1308 (17p13.3) and D14S1434 (14q32.13) followed by D10S1230 (10q26), D2S1400 (2p25.2) and D2S1790 (2p11.2)[Table 16]. While the data showed that hot-spots of LOH/AI are more diverse in the tumor stroma than in the epithelium (43 vs. 17, $p=0.005$) of HNSCC, the frequency of highly significant loci among all hot-spots within each compartment was similar (9 out of 17 and 30 out of 43, $p=0.56$).

Besides the two hot-spots of LOH/AI at D3S1766 and D3S2403 mentioned above ("Validating previous loci of genomic alterations in HNSCC oncogenesis"), genomic alterations at 14q13.3 (D14S606) and 12q24.32 (D12S2078) was found most frequently in both epithelium ($p=0.0029$ and $0.0011$) and stroma ($p=0.00043$ and $0.013$) [Table 14]. Furthermore, an additional 8 loci were identified as non-compartment specific hot-spots of LOH/AI (ie, occurring equally in both epithelium and stroma) with a cut-off at $p<0.05$ and $FPRP_{0.05}<0.5$ (Table 14). One locus that retained heterozygosity (ie, did not show genomic instability) at a frequency higher than what would be expected by chance was also identified: D14S599, representing chromosome sub-band 14q13.1, showed LOH/AI only in 16 out of 58 informative samples (27.6%, $p<0.000001$) in the epithelium and 16 out of 57 (28.1%, $p<0.000001$) in the stromal compartment.

The data mining process described herein allowed the identification loci of LOH/AI that extended over 2 or more adjacent hot-spot markers, indicating larger regions of genomic alterations on chromosome arms 3p, 12q and 14q. For instance, 12q24.32 (D12S2078) harbored a hot-spot of LOH/AI for the epithelium (81.2%, $p=0.0012$) and stroma (75.0%, $p=0.013$). A second hot-spot region on chromosome 12 was located at 12q13.13 (D12S297) affecting only stroma (80.3%, $p=0.0009$) and extends further centromeric, to 12q21.33 (D12S1294) [74.3%, $p=0.014$] and to 12q24.23 (D12S395) (77.9%, $p=0.0019$). In addition, LOH/AI at 11q12.1 (D11S4459) was identified in 84.6% of the stroma ($p=0.0021$) samples. Similar associations, but with presenting clinico-pathologic features, are further explored in the next section below.

Association of LOH/AI with Presenting Clinico-Pathologic Parameters

Figure 12:
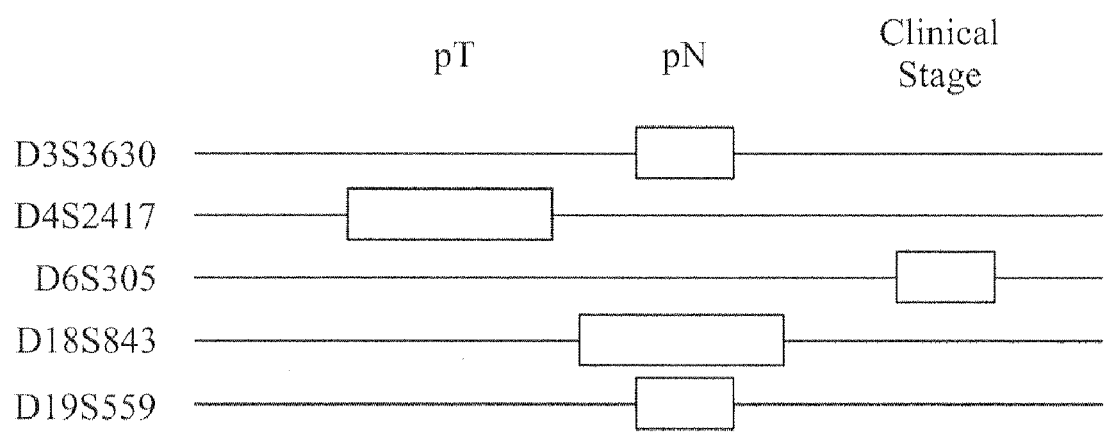
FIG. 12. Correlation between the compartment-specific LOH/AI and clinical characteristics. Each row represents one microsatellite marker with LOH/AI in the epithelium depicted in red and LOH/AI in stroma depicted by green boxes. The size of the boxes reflects the significance of LOH/AI and correlation with clinical parameter (small box: p<0.05, and large box: p<0.005). All markers illustrated here had $FPRP_{0.05}$<0.5.

Data mining was then performed on the whole-genome LOH/AI scan to in order to identify compartment-specific loci that show a correlation between LOH/AI frequency and clinico-pathologic parameters. Interestingly, stromal-specific LOH/AI-clinico-pathologic correlations were more frequently observed than for the epithelium. First, we sought to identify LOH/AI at loci that were positively associated with aggressiveness of disease as reflected by clinical stage, grade, pT and pN status (FIG. 12, Table 17). It was found that LOH/AI at D6S305 (6q26) in the epithelium occurred significantly more frequently in clinical stage III/IV HNSCC (88.6%) than in stage I/II tumors (58.3%, $p=0.011$) (Table 17). In addition, a linear increase of LOH/AI frequencies from stage I (50%) and stage II (63%) to stage III (80%) and to stage IV (95%) tumors ($p=0.011$) was observed for the locus 6q26 which contains the common fragile site FRA6E. No such association with clinical stage was identified for LOH/AI in the stroma. Interestingly, LOH/AI at D4S2417 (4q34.3) in the stroma showed a positive correlation with increasing pT stage ($p=0.00085$) (FIG. 12, Table 17). Furthermore, markers mapping to D3S3630 and D19S599 (3p26.3, $p=0.012$; 19q13.31, $p=0.017$) showed an increasing frequency of LOH/AI correlating with the degree of lymph node involvement (Table 17). For the epithelium-specific LOH/AI, genomic alterations identified at 18p11.22 (D18S843) were positively correlated with regional lymph node metastasis (pN) with 33% LOU/AI in N0 tumors compared to 79.4% in lymph node positive disease [$p=0.00092$]. Importantly, no positive correlation between LOH/AI in the epithelium and pT stage was observed.

The mucosa of the upper aero-digestive tract is exposed to an array of carcinogens that have been attributed to cause genetic and epigenetic changes in the squamous cell lining and ultimately lead to HNSCC genesis. It is evident that these carcinogens not only affect these epithelial cells but also the mesenchymal fibroblasts, the latter representing the largest component of the stroma. With this study it is shown for the first time, that indeed the stromal cells in HNSCC are subjected to selection for locus-specific LOH/AI events. The high frequency of LOH/AI especially in the tumor stroma might appear distracting at first. However, it does reflect the biological background behind HNSCC since in the study only patients with a history of smoking have been analyzed. In addition, technical aspects have to be considered as well. First, it is important to note our operational definition of a hot-spot, which is defined as a locus having a significantly high frequency of LOH/AI compared to all other loci along the same chromosome. Thus, it is possible that other studies using a small set of markers might therefore find an apparently high frequency of LOH/AI in one marker and labeled this locus significant; however, other loci along the same chromosome, which may not have been examined, might actually have LOH/AI to a similar or even elevated degree than the selected marker. In addition, studies using array comparative genomic hybridization (aCGH), while having the advantage of differentiating between allelic gain and loss, usually detect losses/gains of larger genomic regions, spanning several BAC clones. In contrast, microsatellite marker LOH analysis is able to accurately identify submicroscopic deletions or even single base-pair alterations, if those affect the microsatellite marker priming sites. However, it is important to recognize that in this study, the common observation of "early events" (ie. those with high frequency of LOH/AI) attributed to HNSCC oncogenesis that are loss at 3p, 9p and 17p in the tumor epithelium (Table 14) could be recapitulated. This acts as a control that the data mining approach described herein can correctly identify compartment-specific hot-spots of genomic instability in microdissected epithelium and, more importantly, the stroma of HNSCC lesions.

Multiplicity of LOH/AI Hot-Spots in the Stroma of HNSCC

Interestingly, more LOH/AI hot-spots were observed in the stroma than epithelium. Even where the same LOH/AI hot-spot markers were found in both the epithelium and stroma, overall, the frequencies of LOH/AI were much higher in the corresponding stroma (Table 14). This may indicate that only a very limited set of key genetic alterations within the epithelium are required to initiate HNSCC genesis and other alterations are downstream events or even bystander events. This has been addressed previously by Gotte et al. who reports on the intratumoral heterogeneity of HNSCC (Gotte, K., et al., *Adv. Otorhinolaryngol.*, 62:38-48 (2005)). In contrast, the multiplicity of stroma-specific hot-spots, likely occurring along all steps of carcinogenesis, indicate that these play the fundamental role in influencing the biological diversity, and hence, clinical behavior, of the disease (FIG. 12, see next sections). Whether the accumulation of stromal alterations occurs concordant with the neoplastic transformation of the epithelium or in fact precedes the malignant transformation of the squamous epithelium is unknown. In breast cancers from individuals with germline BRCA1/2 mutations, the inherited dysfunction in these repair genes seems to dictate that stromal genomic alterations occur before or at least simultaneously with epithelial transformation (Weber, F., et al., *Am. J. Hum. Genet. J.*, 78(6):961-72 (2006)).

Besides several genes involved in oncogenesis or cell-cell communication mapping to these hot-spots, micro-RNA's that might become deregulated through allelic imbalance were also found. It is becoming in emerging concept that the deregulation of micro-RNA's participate not only in development but also cancer. For instance hsa-miR-181 (19p13.12) was identified as a stroma-specific hot-spots, and has been implicated in cellular differentiation through regulation of homeobox genes (Naguibneva, I., et al., *Nat. Cell. Biol.*, 8(3):278-84 (2006)). Given that hot-spot and LOH/AI frequencies highest in stroma, it is likely that if field cancerization precedes invasive HNSCC, then the mesenchymal cells undergo genetic alterations first.

Evidently, the positively selected stromal cells acquire additional hits, presenting as multiple hot-spots of LOH/AI, that can lead to aberrant excretion of proteins and misinterpretation of incoming signals resulting in disruption of the physiologic interplay between epithelium and stroma and provides the necessary microenvironment to sustain and promote tumor progression (Mueller, M. M., *Nat. Rev. Cancer*, 4:839-49 (2004); McCawley, L. J., et al., *Curr. Biol.*, 11:R25-7 (2001); Bhowmick, N. A., et al., *Nature*, 432(7015):332-7 (2004)). Seemingly paradoxically, however, one locus mapping to 14q13.1 retained heterozygosity at a significant frequency in both epithelium and stroma, indicating that genes mapping to those loci might be necessary for maintenance of cell integrity or key regulatory genes might be frequently affected by somatic sequence variants that will cause a dominant negative acting transcripts. Interestingly, among the genes within this region is PHD3 (prolyl hydroxylase domains 3; equivalent to EGLN3) involved in oxygen sensing and regulation of especially HIF-2α (Appelhoff, R. J., et al., *J. Biol. Chem.*, 279(37):38458-65 (2004)).

LOH/AI at 5 Markers in the Stroma and 2 in the Epithelium Correlate with Presenting Clinico-Pathologic Features As described herein, 5 specific loci of LOH/Ai associated with clinico-pathologic features at presentation were found (FIG. 12). Amongst all the hotspot loci associated with presenting clinico-pathologic features, these specific 5 were identified with sequentially increasing LOH/AI frequencies significantly associated with increasing pT, pN and/or clinical stage and with a low likelihood of representing false positive associations. Interestingly, 3 specific loci occurred in the stroma, associated with tumoral attributes of aggressive disease and invasion, namely, size (pT status; 1 locus at 4q34.3) and regional lymph node status (pN, 2 loci at 3p26.3 and 19q13.31). One gene in the 4q34.3 region is NEIL3 which encodes a class of glycolases which initiate the first step in base excision repair. One therefore could postulate that loss of NEIL3 could be one of the first events leading to a cascade of genomic alterations in the stroma (Rosenquist, R. A., et al., *DNA Repair*, 2:581-91 (2003)).

It does also appear that the stroma plays an important role in metastases where 2 of the 3 hot-spot loci, at 3p26.3 and to 19q13.31, in the stroma are correlated with increasing pN status (FIG. 12). There are likely several genes mapping to these regions. One relevant gene mapping to 3p26.3 is FANCD2 which encodes one of the enzymes in the Fanconi anemia (FA) pathway pivotal to DNA repair and which interacts with BRCA1 and BRCA2 (Taniguichi, T., et al., *Blood*, 7:2414-20 (2002); Hussain, S., et al., *Hum. Mol. Genet.*, 13:1241-8 (2004)). Interestingly, the FA pathway is again targeted by the loss of a gene encoding FAZF on 19q13.3, the other stromal locus whose loss is associated with pN status. This zinc finger protein binds to another FA pathway member FANCC in a region that is deleted in FA patients with a severe disease phenotype (Hoatlin, M. E., et al., *Blood*, 94:3737-47 (1999); Dai, M. S., et al., *J. Biol. Chem.*, 277:26327-34 (2002)). This 19q locus is proximal to another DNA repair enzyme gene, ERCC2. ERCC2, or XPD, is an excision repair enzyme which has been identified to have an increased risk of cancer when mutated, due to abrogation of its transcriptional activation of FBP, a regulator of MYC (Dai, M. S., et al., *J. Biol. Chem.*, 277:26327-34 (2002)). The observations herein, therefore, indicate that these genes in concert may play a role in HNSCC and in particular, relevant to regional metastases. It is tantalizing that the most promising candidate genes in the regions of loss associated with clinicopathologic features belong to the various repair pathways. The loss of FANCD2, FAZF, and ERCC2 together could additively and more severely result in additive loss of repair capabilities that result in a cascade of downstream genomic alterations, leading to genomic instability resulting in invasion and metastasis. This postulate is supported by the observations herein in the multiplicity of genomic alterations in HNSCC stroma (see above, Tables 14-16). In further support of this hypothesis, a QTL for prostate cancer aggressiveness has been identified in this region by two groups (Witte, J. S., et al., *Am. J. Hum. Genet.*: 1:92-9 (2000); Slager, S. L., et al., *Am. J. Hum. Genet.*, 3:759-62 (2003)), suggestive that a gene(s) is harbored in this location that may also be important in HNSCC aggressiveness, as our association of this locus to pN suggests. Equally significant is the locus reflected by D18S843 (18p11.2) in the epithelium. Allelic loss for this region has previously been implicated in other solid tumors and even associated with relapse in breast cancer (Climent, J., et al., *Clin. Cancer Res.*, 8(12):3863-9 (2002); Tran, Y., et al., *Oncogene*, 17(26):3499-505 (1998)). From the genes mapping to this loci it is unclear what the likely candidate will be; of note is APCDD1 with suggested oncogenic properties in colorectal cancer. Importantly, this gene is expressed during development to regulate epithelial-mesenchymal interaction (Jukkola, T., et al., *Gene Expr. Patterns*, 4(6):755-762 (2004)). Only a single specific locus (D6S305) was independently identified as a hot-spot of LOH/AI associated with clinical stage. Deletions of 6q26 (D6S305) have been reported to have a role in carcinogenesis before. This region harbors the common fragile site FRA6E that spans 8 genes (IGF2R, SLC22A1, SLC22A2, SLC22A3, PLG, LPA, MAP3K4, and PARK2), which have been implicated in the development of solid cancer (Denison, S. R., et al., *Genes Chromosomes Cancer*, 38(1):40-52 (2003)).

Conclusions

The observations described herein indicate that the apparently non-malignant stroma of HNSCC is rich in genomic alterations. The strong association of a limited number of specific loci with sequentially higher frequencies of LOH/AI in the stroma with clinical aggressiveness indicates that mesenchyme is affected by carcinogens to the same extent as the squamous cell epithelium, and even more importantly, contributes in a fundamental way to the clinical phenotype of HNSCC. The data described herein indicate that this genetically altered mesenchymal field might provide the soil which facilitates the HNSCC invasion and metastases. It is likely that these genomic observations, which point to genomic regions which likely harbor many genes, will guide future in-depth functional and mechanistic studies. Nonetheless, the present observations provide new biomarkers for prediction of clinical outcome and novel compartments for targeted therapy and prevention.

TABLE 13

Patient Characteristic

| Characteristic | | | Number | Frequency |
|---|---|---|---|---|
| Sex | male | | 86 | 71.1% |
| | female | | 35 | 28.9% |
| Age | mean | 58.5 years | | |
| | | (+/− 12.9 years) | | |
| Primary site | Oral | | 55 | 46.6% |
| | Pharynx | | 63 | 53.4% |
| Stage | I | | 16 | 14.5% |
| | II | | 22 | 20.0% |
| | III | | 34 | 30.9% |
| | IV | | 38 | 34.5% |
| pT | T1 | | 23 | 20.9% |
| | T2 | | 44 | 40.0% |
| | T3/4 | | 43 | 39.1% |
| pN | N0 | | 44 | 39.3% |
| | N1 | | 24 | 21.4% |
| | N2 | | 39 | 34.8% |
| | N3 | | 5 | 4.5% |
| Grade | Low | G1, 2 | 83 | 80.6% |
| | High | G3 | 20 | 19.4% |

TABLE 14

Hot-Spots of LOH/AI in both Epithelium and Stroma

| Marker | Loci | Epithelium p-value[a] | Stroma p-value[a] | Genes |
|---|---|---|---|---|
| D1S1596 | 1p32.1 | 0.00026 | 0.0000001 | JUN, HOOK, CYP2J2 |
| D3S1766 | 3p14.2 | 0.014 | 0.00047 | FLNB, PDHB, hsa-mir425, hsa-mir191 |
| D3S2403 | 3p25.2 | 0.0013 | 0.013 | CAV3, RAD18, CAMK1, FANCD2, VHL, PPARG, RAF1, HDAC11, FBLN2, WNT7A |
| D6S305 | 6q26 | 0.024 | 0.022 | IGF2R, MAP3K4, MAS1, PLG, SLC22A1 |
| D12S2078 | 12q24.32 | 0.0012 | 0.013 | TMEM132 |
| D14S599 | 14q13.3 | 0.000001[b] | 0.000005[b] | RGLN3, SNX6, CFL2, BAZ1A |
| D14S606 | 14q31.1 | 0.0029[b] | 0.00043[b] | TSHR, GTF2A1, STON2 |
| D17S2180 | 17q21.32 | 0.0054 | 0.0013 | SCAP1, HOXB1-9, IGFLBP1 |
| D19S591 | 19p13.3 | 0.000018[b] | 0.000005[b] | GADD45, ZNF77, TLE2, AES |
| D21S1437 | 21q21.1 | 0.0063[b] | 0.00008[b] | NCAM2 |

[a]Multiple testing adjustment is based on $FPRP_{0.05} < 0.5$.
[b]Multiple testing adjustment is based on $FPRP_{0.01} < 0.5$.

TABLE 15

Hot-Spots of LOH/AI in Epithelium

EPITHELIUM

| Marker | Loci | p-value[a] | Genes |
|---|---|---|---|
| D1S518 | 1q31.1 | 0.0070 | PRG4, TPR, PTGS2, PLA2G4A |
| D1S1594 | 1q43 | 0.008 | FMN2, GREM2 |
| D3S4545 | 3p25.2 | 0.0076 | FANCD2, VHL, PPARG, RAF1, HDAC11, FBLN2, WNT7A |
| D3S2460 | 3q13.3 | 0.0053 | LSAMP, IGSF11 |
| D5S1462 | 5q15 | 0.0149 | LNPEP, LIX1 |
| D8S1128 | 8q24.21 | 0.015 | MYC |
| D10S1423 | 10p12.31 | 0.0193 | PLXDC2 |
| D11S1999 | 11p15.4 | 0.013 | ADM, CTR9, GALNTL4 |
| D13S796 | 13q33.3 | 0.011 | EFNB2, LIG4, ABHD13, TNFSF13B |
| D15S655 | 15q25.3 | 0.0046[b] | DET1, hsa-mir-7-2, hsa-mir-9-3 |
| D16S2616 | 16p13.3 | 0.009 | DNAJA3, A2BP1 |
| D16S422 | 16q23.3 | 0.0002[b] | HSD17B2, CDH13, HSBP1 |
| GATA178F11 | 18p11.32 | 0.023 | TGIF |
| D18S1376 | 18q11.2 | 0.015 | CDH2, RBBP8, CABLES, |
| D20S851 | 20p12.2 | 0.007 | PLCB1, PAK7 |
| D21S2055 | 21q22.2 | 0.0039[b] | ETS2, PCP4, DSCAM |
| D22S683 | 22q12.3 | 0.018 | H1F0, POLR2F, PLA2G6 |

[a]Multiple testing adjustment is based on $FPRP_{0.05} < 0.5$.
[b]Multiple testing adjustment is based on $FPRP_{0.01} < 0.5$.

TABLE 16

Hot-Spots of LOH/AI in Stroma

STROMA

| Marker | Loci | p-value[a] | Genes |
|---|---|---|---|
| D1S3721 | 1p34.2 | 0.005[b] | CITED, JMJD2 |
| GATA133A08 | 1p21.1 | 0.0056 | VAV3, NBPF4 |
| D2S1400 | 2p25.1 | 0.0002[b] | ADAM17, E2F6 |
| D2S1790 | 2p11.2 | 0.00057[b] | POLR1A |
| D2S1334 | 2q21.3 | 0.006[b] | CXCR4, ZRANB3 |
| D2S1776 | 2q24.3 | 0.0081 | NOSTRIN |
| D3S2432 | 3p22.3 | 0.001[b] | TGFBR2, GPD1L |
| D3S2409 | 3p21.32 | 0.026 | COL7A1, RHOA, TRAIP, TUSC2, RASSFIA |
| D3S1262 | 3q27.2 | 0.017 | CRYGS, AHSG, KNG1 |
| D3S2418 | 3q28 | 0.0088 | FGF12, CLDN1 |
| D4S1647 | 4q23 | 0.0018[b] | TSPAN5, EIF4E |
| D5S2500 | 5q11.2 | 0.0068 | PDE4D |
| D5S1725 | 5q14.3 | 0.002[b] | TMEM161B, MEF2C |
| D5S820 | 5q33.3 | 0.012 | TIMD4, SGCD |
| D6S474 | 6q21 | 0.001[b] | FOXO3A, PRDM1 |
| D6S1027 | 6q27 | 0.0008[b] | SMOC2, THBS2 |

TABLE 16-continued

Hot-Spots of LOH/AI in Stroma

STROMA

| Marker | Loci | p-value[a] | Genes |
|---|---|---|---|
| D7S3061 | 7q31.3 | 0.0019[b] | NDUFA5, ASB15, WASL |
| D7S1804 | 7q32.3 | 0.021 | hsa-mir-29b-1 |
| D7S3070 | 7q36.1 | 0.0028[b] | PRKAG2, GALNT11 |
| D8S1477 | 8p12 | 0.01 | PPP2CB, WRN, NRG1 |
| D10S1208 | 10p11.21 | 0.0024[b] | NRP1, PARD3, FZD8 |
| D10S1230 | 10q26.1 | 0.00005[b] | INPP5P, BRWD2 |
| D10S1222 | 10q26.2 | 0.0063 | MMP21, BCCIP, APAM12 |
| D11S4459 | 11q12.1 | 0.0021[b] | SSRP1, CTNND1, hsa-mir-130a |
| D11S1998 | 11q23 | 0.0004[b] | DCSAM, FXYD2, IL10RA |
| D11S4464 | 11q24.1 | 0.011 | HSPA8, LOH11CR2A, PANX3, ESAM, ACVR1, hsa-mir-125b-1, hsa-mir-100 |
| D12S1042 | 12p11.23 | 0.015 | ARNTL2, PTHLH |
| D12S297 | 12q13.13 | 0.0009[b] | ACVR1B |
| D12S1294 | 12q21.33 | 0.014 | CEP290, KITLG, DUSP6, |
| D12S395 | 12q24.23 | 0.0019[b] | HSPB8, RAB35, MSI1, TRIAP1 |
| D13S787 | 13q12.12 | 0.013 | TNFRSF19 |
| D13S285 | 13q34 | 0.0009[b] | ING1, SOX1, TUBGCP3 |
| D14S1280 | 14q12 | 0.012 | PRKD1 |
| D14S588 | 14q24.1 | 0.015 | WDR22, ERH, SFRS5, SMOC1 |
| D14S1434 | 14q32.13 | 0.000002[b] | MOAP1, DICER1, VRK1 |
| D16S403 | 16p12.1 | 0.021 | POLR3E, PLK1 |
| D16S3396 | 16q12.1 | 0.002 | CARD15 |
| D16S516 | 16q23.1 | 0.013 | ADAMTS18, WWOX, MAF |
| D17S1308 | 17p13.3 | 0.000002[b] | HIC1, hsa-mir-132, hsa-mir-212 |
| D17S1294 | 17q11.2 | 0.004[b] | CCDC55, SLC6A4, hsa-mir-423 |
| D19S714 | 19p13.12 | 0.0036[b] | CASP14, NOTCH3, hsa-mir-27a, hsa-mir-23a, hsa-mir-181c,d |
| D20S103 | 20p13 | 0.0005[b] | DEFB1287BC1D2, FKBP1A |
| D21S2052 | 21q21.3 | 0.00031[b] | JAM2, APP, ADAMTS1,5, hsa-mir-155 |

[a]Multiple testing adjustment is based on FPRP$_{0.05}$ < 0.5.
[b]Multiple testing adjustment is based on FPRP$_{0.01}$ < 0.5.

TABLE 17

LOH/AI in epithelium associated with clinical stage

| Marker | Loci | stage I | | stage II | | stage III, IV | | p-value[a] |
|---|---|---|---|---|---|---|---|---|
| | | LOH | ROH | LOH | ROH | LOH | ROH | |
| D6S305 | 6q26 | 2 | 2 | 5 | 3 | 31 | 4 | 0.011 |

LOH/AI in stroma associated with pT

| Marker | Loci | pT1 | | pT2 | | pT3, 4 | | p-value[a] |
|---|---|---|---|---|---|---|---|---|
| | | LOH | ROH | LOH | ROH | LOH | ROH | |
| D4S2417 | 4q34.3 | 5 | 4 | 10 | 6 | 21 | 0 | 0.0008 |

LOH/AI in stroma or epithelium (*) associated with pN

| Marker | Loci | pN0 | | pN1 | | pN2, 3 | | p-value[a] |
|---|---|---|---|---|---|---|---|---|
| | | LOH | ROH | LOH | ROH | LOH | ROH | |
| D3S3630 | 3p26.3 | 9 | 17 | 9 | 6 | 18 | 8 | 0.0123 |
| D19S559 | 19q13.31 | 9 | 14 | 10 | 4 | 15 | 3 | 0.0165 |
| D18S843* | 18p11.22 | 5 | 10 | 7 | 3 | 20 | 4 | 0.0009[b] |

LOH, loss of heterozygosity;
ROH, retention of heterozygosity;
[a]Multiple testing adjustment is based on FPRP$_{0.05}$ < 0.5.
[b]Multiple testing adjustment is based on FPRP$_{0.01}$ < 0.5.

Example 4

Targets for Use in Prognosis and Therapy of Breast Cancer

Materials and Methods

Breast Carcinoma Samples and Laser Capture Microdissection

Two hundred and twenty unrelated samples of primary sporadic invasive carcinomas of the female breast annotated by basic clinicopathologic features were obtained under the approval of the respective Institutional Review Boards. Samples from males with breast cancer, those with a personal history of ovarian cancer and those with one or more first degree relatives with breast or ovarian cancer were excluded. Widely metastatic disease (TxNxM1) was also an exclusion criterion. Anonymized sections from archived blocks were linked only to their respective clinicopathologic features. No personal identifiers or linking files were maintained. Laser capture microdissection (LCM) was performed using the Arcturus PixCell II microscope (Arcturus Engineering Inc., Mountain View, Calif.) to isolate neoplastic epithelium and tumor stroma separately (Kurose, K., et al., *Hum. Mol. Genet.*, 10:1907-1913 (2001); Kurose, K., et al., *Nat. Genet.*, 32:355-357 (2002); Fukino, K., et al., *Cancer Res.*, 64:7231-7236 (2004); Weber, F., et al., *Br. J. Cancer*, 92:1922-1926 (2005); Weber, F., et al., *Am. J. Hum. Genet.*, 78:961-972 (2006)). Tumor-associated stromal fibroblasts were collected from locations proximate to epithelial tumor cells, being within 5 mm of an epithelial tumor nodule. Corresponding germline reference DNA for each case was procured from normal tissue, either within the breast but at least 1 cm distant from malignant epithelial cells, or from histologically normal tissues outside the breast. The different origins of the corresponding germline DNA had no effect on the frequency or pattern of loss of heterozygosity/allelic imbalance (LOH/AI). Photomicrographs of Laser Capture Microdissection of sporadic breast cancer samples.

Laser Capture Microdissection (LCM) was performed on sporadic breast cancer samples stained with hematoxylin and eosin (H&E). The distinction between epithelial and stromal components was very clear under direct microscopic observation. In order to avoid the cross contamination of epithelial components into stromal components, epithelial tissues were first captured, then surrounding stromal tissues were captured.

Whole Genome Genotyping for LOH/AI

Figure 13A:
FIGS. 13A-13B. Examples of Multiplex PCR Plots Performed for Total Genome LOH/AI Scanning. In both FIGS. 13A and 13B, the top tracings represent the multiplex genotyping plot for the non-neoplastic normal tissue, and the middle and the bottom tracings are plots for the corresponding stromal and epithelial compartments, respectively, of the breast cancer.
Figure 13B:
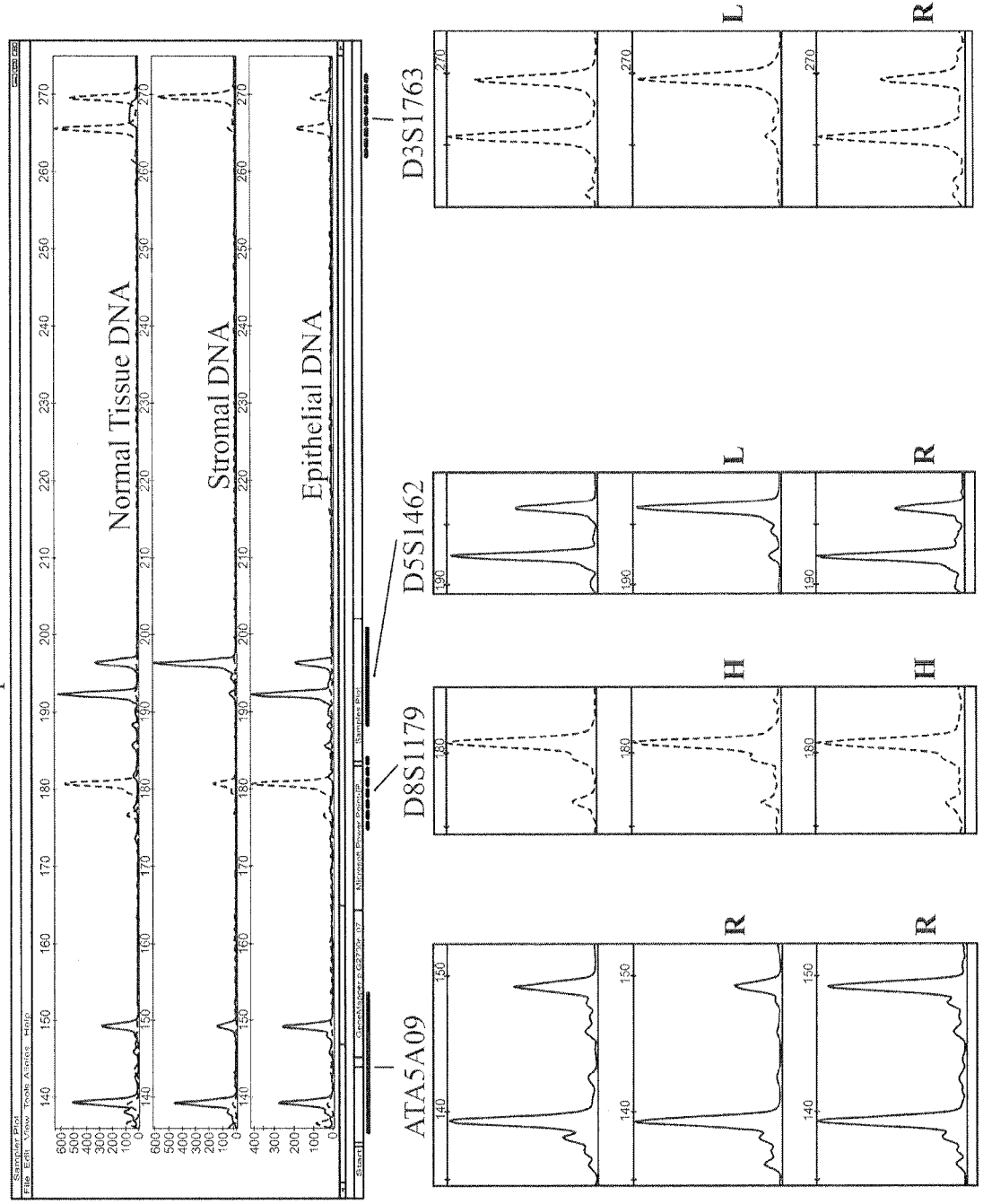

Genomic DNA was extracted as previously described (Kurose, K., et al., Hum. Mol. Genet., 10:1907-1913 (2001); Kurose, K., et al., Nat. Genet., 32:355-357 (2002)), with incubation in Proteinase K at 65° C. for 2 days (Fukino, K., et al., Cancer Res., 64:7231-7236 (2004)). The primer sets for multiplex PCR defined 386 microsatellite markers in 72 multiplex panels (ResGen, Invitrogen, Carlsbad, Calif.). Genotyping was performed with the ABI 3730 DNA analyzer (Applied Biosystems, Foster City, Calif.). The genotyping results were analyzed by automated fluorescence detection using the ABI Genemapper v3.5 (Applied Biosystems, Foster City, Calif.). Scoring of LOH/AI (loss of heterozygosity/allelic imbalance) and ROH (retention of heterozygosity) was done by inspection of the Genemapper outputs (illustrated in FIGS. 13A-13B). A ratio of peak heights of alleles between germ-line and epithelial carcinoma or surrounding stromal DNA$\geq$1.5 was used to define LOH/AI (Weber, F., et al., Am. J. Hum. Genet., 78:961-972 (2006); Marsh, D., et al., Cancer Res., 57:500-503 (1997); Dacic, S., et al., Am. J. Surg. Pathol., 29:897-902 (2005); Nelson, H., et al., Carcinogenesis, 26:1770-1773 (2005)). The methodological veracity of LOH/AI using multiplex-PCR on archived templates was extensively validated as published (Fukino, K., et al., Cancer Res., 64:7231-7236 (2004)). Three samples were excluded from statistical analyses because none of the tested loci were informative (all loci homozygous in germline). Statistical analyses were performed on the remaining 217 samples, each of which was informative for at least 79 chromosomal loci. The total number of 386 microsatellite markers were used for total genome LOH/AI scan, and each chromosome contained from 7 (chromosome 21) to 31 (chromosome 1) markers. Standard quality control measures for both LCM-procurement and replicability of compartment-specific LOH/AI calls are detailed in our previous publications, including the comparisons between the results of PCR on the DNA extracted from LCM-captured tissues and those on the DNA from the corresponding frozen tissues, and between the results from multiplex PCR genotyping and those of quantitative PCR and the lack of cross contamination between compartments (Kurose, K., et al., Hum. Mol. Genet., 10:1907-1913 (2001); Fukino, K., et al., Cancer Res., 64:7231-7236 (2004); Weber, F., et al., Br. J. Cancer, 92:1922-1926 (2005); Weber, F., et al., Am. Hum. Genet., 78:961-972 (2006); Ginzinger, D., et al., Cancer Res., 60:5405-5409 (2000); Nigro, J., et al., Am. J. Pathol., 158:1253-1262 (2001)).

Mutation Analysis of TP53

Mutation analysis was performed on the 112 breast cancer samples which had informative LOH/AI data at D17S796. Genomic DNA from the epithelium and stroma from each breast carcinoma was subjected to mutation analysis for TP53. The classic mutation cluster region of this gene, exons 4-9, exon-intron boundaries and flanking intronic regions of TP53 were analyzed by PCR-based direct sequence analysis using the ABI3730x1 as previously described (Fukino, K., et al., Cancer Res., 64:7231-7236 (2004)). When a mutation was found in the epithelium and/or stroma, the corresponding germline was examined. No germline TP53 mutations were found and thus, all mutations found in the breast cancer samples were somatic.

Clinico-Pathologic Features at Time of Diagnosis

Presenting demographic and clinico-pathologic features included age, tumor grade (modified Scarff-Bloom-Richardson Grades I-III) (Bloom, H. J., et al., Br. J. Cancer, 11:359-377 (1957); Le Doussal, V., et al., Cancer, 64:1914-1921 (1989); Elston, C., et al., Histopathology, 19:403-410 (1991)), tumor size, estrogen- and progesterone-receptor (ER and PR, respectively) expression status, and human epidermal growth factor receptor 2 (HER2/neu) expression status, as well as primary tumor status (pT) and regional lymph node metastasis status (pN) and Clinical Stage Grouping based on the 6th edition of the American Joint Committee on Cancer (AJCC) Cancer Staging Manual (Greene, F., et al., eds. AJCC Cancer Staging Manual, 6th edition. New York: Springer-Verlag; (2002)). For hormone receptor analysis, the percentage of immunoreactive nuclei was assessed visually and the results were categorized as follows: (+)>10% of nuclei, (+/−) >0% to <10% of nuclei and (−) 0% of nuclei immunoreactive. In HER2/neu analysis, the results were scored as follows: (0) no immunoreactivity or immunoreactivity in <10% of tumor cells, (1+) faint weak immunoreactivity in >10% of tumor cells but only a portion of the membrane is positive, (2+) weak to moderate complete membrane immunoreactivity in >10% of tumor cells, (3+) moderate to strong complete membrane immunoreactivity in >10% of tumor cells. Scores (0) and (1+) were regarded as negative (−), and (2+) and (3+) as positive (+), respectively. Cytoplasmic immunoreactivity alone was scored as a negative result.

Compartment-Specific LOH/AI Profile and Clinico-Pathologic Features:

Analysis of Similarities of LOH/AI Patterns in Epithelium, in Stroma, and Between the Epithelium and the Stroma Derived from the Same Samples Using Mcnemar's Test, Hierarchical Clustering and Multi-Dimensional Scaling McNemar tests were performed to compare the LOH/AI between each compartment-pair (epithelium and stroma) from each of the tumors and the pooled samples to test whether LOH/AI is more frequent in one compartment than the other. Dissimilarities between each compartment-pair (epithelium and stroma) from each of the tumors can be measured by the percentage of discordant pairs of LOH/AI, ie, the proportion of markers showing LOH in one compartment and ROH in the other among all the markers which were informative in both compartments. Multi-dimensional scaling using principal coordinate analysis measures the distance between a pair of samples and approximates the dissimilarity between the two as measured by the percentage of discordant LOH/AI. Based on the results for multi-dimensional scaling, two of 217 tumors appeared to have very different LOH/AI patterns from those of the rest of the samples. This was most likely due to the small number of informative markers for these two tumors (39 and 46 informative markers in epithelium and stroma combined). Therefore, these two samples were excluded from multi-dimensional scaling and hierarchical clustering analyses. Hierarchical clustering with average linkage and multi-dimensional scaling was first performed for 430 samples, epithelium and stroma separately, derived from the 215 tumors. The clustering was performed using a function in the statistical package R (used for all statistical analyses in this report and detailed by Venables and Ripley (Venables, W. N., et al., Modern Applied Statistics with S-Plus, New York: Springer; 1994); Venables, W. N., et al., S Programming, New York: Springer; 2000)), and the standard option of average linkage was used. As an unsupervised (unbiased) method, genotype was then correlated with the presenting CPF by repeating the same analysis using one clinicopathologic variable at a time. The same analysis was then performed by combining the epithelium and stroma samples from the same tumor to study the overall LOH/AI profile of the tumor.

Associations Between LOH/AI and Clinico-Pathologic Features

Statistical models were applied to study the relationships between compartment-specific LOH/AI and clinico-pathologic data. Logistic regression models were used for CPFs with binary features and proportional odds regression models were used for CPFs with more than two ordered classes. The covariates in these models are chromosome-wise LOH/AI frequencies for either compartment (stroma/epithelium) from each tumor. From these analyses, we obtained a p-value across each chromosome in each compartment and each CPF, representing the strength of evidence for the correlation between LOH/AI on that particular chromosome in that compartment and the CPF. For the group of tests for a specific compartment and CPF, Bonferroni adjustment was applied to correct for multiple testing. For any association that was statistically significant, Fisher's 2-tailed exact tests were used to associate the CPF with LOH/AI at individual markers on that chromosome in that compartment.

Results

Comparisons Between LOH/AI in Epithelium and that in Stroma

Overall, LOH/AI was more frequent in epithelium than in stroma: in the epithelium across all tumors, 43598 PCR reactions were informative for evaluation of LOH/AI and 22288 (51.1%) showed LOH/AI, compared to an overall 47.6% (18644 out of 39192) in stroma (chi-square p-value $2.2 \times 10^{-16}$). At the chromosomal level, model-based estimates for the LOH/AI frequency (Fukino, K., et al., *Cancer Res.*, 64:7231-7236 (2004)) were significantly higher in epithelium than in stroma for 5 chromosomes (chromosomes 7, 8, 13, 16 and 17) at the 0.05 level (Table 18), and remain so for 3 chromosomes (chromosomes 8, 13 and 17) after Bonferroni adjustment for multiple testing (p<0.05/23).

As proof of concept that regions with significantly high LOH/AI often harbor relevant genes, the p13 region of chromosome 17, which harbors the TP53 tumor suppressor gene, was studied. One of the major regions of LOH is within 17p13, where LOH at D17S796 (17p13.2) in the epithelium occurs in 72 of 112 (64%) informative (ie germline heterozygous at this marker) breast cancer samples from our series; and in the stroma, 56/106 (53%) of informative samples (7 stromal samples failed to amplify). D17S796 is a proximal marker for the TP53 tumor suppressor gene. Therefore, direct mutation analysis was performed by sequencing of the classic mutation cluster region, exons 4-9 and flanking intronic sequences of TP53 of all epithelial and stromal samples from the 113 breast cancers with informative LOH data at this locus. It was found that 29 of 112 (27%) tumors had somatic intragenic TP53 mutations in the epithelium and 28 of 106 (26%) had somatic TP53 mutations in the stroma. Only 8 tumors had somatic TP53 mutations in both epithelium and stroma, but for each of these 8 samples, the mutation found in epithelium was different from that in stroma. Thus, 21 tumors had TP53 mutations only in the epithelium and another 20 tumors had somatic mutations only in the stroma. Of the 30 with TP53 mutations in the epithelium, 80% had LOH at D17S796. Among the 28 with TP53 mutations in the stroma, 65% had LOH at this marker.

Comparison of LOH/AI Profiles Between the Epithelium and the Stroma Derived from the Same Samples The results of the McNemar tests comparing the LOH/AI between the epithelium and stroma samples derived from the 217 subjects indicates that for a larger number of subjects, LOH/AI is observed more frequently in the epithelium, represented by the positive p-values. This result is consistent with the overall test, which indicated strong evidence for more frequent LOH/AI in the epithelium (P<0.001). Neither multi-dimensional scaling or hierarchical clustering revealed any strong similarity between LOH/AI profiles for the epithelial or the stromal samples from the same subject, providing a good control for non-contamination between compartments (figures not shown). The hierarchical clustering did result in the samples clustering progressively, with the most similar samples clustered together first.

Model of the Association Between Clinico-Pathologic Features and LOH/AI

A two-stage approach was taken to look for associations between compartment-specific LOH/AI and CPF's. First, such associations were screened for at the chromosome-level. The chromosomes that yielded significant correlations were then subjected to analysis at the individual marker level to determine associations between LOH/AI at specific markers/loci and the CPF's. For the first stage, therefore, formal model-based methods were applied to examine the correlations between LOH/AI and the presenting CPFs. Compartment-specific LOH/AI data were used to classify the CPFs using logistic and ordinal regression models, with chromosome-wise LOH/AI as the independent variable, for each chromosome in turn, and obtained p-values for each presenting CPF. The obtained p-values (Table 19) represent the strength of evidence for the correlation between LOH/AI on a particular chromosome and the particular presenting CPF.

Figure 14A:
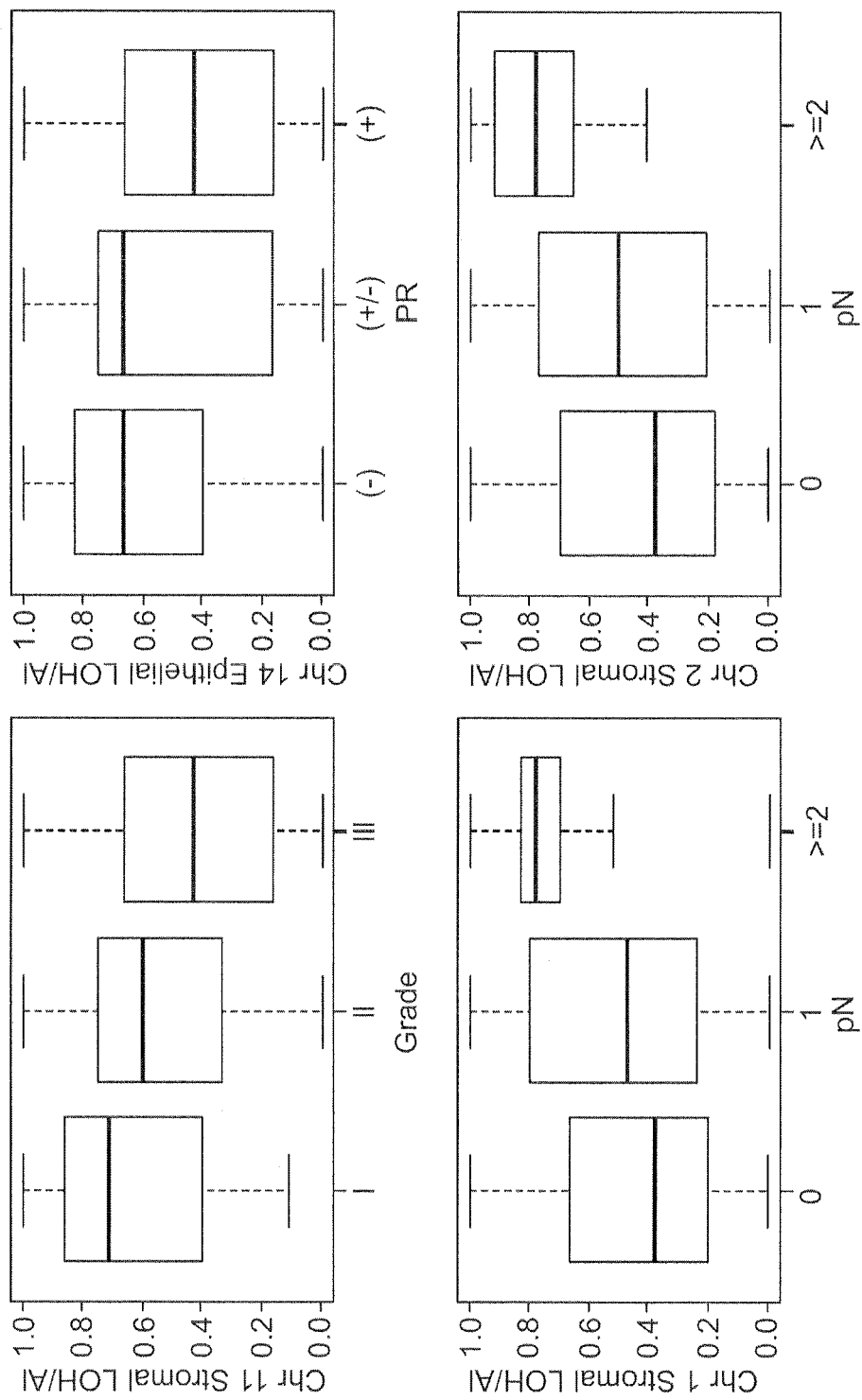
FIGS. 14A-14B. Associations between LOH/AI and Presenting Clinico-Pathologic Features (CPF). For each chromosome and compartment (labeled to the left of each y-axis) whose LOH/AI frequency (LOH/AI frequencies are on the y-axis) was found to be related to a CPF (x-axis), the summary statistics of LOH/AI frequency for each level of the CPF (I-III for Grade; +, −, +/− for PR and 0, 1, ≧2 for pN) are given in a box plot. The characteristics depicted include the mean (line in the middle of each box), the inter-quartile range (height of the box) and outlying observations (additional outside lines above and below each box). From the pattern of boxes in each plot, it is evident that each of these chromosomes shows a consistently increasing or consistently decreasing trend over the levels of the corresponding CPF. For example, for the plot labeled Chr 1 Stromal LOH/AI, the frequencies of LOH/AI start at an average of slightly under 40% (0.4) with no regional lymph node metastases (pN0) to 45% at pN1 and rise to an average of 80% for pN2 and above.
Figure 14B:
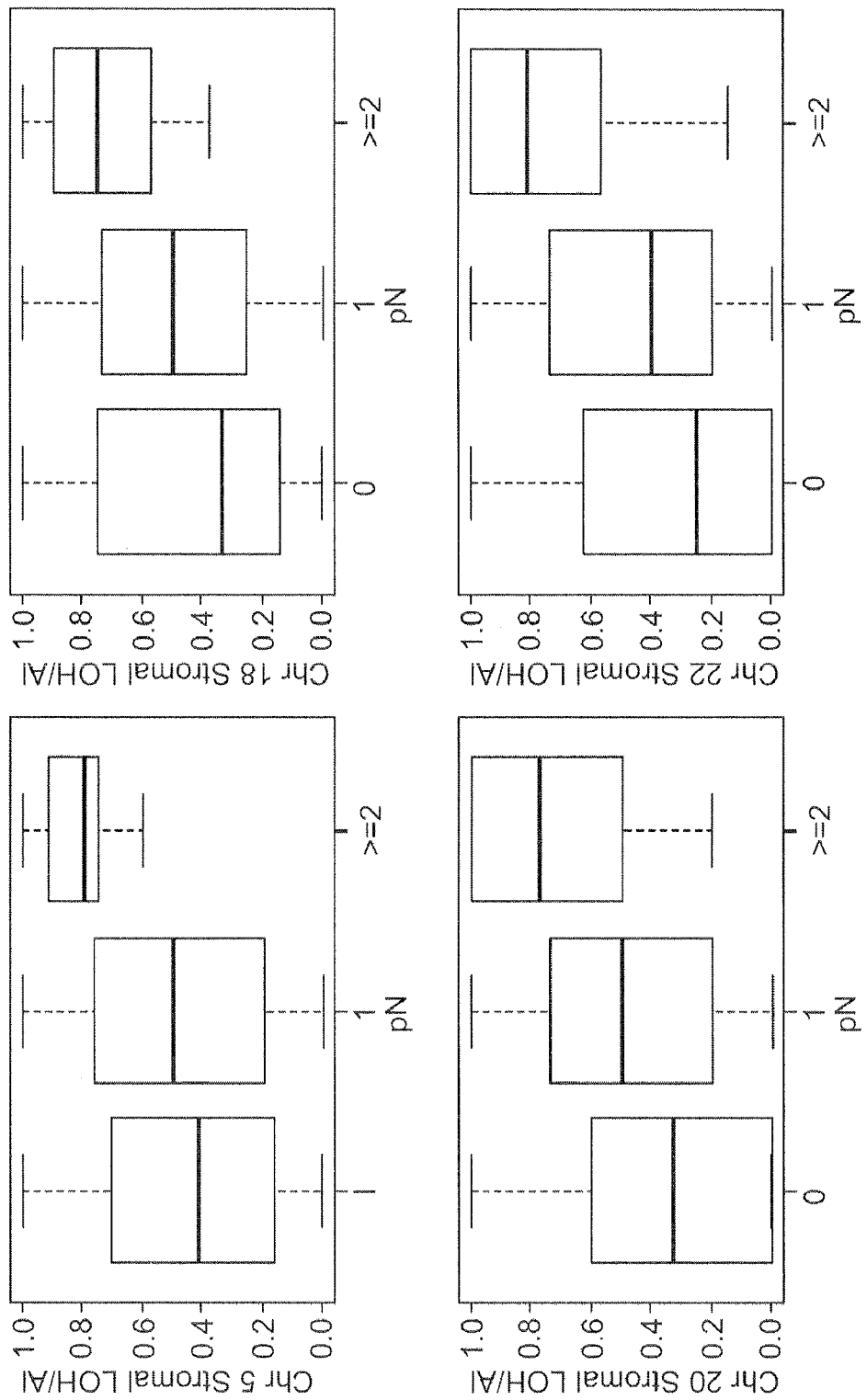

Interestingly, more statistically significant (at the 0.05 level, after Bonferroni adjustment) associations with CPFs were found for LOH/AI in stroma (7 associations) than that in epithelium (1 association). Specifically, significant associations were found between tumor grade and LOH/AI on chromosome 11 in stroma (p=0.0013); LOH/AI on chromosome 14 in epithelium and PR (p=0.002); and LOH/AI on chromosomes 1 (p=0.0006), 2 (p=0.0016), 5 (p=0.0009), 18 (p=0.0009), 20 (p=0.001) and 22 (p=0.0002) in stroma and pathologic regional nodal status (pN) (Table 19, FIGS. 14A-14B).

Once promising chromosomes were identified, the second stage was performed to associate LOH/AI at specific loci and the CPF's. Thus, to determine if specific markers were responsible for the LOH/AI along the chromosomes noted above that were significantly associated with grade, pN and PR status, Fisher's 2-tailed exact tests were used to test the association of the corresponding CPF with LOH/AI at each marker in the corresponding compartment (Table 19). Markers along chromosome 14 in the epithelium associated with PR status were D14S588 (p=0.029) and D14S1426 (p=0.027). Specific markers contributing to the LOH/AI on chromosome 11 in the stroma associating with tumor grade were D11S1999 (p=0.00055) and D11S1986 (p=0.042). Importantly, LOH/AI at various markers in the stroma was significantly associated with pN: ATA42G12 (chromosome 1, p=0.00095), D5S1457 (p=0.00095), D5S1501 (p=0.0011), D5S816 (p=0.0008), D18S858 (p=0.0026), D20S103 (p=0.0027), D20S851 (p=0.0045), D22S683 (p=0.00033) and D22S1045 (p=0.0013) (Table 19).

Eight significant associations were found between compartment-specific, chromosome-specific LOH/AI and CPFs. While only two markers on chromosome 14 in the epithelium were significantly associated with any CPF at all, in this case, PR, genomic instability within 7 chromosomes in the stroma of primary invasive breast carcinomas were significantly associated with tumor grade (chromosome 11) and the presence of regional lymph node metastases (chromosomes 1, 2, 5, 18, 20 and 22). Previous observational studies of total genome LOH/AI in breast cancer compartments have also revealed specific regions of chromosome 11 as an important target of genomic alteration (Kurose, K., et al., *Hum. Mol. Genet.*, 10:1907-1913 (2001); Fukino, K., et al., *Cancer Res.*, 64:7231-7236 (2004)). Furthermore, because this 11q region is also a hotspot of LOH/AI in stroma of head and neck cancers, the role of this region in the stroma might be more universal (Weber, F., et al., *JAMA*, 297:187-195 (2007)). ATM is mapped to chromosomal region 11q23.1, the locus associated with tumor grade. As ATM is responsible for maintaining genomic integrity (Khanna, K., et al. *J. Mammary Gland Biol. Neoplasis*, 9:247-262 (2004)), it may be postulated that LOH/AI at the ATM locus in the stroma might initiate general genomic instability in that compartment. Lack of ATM has also been shown to be associated with increased neoangiogenesis and with increased grade and poor clinical outcome in non-Hodgkins lymphoma (Cuneo, A., et al., *J. Clin. Oncol.*, 18:2607-2614 (2000)). At least one previous study has shown that LOH/AI at the ATM locus correlated with increased grade in whole (ie without compartment-specific analysis) primary breast carcinomas (Rio, P., et al., *Int. J. Oncol.*, 13:849-853 (1998)). However, one should be aware that sometimes, genotype-CPF associations may not be as straightforward as merely reflecting a gene or genes within an identified hot-spot. For example, as described herein a model-based statistic was used to look for potential associations between compartment-specific presence or absence of somatic TP53 mutations and specific hot-spot LOH/AI. Interestingly, the presence of somatic TP53 mutations in the stroma, but not the epithelium, were associated with presence of LOH/AI at our two stroma-specific hotspot markers on chromosome 11 associated with tumor grade (Patocs A and Eng C, unpublished data). Thus, it is possible that somatic mutation of TP53 in the stroma results in genomic instability leading to LOH/AI including LOH/AI at 11q23, affecting the ATM locus which sets up a perpetuating cycle of increasing genomic instability and hence, high grade tumors.

The association of LOH/AI at 9 specific loci residing on 6 chromosomes in the stroma of primary breast carcinomas with pathologic regional lymph node status is worthy of note. In the process of lymph node metastases, there would be at least two rate limiting steps: gaining access to the lymphatics at the site of the primary lesion and tumor formation at the regional lymph node (reviewed in Ref. 31) (Schedin, P., et al., *Breast Cancer Res.*, 6: 93-101 (2004)). For successful metastasis, it would seem straightforward that the primary tumor stroma should have many important roles, providing a permissive microenvironment that permits invasion. The observation that genetic alterations at the 9 loci (on 6 chromosomes) in the stroma associating with pN should reflect the genetically altered microenvironment favorable to metastasis. There are two broad categories of metastasis-associated genes, ie, metastasis activators and metastasis suppressors (reviewed in Ref. 32) (Debies, M., et al., *J. Mammary Gland Biol. Neoplasia*, 6:441-451 (2001)). As an example, at least four of these are located at those chromosomal loci significantly associated with pN in this study, such as Maspin at 18q21.3 (D18S858) (Chen, E., et al., *IUBMB Life*, 58:25-29 (2006)) (Schedin, P., et al., *Breast Cancer Res.*, 6: 93-101 (2004)), EP300 (Krubasik, D., et al., *Br. J. Cancer*, 94:1326-1332 (2006)) at 22q13 (D22S1045), PLCB1 (Cocco, L., et al., *Adv. Enzyme Regul.*, 45:126-135 (2005)) at D20S851 as well or indeed MYH9 (Canobbio, I., et al., *J Thromb. Haemost.*, 3:1026-1035 (2005)) on D22S683, which are known to be associated with metastasis and/or invasion. In particular, EP300 encodes p300 which is a transcriptional co-factor and prototype histone acetyltransferase which plays a role in multiple cellular processes. In vitro, p300-deficient cells appeared to have an aggressive phenotype with loss of cell-cell adhesion and defects in cell-matrix adhesion (Krubasik, D., et al., *Br. J. Cancer*, 94:1326-1332 (2006)). In vivo, embryos lacking p300 were shown to arrest development and die between E8.5 and E11, suggesting that p300 would be necessary for normal organ development (Yao, T., et al., *Cell*, 93:361-372 (1998)). The observation herein might also explain why some groups believe that epigenetic phenomena are more prominent in tumor stroma (Allinen, M., et al., *Cancer Cell.*, 6: 17-32 (2004); Hu, M., et al., *Nat. Genet.*, 37: 899-905 (2005)). However, our current data would suggest that structural loss of such genes as EP300 occur first, with consequent epigenetic alterations important in tumor stroma occurring thereafter. It is also intriguing that within or close to 7 of the 9 pN-associated markers lie genes or loci associated with immune modulation, eg IL2RB, IBD5 (The AutoImmune Disease Database; http://www.uni-rostock.de/aidb/home.php) and several quantitative trait loci for rheumatoid arthritis (Cornelis, F., et al., *Proc. Natl. Acad. Sci. U S A.*, 95:10746-10750 (1998); Shiozawa, S., et al., *Int. Immunol.*, 10:1891-1895 (1998)). Overall, therefore, the observations described herein lend evidence that genetic alterations in the tumor stroma activates/promotes genomic instability and neovascularization (ATM locus LOH/AI and tumor grade) followed by further dysfunction in such genes as EP300 and Maspin whose consequences interact with inflammation and immune suppressive responses (IL2RB, IBD5, and quantitative trait loci for rheumatoid arthritis) which promotes cell migration and invasion.

These results, therefore, support a model in which genetic changes in both stromal and epithelial compartments occur during tumorigenesis, and progression is codetermined by local interaction between these cell populations within the primary tumor (Fukino, K., et al., *Cancer Res.*, 64:7231-7236 (2004)). It was previously found that stroma had a greater multiplicity of genetic alterations than epithelium and the targets of genetic alterations in stroma were more numerous and widely distributed than those in the epithelium. This indicates that epithelium only requires a small number of LOH/AI events to undergo malignant transformation, but local behavior of the resultant epithelial neoplasm is substantially modified by a broader repertoire of genetic changes in adjacent stroma. The data herein indicate that clinical tumor progression, as reflected in the measured clinicopathologic features, may be more influenced by locally acquired changes in the stromal environment than carcinoma cell genotype per se (Fukino, K., et al., *Cancer Res.*, 64:7231-7236 (2004)). Stromal genetic changes that contribute to clinically relevant outcomes can be mapped to particular chromosomal loci, including two markers on chromosome 11 that correlate with tumor grade and nine markers on six chromosomes associated with regional lymph node metastasis. Genetic changes acquired in stroma adjacent to transformed epithelial cells contribute an additional dimension of progression modulation beyond that contributed by the carcinoma cells themselves. The combination of stromal and epithelial genetic changes produces a greater range of outcome scenarios than can otherwise be explained by carcinoma cell genotype alone.

The genetics and genomics of tumor stroma from human patients is a relatively new field of exploration compared to the cell biology of epithelial-stromal interactions in in vitro and non-human solid tumor models which may date back to 20 or more years. Given the technology of the day, albeit modern, there are always caveats to studies such as this. For example, despite our every care to detail to avoid cross contamination between compartments, there might be a few stray cells from each. When this occurs, very low level LOH/AI (eg, in subpopulations) will be missed, and so subtle CPF-associations may be missed. Furthermore, we utilized a 385-marker total genome coverage (10-Mb mean inter-marker distance), and so, it is possible that a few important regions or genes that are relatively distant from each marker will be missed. For example, the 17q markers closest to the HER2/NEU gene showed a relatively low AI (genomic amplification) frequency compared to HER2/neu protein expression by immunohistochemistry. It is believed that the 386-marker whole genome coverage still did not have enough resolution to capture the 1 Mb HER2/NEU amplicon as this marker set did not have include a marker within this gene. Added confidence is provided by similar findings of reproducible genomic, epigenomic and expressional changes found by different technologies such as CGH and expression profiling in breast and other carcinomas published by several other groups (Allinen, M., et al., Cancer Cell., 6: 17-32 (2004); Hu, M., et al., Nat. Genet., 37: 899-905 (2005); Wernert, N., et al., Anticancer Res., 21:2259-2264 (2001)). Nonetheless, as with any patient-oriented study, the data can be further validated, perhaps with emerging novel technologies, in larger series especially those with event-free survival data and therapeutic trials with long follow-up.

TABLE 18

Comparisons between LOH/AI in Neoplastic Epithelium and in Stroma at the Chromosome Level

| Chr. | Frequency of LOH/AI | | Probability of LOH/AI | | p-value of comparison between Epithelium & Stroma |
|---|---|---|---|---|---|
| | Epithelium | Stroma | Epithelium | Stroma | |
| 1  | 0.507 | 0.467 | 0.509 | 0.49  | 0.2 |
| 2  | 0.473 | 0.476 | 0.482 | 0.505 | 0.14 |
| 3  | 0.504 | 0.503 | 0.502 | 0.52  | 0.20 |
| 4  | 0.531 | 0.497 | 0.534 | 0.519 | 0.43 |
| 5  | 0.532 | 0.485 | 0.534 | 0.513 | 0.27 |
| 6  | 0.526 | 0.518 | 0.524 | 0.538 | 0.43 |
| 7  | 0.477 | 0.499 | 0.486 | 0.53  | 0.0035* |
| 8  | 0.553 | 0.472 | 0.558 | 0.502 | 0.0021 |
| 9  | 0.522 | 0.504 | 0.53  | 0.526 | 0.84 |
| 10 | 0.508 | 0.481 | 0.514 | 0.513 | 0.93 |
| 11 | 0.493 | 0.466 | 0.503 | 0.489 | 0.45 |
| 12 | 0.48  | 0.453 | 0.481 | 0.469 | 0.50 |
| 13 | 0.547 | 0.443 | 0.562 | 0.48  | 0.00010 |
| 14 | 0.541 | 0.508 | 0.535 | 0.511 | 0.27 |
| 15 | 0.532 | 0.492 | 0.536 | 0.516 | 0.35 |
| 16 | 0.506 | 0.437 | 0.51  | 0.457 | 0.0043* |
| 17 | 0.577 | 0.473 | 0.581 | 0.492 | 6.9E−05 |
| 18 | 0.482 | 0.458 | 0.493 | 0.483 | 0.63 |
| 19 | 0.492 | 0.469 | 0.498 | 0.489 | 0.65 |
| 20 | 0.448 | 0.429 | 0.456 | 0.457 | 0.99 |
| 21 | 0.497 | 0.466 | 0.508 | 0.493 | 0.56 |
| 22 | 0.484 | 0.428 | 0.486 | 0.44  | 0.058 |
| X  | 0.54  | 0.481 | 0.539 | 0.5   | 0.054 |

LOH/AI frequencies, model-based estimates and model-based p-values for comparing the LOH/AI frequencies between 2 compartments on a chromosome basis were significantly higher in epithelium than in stroma for 5 chromosomes (chromosomes 7, 8, 13, 16 and 17) at the 0.05 level (* and underlined). After the Bonferroni adjustment to account for multiple testing by using 0.05/23 as the significance level, the differences in the LOH/AI estimates between epithelium and stroma were still significant for 3 chromosomes (chromosomes 8, 13 and 17, denoted by underline).

TABLE 19

Logistic Regression and Ordinal Regression Models Reveal Association between Clinicopathological Features and Compartment-Specific LOH/AI at Specific Markers at the Chromosome Level

| Chr. | Stage grouping Direction/p-value | | Grade Direction/p-value | | pN Direction/p-value | |
|---|---|---|---|---|---|---|
| | Epithelium | Stroma | Epithelium | Stroma | Epithelium | Stroma |
| 1  | −1/0.8022 | 1/0.9238  | −1/0.2490 | −1/0.0450* | 1/0.0151  | 1/6.00E−04 |
| 2  | 1/0.4911  | −1/0.7982 | −1/0.2319 | −1/0.1097  | 1/0.0385* | 1/0.0016 |
| 3  | 1/0.2726  | 1/0.5463  | −1/0.7756 | −1/0.0530  | 1/0.0608  | 1/0.0038* |
| 4  | 1/0.4623  | −1/0.9365 | 1/0.6974  | −1/0.1385  | 1/0.0540  | 1/0.0061* |
| 5  | 1/0.6542  | 1/0.5300  | −1/0.5745 | −1/0.0175  | 1/0.0725  | 1/9.00E−04 |
| 6  | 1/0.1835  | 1/0.7566  | −1/0.9789 | −1/0.1893  | 1/0.0324* | 1/0.0089* |
| 7  | −1/0.5637 | −1/0.8235 | −1/0.2397 | −1/0.1155  | 1/0.1005  | 1/0.0115* |
| 8  | 1/0.3169  | 1/0.8170  | 1/0.3608  | −1/0.2009  | 1/0.0058* | 1/0.0025* |
| 9  | 1/0.3256  | −1/0.6632 | 1/0.9130  | −1/0.0927  | 1/0.0218* | 1/0.0192* |
| 10 | 1/0.1994  | −1/0.6173 | 1/0.3457  | −1/0.0098* | 1/0.0194* | 1/0.0042* |
| 11 | −1/0.7846 | −1/0.1375 | −1/0.7341 | −1/0.0013  | 1/0.2961  | 1/0.0642 |
| 12 | 1/0.2386  | −1/0.5988 | −1/0.5833 | −1/0.0449* | 1/0.0120* | 1/0.0085* |
| 13 | 1/0.7693  | −1/0.5967 | 1/0.8873  | −1/0.3289  | 1/0.0651  | 1/0.1704 |
| 14 | 1/0.5447  | 1/0.2882  | 1/0.0689  | −1/0.3861  | 1/0.3827  | 1/0.0026* |
| 15 | 1/0.7068  | 1/0.9220  | 1/0.1517  | −1/0.2087  | 1/0.0505  | 1/0.0031* |
| 16 | 1/0.5991  | −1/0.9970 | −1/0.1644 | −1/0.9381  | 1/0.0054* | 1/0.0199* |
| 17 | 1/0.0259* | 1/0.5742  | 1/0.0155* | −1/0.2215  | 1/0.0447* | 1/0.0051* |
| 18 | 1/0.6436  | −1/0.9334 | −1/0.7684 | −1/0.0087* | 1/0.0354* | 1/9.00E−04 |
| 19 | −1/0.6225 | −1/0.2881 | 1/0.9831  | −1/0.6055  | 1/0.1298  | 1/0.0130* |
| 20 | 1/0.6820  | 1/0.8607  | −1/0.3490 | −1/0.0462* | 1/0.0679  | 1/0.0010 |
| 21 | 1/0.6836  | 1/0.4954  | −1/0.4756 | −1/0.3321  | 1/0.0252* | 1/0.0039* |
| 22 | 1/0.3044  | 1/0.5739  | −1/0.0363* | −1/0.2581 | 1/0.0294* | 1/2.00E−04 |
| X  | 1/0.3868  | −1/0.4650 | 1/0.3700  | −1/0.3088  | 1/0.1247  | 1/0.0173* |

TABLE 19-continued

| | ER Direction/p-value | | PR Direction/p-value | | HER2/neu Direction/p-value | |
|---|---|---|---|---|---|---|
| Chr. | Epithelium | Stroma | Epithelium | Stroma | Epithelium | Stroma |
| 1 | 1/0.3072 | 1/0.0153* | −1/0.9877 | 1/0.0914 | 1/0.8663 | −1/0.8937 |
| 2 | 1/0.2986 | 1/0.0547 | 1/0.6011 | 1/0.2755 | −1/0.7121 | 1/0.7055 |
| 3 | −1/0.5800 | 1/0.3036 | −1/0.2314 | 1/0.5035 | −1/0.5807 | 1/0.8085 |
| 4 | −1/0.4282 | 1/0.0508 | −1/0.7573 | 1/0.1130 | −1/0.3593 | −1/0.5653 |
| 5 | −1/0.5874 | 1/0.0291* | −1/0.8853 | 1/0.2293 | −1/0.3775 | 1/0.4350 |
| 6 | 1/0.2354 | 1/0.1274 | 1/0.8118 | 1/0.4992 | 1/0.4807 | −1/0.7607 |
| 7 | 1/0.2164 | 1/0.0437* | 1/0.7783 | 1/0.2379 | 1/0.4458 | −1/0.8926 |
| 8 | 1/0.7421 | 1/0.1471 | −1/0.7201 | 1/0.5528 | 1/0.8631 | −1/0.9428 |
| 9 | −1/0.5940 | 1/0.0473* | −1/0.6874 | 1/0.0583 | −1/0.1773 | −1/0.5156 |
| 10 | −1/0.6192 | 1/0.0212* | −1/0.4450 | 1/0.2037 | −1/0.9040 | −1/0.9513 |
| 11 | 1/0.5569 | 1/0.0446* | −1/0.9496 | 1/0.1505 | 1/0.7484 | 1/0.5587 |
| 12 | 1/0.9464 | 1/0.0740 | −1/0.4445 | 1/0.3806 | −1/0.9002 | −1/0.3374 |
| 13 | −1/0.6319 | 1/0.2889 | −1/0.6118 | 1/0.6842 | −1/0.7068 | 1/0.1656 |
| 14 | −1/0.0080* | 1/0.9956 | <u>−1/0.0020</u> | −1/0.9378 | −1/0.2150 | 1/0.3355 |
| 15 | −1/0.3094 | 1/0.0333 | −1/0.4018 | 1/0.2225 | 1/0.8802 | 1/0.9123 |
| 16 | 1/0.3688 | 1/0.2950 | 1/0.1615 | 1/0.7380 | −1/0.1784 | 1/0.6331 |
| 17 | −1/0.0483* | 1/0.0504 | −1/0.1467 | 1/0.0857 | −1/0.5385 | 1/0.9803 |
| 18 | 1/0.4614 | 1/0.0848 | 1/0.9787 | 1/0.2617 | −1/0.9347 | −1/0.7319 |
| 19 | −1/0.8053 | 1/0.1955 | −1/0.1306 | 1/0.3189 | −1/0.6296 | −1/0.8024 |
| 20 | −1/0.9375 | 1/0.1002 | 1/0.7936 | 1/0.0646 | −1/0.2529 | 1/0.9487 |
| 21 | 1/0.3919 | 1/0.0247* | 1/0.8128 | 1/0.1949 | −1/0.8748 | 1/0.3823 |
| 22 | 1/0.4558 | 1/0.0722 | 1/0.4166 | 1/0.1875 | −1/0.0095* | −1/0.9190 |
| X | 1/0.9943 | 1/0.1985 | 1/0.7107 | 1/0.3717 | −1/0.5984 | −1/0.7610 |

Each cell contains the direction of association ('1' or '−1') and a model-based p-value. A positive '1' in Direction indicates that higher LOH/AI frequencies on the chromosome is related to higher grade or stage, more lymph node metastasis, positive ER and PR, and so on. A negative '−1' represents the opposite, ie, inverse relationship. For each chromosome, the p-values for both epithelium and stroma are given, with nominally significant results ($p \leq 0.05$) denoted with an asterisk* and significant results after Bonferroni adjustment ($p \leq 0.05/23$) underlined.

Specific Markers Significantly Associated with Clinicopathologic Features

| IN STROMA | Frequency of LOH/AI (%) | | | |
|---|---|---|---|---|
| Tumor grade | I | II | III | p-value* |
| D11S1999 | 50.0 | 60.9 | 23.3 | 0.00055 |
| D11S1986 | 85.7 | 51.5 | 38.6 | 0.042 |

| pN | 0 | 1 | 2 | 3 | |
|---|---|---|---|---|---|
| ATA42G12 | 25.9 | 47.1 | 100 | 100 | 0.00095 |
| D5S1457 | 28.0 | 48.7 | 100 | NI | 0.00095 |
| D5S1501 | 27.0 | 29.3 | 85.7 | 100 | 0.0011 |
| D5S816 | 45.7 | 36.4 | 100 | 100 | 0.0008 |
| D18S858 | 35.9 | 58.6 | 100 | 100 | 0.0026 |
| D20S103 | 16.4 | 21.7 | 62.5 | 100 | 0.0027 |
| D20S851 | 28.8 | 31.9 | 77.8 | 66.7 | 0.0045 |
| D22S683 | 42.2 | 51.5 | 90.9 | NI | 0.00033 |
| D22S1045 | 31.3 | 58.3 | 87.5 | 66.7 | 0.0013 |

| IN EPITHELIUM | Frequency of LOH/AI (%) | | | |
|---|---|---|---|---|
| Progesterone receptor | (+) | (+/−) | (−) | p-value* |
| D14S588 | 32.9 | 50.5 | 57.8 | 0.029 |
| D14S1426 | 40.0 | 62.5 | 68.3 | 0.027 |

*Fisher's 2-tailed Exact Test
NI: No informative data available

The teachings of all patents, published applications and references cited herein and in the provisional application to which priority is claimed are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of diagnosing breast cancer or susceptibility to breast cancer in an individual comprising detecting in a sample that has been obtained from the individual a loss of heterozygosity/allelic imbalance (LOH/AI) at one or more loci selected from the group consisting of: D11S1999, D11S1986, D5S1457, D5S1501, D5S816, D18S858, D20S103, D20S851, D22S683, wherein the presence of the LOH/AI at the one or more loci in the sample of the individual is indicative of a diagnosis of breast cancer in the individual.

2. The method of claim 1 wherein the one or more of the loci are present in epithelial tumor cells, stromal cells surrounding the epithelial tumor cells or a combination thereof.

3. The method of claim 2 wherein the stromal cells are stromal fibroblasts.

4. The method of claim 2 wherein the stromal cells are non-malignant or malignant.

5. The method of claim 1 further comprising determining attributes of the breast cancer.

6. The method of claim 1 wherein the attributes of the breast cancer are tumor aggressiveness, tumor invasion, tumor size, regional lymph node status or a combination thereof.

7. The method of claim 1 wherein the individual is a human.

* * * * *

```
                              SEQUENCE LISTING

<160> NUMBER OF SEQ ID NOS: 117

<210> SEQ ID NO 1
<211> LENGTH: 20
<212> TYPE: DNA
<213> ORGANISM: Artificial Sequence
<220> FEATURE:
<223> OTHER INFORMATION: ACVR1 Primer

<400> SEQUENCE: 1
ttcctcactg agcatcaacg                                                   20

<210> SEQ ID NO 2
<211> LENGTH: 20
<212> TYPE: DNA
<213> ORGANISM: Artificial Sequence
<220> FEATURE:
<223> OTHER INFORMATION: ACVR1 Primer

<400> SEQUENCE: 2
taatgaggcc aacctccaag                                                   20

<210> SEQ ID NO 3
<211> LENGTH: 20
<212> TYPE: DNA
<213> ORGANISM: Artificial Sequence
<220> FEATURE:
<223> OTHER INFORMATION: TSPAN3 Primer

<400> SEQUENCE: 3
agccctgctt ttcatcattg                                                   20

<210> SEQ ID NO 4
<211> LENGTH: 20
<212> TYPE: DNA
<213> ORGANISM: Artificial Sequence
<220> FEATURE:
<223> OTHER INFORMATION: TSPAN3 Primer

<400> SEQUENCE: 4
ttctgaatgc tgcgatcaac                                                   20

<210> SEQ ID NO 5
<211> LENGTH: 20
<212> TYPE: DNA
<213> ORGANISM: Artificial Sequence
<220> FEATURE:
<223> OTHER INFORMATION: EFEMP2 Primer

<400> SEQUENCE: 5
gcccaaacct gtgtcaactt                                                   20

<210> SEQ ID NO 6
<211> LENGTH: 20
<212> TYPE: DNA
<213> ORGANISM: Artificial Sequence
<220> FEATURE:
<223> OTHER INFORMATION: EFEMP2 Primer
```

-continued

<400> SEQUENCE: 6
atgaaggctg ctctcgacat                                                     20

<210> SEQ ID NO 7
<211> LENGTH: 20
<212> TYPE: DNA
<213> ORGANISM: Artificial Sequence
<220> FEATURE:
<223> OTHER INFORMATION: CFLAR Primer

<400> SEQUENCE: 7
tttctttgcc tccatcttgg                                                     20

<210> SEQ ID NO 8
<211> LENGTH: 20
<212> TYPE: DNA
<213> ORGANISM: Artificial Sequence
<220> FEATURE:
<223> OTHER INFORMATION: CFLAR Primer

<400> SEQUENCE: 8
gaagctcaca agggtcttgc                                                     20

<210> SEQ ID NO 9
<211> LENGTH: 22
<212> TYPE: DNA
<213> ORGANISM: Artificial Sequence
<220> FEATURE:
<223> OTHER INFORMATION: GAPDH Primer

<400> SEQUENCE: 9
gggctgcttt taactctggt aa                                                  22

<210> SEQ ID NO 10
<211> LENGTH: 22
<212> TYPE: DNA
<213> ORGANISM: Artificial Sequence
<220> FEATURE:
<223> OTHER INFORMATION: GAPDH Primer

<400> SEQUENCE: 10
atgggtggaa tcatattgga ac                                                  22

<210> SEQ ID NO 11
<211> LENGTH: 110
<212> TYPE: DNA
<213> ORGANISM: Unknown
<220> FEATURE:
<223> OTHER INFORMATION: Stem-loop sequence of homosapian (hsa)-mir-192
      MI0000234

<400> SEQUENCE: 11
gccgagaccg agugcacagg gcucugaccu augaauugac agccagugcu cucgucuccc         60
cucuggcugc caauuccaua ggucacaggu auguucgccu caaugccagc                   110

<210> SEQ ID NO 12
<211> LENGTH: 75
<212> TYPE: DNA
<213> ORGANISM: Unknown
<220> FEATURE:
<223> OTHER INFORMATION: Stem-loop sequence of homosapian (hsa)-mir-197
      MI0000239

<400> SEQUENCE: 12
ggcugugccg gguagagagg gcagugggag guaagagcuc uucacccuuc accaccuucu         60
ccacccagca uggcc                                                    75

<210> SEQ ID NO 13
<211> LENGTH: 75
<212> TYPE: DNA
<213> ORGANISM: Unknown
<220> FEATURE:
<223> OTHER INFORMATION: Stem-loop sequence of homosapian (hsa)-mir-328
      MI0000804

<400> SEQUENCE: 13
uggagugggg gggcaggagg ggcucaggga gaaagugcau acagcccug gcccucucug     60 cccuuccguc cccug                                                    75

<210> SEQ ID NO 14
<211> LENGTH: 95
<212> TYPE: DNA
<213> ORGANISM: Unknown
<220> FEATURE:
<223> OTHER INFORMATION: Stem-loop sequence of homosapian (hsa)-mir-346
      MI0000826

<400> SEQUENCE: 14
ggucucugug uugggcgucu gucugcccgc augccugccu cucuguugcu cugaaggagg    60
caggggcugg gccugcagcu gccugggcag agcgg                              95

<210> SEQ ID NO 15
<211> LENGTH: 21
<212> TYPE: DNA
<213> ORGANISM: Unknown
<220> FEATURE:
<223> OTHER INFORMATION: Mature miR sequence of hsa-miR-192 (Chr.
      11q13.1)

<400> SEQUENCE: 15
cugaccuaug aauugacagc c                                             21

<210> SEQ ID NO 16
<211> LENGTH: 22
<212> TYPE: DNA
<213> ORGANISM: Unknown
<220> FEATURE:
<223> OTHER INFORMATION: Mature miR sequence of hsa-miR-197 (Chr.
      1p13.3)

<400> SEQUENCE: 16
uucaccaccu ucuccaccca gc                                            22

<210> SEQ ID NO 17
<211> LENGTH: 23
<212> TYPE: DNA
<213> ORGANISM: Unknown
<220> FEATURE:
<223> OTHER INFORMATION: Mature miR sequence of hsa-miR-346 (Chr.
      10q23.2)

<400> SEQUENCE: 17
ugucugcccg caugccugcc ucu                                           23

<210> SEQ ID NO 18
<211> LENGTH: 22
<212> TYPE: DNA
<213> ORGANISM: Unknown
<220> FEATURE:
<223> OTHER INFORMATION: Mature miR sequence of hsa-miR-328 (Chr.
      16q22.1)

-continued

```
<400> SEQUENCE: 18
cuggcccucu cugcccuucc gu                                              22

<210> SEQ ID NO 19
<211> LENGTH: 9
<212> TYPE: DNA
<213> ORGANISM: Unknown
<220> FEATURE:
<223> OTHER INFORMATION: PTEN Block 1 Haplotype
<220> FEATURE:
<221> NAME/KEY: misc_feature
<222> LOCATION: (0)...(0)
<223> OTHER INFORMATION: n = Inosine

<400> SEQUENCE: 19 gacccctgn                                                              9

<210> SEQ ID NO 20
<211> LENGTH: 9
<212> TYPE: DNA
<213> ORGANISM: Unknown
<220> FEATURE:
<223> OTHER INFORMATION: PTEN Block 1 Haplotype

<400> SEQUENCE: 20 gatgtctgd                                                              9

<210> SEQ ID NO 21
<211> LENGTH: 9
<212> TYPE: DNA
<213> ORGANISM: Unknown
<220> FEATURE:
<223> OTHER INFORMATION: PTEN Block 1 Haplotype

<400> SEQUENCE: 21 tttgtctgd                                                              9

<210> SEQ ID NO 22
<211> LENGTH: 9
<212> TYPE: DNA
<213> ORGANISM: Unknown
<220> FEATURE:
<223> OTHER INFORMATION: PTEN Block 1 Haplotype
<220> FEATURE:
<221> NAME/KEY: misc_feature
<222> LOCATION: (0)...(0)
<223> OTHER INFORMATION: n = Inosine

<400> SEQUENCE: 22 gaccctcan                                                              9

<210> SEQ ID NO 23
<211> LENGTH: 9
<212> TYPE: DNA
<213> ORGANISM: Unknown
<220> FEATURE:
<223> OTHER INFORMATION: PTEN Block 1 Haplotype

<400> SEQUENCE: 23 gttgtctgd                                                              9

<210> SEQ ID NO 24
<211> LENGTH: 11
<212> TYPE: DNA
<213> ORGANISM: Unknown
<220> FEATURE:
<223> OTHER INFORMATION: PTEN Block 2 Haplotype
```

```
<220> FEATURE:
<221> NAME/KEY: misc_feature
<222> LOCATION: (0)...(0)
<223> OTHER INFORMATION: n = Inosine

<400> SEQUENCE: 24
gcadgantdn a                                                              11

<210> SEQ ID NO 25
<211> LENGTH: 11
<212> TYPE: DNA
<213> ORGANISM: Unknown
<220> FEATURE:
<223> OTHER INFORMATION: PTEN Block 2 Haplotype
<220> FEATURE:
<221> NAME/KEY: misc_feature
<222> LOCATION: (0)...(0)
<223> OTHER INFORMATION: n = Inosine

<400> SEQUENCE: 25
acadggntnn a                                                              11

<210> SEQ ID NO 26
<211> LENGTH: 11
<212> TYPE: DNA
<213> ORGANISM: Unknown
<220> FEATURE:
<223> OTHER INFORMATION: PTEN Block 2 Haplotype
<220> FEATURE:
<221> NAME/KEY: misc_feature
<222> LOCATION: (0)...(0)
<223> OTHER INFORMATION: n = Inosine

<400> SEQUENCE: 26
acangadtdn a                                                              11

<210> SEQ ID NO 27
<211> LENGTH: 11
<212> TYPE: DNA
<213> ORGANISM: Unknown
<220> FEATURE:
<223> OTHER INFORMATION: PTEN Block 2 Haplotype
<220> FEATURE:
<221> NAME/KEY: misc_feature
<222> LOCATION: (0)...(0)
<223> OTHER INFORMATION: n = Inosine

<400> SEQUENCE: 27
agangadtdn a                                                              11

<210> SEQ ID NO 28
<211> LENGTH: 11
<212> TYPE: DNA
<213> ORGANISM: Unknown
<220> FEATURE:
<223> OTHER INFORMATION: PTEN Block 2 Haplotype
<220> FEATURE:
<221> NAME/KEY: misc_feature
<222> LOCATION: (0)...(0)
<223> OTHER INFORMATION: n = Inosine

<400> SEQUENCE: 28
acgdagncnd g                                                              11

<210> SEQ ID NO 29
<211> LENGTH: 8
<212> TYPE: DNA
<213> ORGANISM: Unknown
<220> FEATURE:
<223> OTHER INFORMATION: PTEN Block 3 Haplotype
```

-continued

<400> SEQUENCE: 29 attccctc                                                                8

<210> SEQ ID NO 30
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 30 actccctc                                                                8

<210> SEQ ID NO 31
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 31 attctctc                                                                8

<210> SEQ ID NO 32
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 32 atgtttct                                                                8

<210> SEQ ID NO 33
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 33 atgctccc                                                                8

<210> SEQ ID NO 34
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 34 atgctctc                                                                8

<210> SEQ ID NO 35
<211> LENGTH: 8
<212> TYPE: DNA
<213> ORGANISM: Unknown
<220> FEATURE:
<223> OTHER INFORMATION: PTEN Block 3 Haplotype

<400> SEQUENCE: 35 gttctctc                                                                8

<210> SEQ ID NO 36
<211> LENGTH: 30

```
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 36
gatgtctgdd agangadtdn acactccctc                                              30

<210> SEQ ID NO 37
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 37
gatgtctgdn gcadgantdn atattctctc                                              30

<210> SEQ ID NO 38
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 38
tttgtctgdd acangadtdn atattccctc                                              30

<210> SEQ ID NO 39
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 39
gaccctcann acgdagncnd gtatgtttct                                              30

<210> SEQ ID NO 40
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 40
gatgtctgdn gcadgantdn atgttctctc                                              30

<210> SEQ ID NO 41
<211> LENGTH: 30
```

```
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 41
gatgtctgdn acadggntnn atatgctctc                                30

<210> SEQ ID NO 42
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 42
gatgtctgdn acadggntnn atatgctccc                                30

<210> SEQ ID NO 43
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 43
gacccctgnn acadggntnn atatgctccc                                30

<210> SEQ ID NO 44
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 44
gatgtctgdd acangadtdn atattccctc                                30

<210> SEQ ID NO 45
<211> LENGTH: 30
<212> TYPE: DNA
<213> ORGANISM: Unknown
<220> FEATURE:
<223> OTHER INFORMATION: PTEN Extended Haplotype
<220> FEATURE:
<221> NAME/KEY: misc_feature
<222> LOCATION: (0)...(0)
<223> OTHER INFORMATION: n = Inosine

<400> SEQUENCE: 45
gttgtctgdd acangadtdn atattccctc                                30

<210> SEQ ID NO 46
<211> LENGTH: 20
```

-continued

```
<212> TYPE: DNA
<213> ORGANISM: Unknown
<220> FEATURE:
<223> OTHER INFORMATION: Forward Primer

<400> SEQUENCE: 46
gatagagtct tgctctgtag                                               20

<210> SEQ ID NO 47
<211> LENGTH: 20
<212> TYPE: DNA
<213> ORGANISM: Unknown
<220> FEATURE:
<223> OTHER INFORMATION: Reverse Primer

<400> SEQUENCE: 47
accatacaat atctgccttg                                               20

<210> SEQ ID NO 48
<211> LENGTH: 42
<212> TYPE: DNA
<213> ORGANISM: Unknown
<220> FEATURE:
<223> OTHER INFORMATION: SBE Primer

<400> SEQUENCE: 48
tgccacgtcg tgaaagtctg acaagagtag ctgggactac ag                      42

<210> SEQ ID NO 49
<211> LENGTH: 20
<212> TYPE: DNA
<213> ORGANISM: Unknown
<220> FEATURE:
<223> OTHER INFORMATION: Forward Primer

<400> SEQUENCE: 49
gctgtggtat gtactttctg                                               20

<210> SEQ ID NO 50
<211> LENGTH: 20
<212> TYPE: DNA
<213> ORGANISM: Unknown
<220> FEATURE:
<223> OTHER INFORMATION: Reverse Primer

<400> SEQUENCE: 50
atgcatgaaa cagctacttg                                               20

<210> SEQ ID NO 51
<211> LENGTH: 20
<212> TYPE: DNA
<213> ORGANISM: Unknown
<220> FEATURE:
<223> OTHER INFORMATION: Forward Primer

<400> SEQUENCE: 51
taagtggatc atgcctgtag                                               20

<210> SEQ ID NO 52
<211> LENGTH: 20
<212> TYPE: DNA
<213> ORGANISM: Unknown
<220> FEATURE:
<223> OTHER INFORMATION: Reverse Primer

<400> SEQUENCE: 52
cttaatggat gcagactcag                                               20
```

<210> SEQ ID NO 53
<211> LENGTH: 20
<212> TYPE: DNA
<213> ORGANISM: Unknown
<220> FEATURE:
<223> OTHER INFORMATION: Forward Primer

<400> SEQUENCE: 53
cattctcaag caggactcag                                                    20

<210> SEQ ID NO 54
<211> LENGTH: 20
<212> TYPE: DNA
<213> ORGANISM: Unknown
<220> FEATURE:
<223> OTHER INFORMATION: Reverese Primer

<400> SEQUENCE: 54
aatccacctg cttcagcttc                                                    20

<210> SEQ ID NO 55
<211> LENGTH: 20
<212> TYPE: DNA
<213> ORGANISM: Unknown
<220> FEATURE:
<223> OTHER INFORMATION: Forward Primer

<400> SEQUENCE: 55
actgcaactt tgacctcctg                                                    20

<210> SEQ ID NO 56
<211> LENGTH: 20
<212> TYPE: DNA
<213> ORGANISM: Unknown
<220> FEATURE:
<223> OTHER INFORMATION: Reverse Primer

<400> SEQUENCE: 56
gcagaatctc actctgtcag                                                    20

<210> SEQ ID NO 57
<211> LENGTH: 20
<212> TYPE: DNA
<213> ORGANISM: Unknown
<220> FEATURE:
<223> OTHER INFORMATION: Forward Primer

<400> SEQUENCE: 57
gctgtggttg ctcatcattc                                                    20

<210> SEQ ID NO 58
<211> LENGTH: 20
<212> TYPE: DNA
<213> ORGANISM: Unknown
<220> FEATURE:
<223> OTHER INFORMATION: Reverse Primer

<400> SEQUENCE: 58
caataggaag atacccctgac                                                   20

<210> SEQ ID NO 59
<211> LENGTH: 20
<212> TYPE: DNA
<213> ORGANISM: Unknown
<220> FEATURE:
<223> OTHER INFORMATION: Forward Primer

```
<400> SEQUENCE: 59
cctgatgttt agagaagcag                                              20

<210> SEQ ID NO 60
<211> LENGTH: 23
<212> TYPE: DNA
<213> ORGANISM: Unknown
<220> FEATURE:
<223> OTHER INFORMATION: Reverse Primer

<400> SEQUENCE: 60
cttagattgc tgatcttgtc tcc                                          23

<210> SEQ ID NO 61
<211> LENGTH: 20
<212> TYPE: DNA
<213> ORGANISM: Unknown
<220> FEATURE:
<223> OTHER INFORMATION: Forward Primer

<400> SEQUENCE: 61
actgggcatg ctcagtagag                                              20

<210> SEQ ID NO 62
<211> LENGTH: 20
<212> TYPE: DNA
<213> ORGANISM: Unknown
<220> FEATURE:
<223> OTHER INFORMATION: Reverse Primer

<400> SEQUENCE: 62
agaccaactc tccggcgttc                                              20

<210> SEQ ID NO 63
<211> LENGTH: 20
<212> TYPE: DNA
<213> ORGANISM: Unknown
<220> FEATURE:
<223> OTHER INFORMATION: Forward Primer

<400> SEQUENCE: 63
ttactaaggc taaactggac                                              20

<210> SEQ ID NO 64
<211> LENGTH: 27
<212> TYPE: DNA
<213> ORGANISM: Unknown
<220> FEATURE:
<223> OTHER INFORMATION: Reverse Primer

<400> SEQUENCE: 64
gcgaatcgtc atgtcacagc tcacatg                                      27

<210> SEQ ID NO 65
<211> LENGTH: 20
<212> TYPE: DNA
<213> ORGANISM: Unknown
<220> FEATURE:
<223> OTHER INFORMATION: Forward Primer

<400> SEQUENCE: 65
ggatcacaga tgtaggcttg                                              20

<210> SEQ ID NO 66
<211> LENGTH: 27
```

```
<212> TYPE: DNA
<213> ORGANISM: Unknown
<220> FEATURE:
<223> OTHER INFORMATION: Reverse Primer

<400> SEQUENCE: 66
catcgcctag ctgagagtgt actagac                                         27

<210> SEQ ID NO 67
<211> LENGTH: 20
<212> TYPE: DNA
<213> ORGANISM: Unknown
<220> FEATURE:
<223> OTHER INFORMATION: Forward Primer

<400> SEQUENCE: 67
agttgagaag tctagtacac                                                 20

<210> SEQ ID NO 68
<211> LENGTH: 20
<212> TYPE: DNA
<213> ORGANISM: Unknown
<220> FEATURE:
<223> OTHER INFORMATION: Reverse Primer

<400> SEQUENCE: 68
atcctgtaat cccactctag                                                 20

<210> SEQ ID NO 69
<211> LENGTH: 50
<212> TYPE: DNA
<213> ORGANISM: Unknown
<220> FEATURE:
<223> OTHER INFORMATION: SBE Primer

<400> SEQUENCE: 69
atcgagatcg acccacaatc cactggtcct atagttgtga atatgtttat                50

<210> SEQ ID NO 70
<211> LENGTH: 20
<212> TYPE: DNA
<213> ORGANISM: Unknown
<220> FEATURE:
<223> OTHER INFORMATION: Forward Primer

<400> SEQUENCE: 70
gcaagatagc tagtaccatg                                                 20

<210> SEQ ID NO 71
<211> LENGTH: 20
<212> TYPE: DNA
<213> ORGANISM: Unknown
<220> FEATURE:
<223> OTHER INFORMATION: Reverse Primer

<400> SEQUENCE: 71
aatgccatat gctagcacag                                                 20

<210> SEQ ID NO 72
<211> LENGTH: 20
<212> TYPE: DNA
<213> ORGANISM: Unknown
<220> FEATURE:
<223> OTHER INFORMATION: Foward Primer

<400> SEQUENCE: 72
aggaattcat gtctgatgtg                                                 20
```

<210> SEQ ID NO 73
<211> LENGTH: 20
<212> TYPE: DNA
<213> ORGANISM: Unknown
<220> FEATURE:
<223> OTHER INFORMATION: Reverse Primer

<400> SEQUENCE: 73
gtgactgtac tgctcacttc                                         20

<210> SEQ ID NO 74
<211> LENGTH: 26
<212> TYPE: DNA
<213> ORGANISM: Unknown
<220> FEATURE:
<223> OTHER INFORMATION: SBE Primer

<400> SEQUENCE: 74
gtgcaatcaa attttgtac ctacaa                                   26

<210> SEQ ID NO 75
<211> LENGTH: 27
<212> TYPE: DNA
<213> ORGANISM: Unknown
<220> FEATURE:
<223> OTHER INFORMATION: Forward Primer

<400> SEQUENCE: 75
cgtccgacat tatgcagatg tagactc                                 27

<210> SEQ ID NO 76
<211> LENGTH: 20
<212> TYPE: DNA
<213> ORGANISM: Unknown
<220> FEATURE:
<223> OTHER INFORMATION: Reverse Primer

<400> SEQUENCE: 76
taaacagtcc ttctggcatc                                         20

<210> SEQ ID NO 77
<211> LENGTH: 20
<212> TYPE: DNA
<213> ORGANISM: Unknown
<220> FEATURE:
<223> OTHER INFORMATION: Forward Primer

<400> SEQUENCE: 77
tagcatattc tgactccttc                                         20

<210> SEQ ID NO 78
<211> LENGTH: 20
<212> TYPE: DNA
<213> ORGANISM: Unknown
<220> FEATURE:
<223> OTHER INFORMATION: Reverse Primer

<400> SEQUENCE: 78
gattagccca agagttgtac                                         20

<210> SEQ ID NO 79
<211> LENGTH: 50
<212> TYPE: DNA
<213> ORGANISM: Unknown
<220> FEATURE:
<223> OTHER INFORMATION: SBE Primer

<400> SEQUENCE: 79
agtcttcgag atccagccat catcgactgg tcagtgctgg gattataggc        50

<210> SEQ ID NO 80
<211> LENGTH: 20
<212> TYPE: DNA
<213> ORGANISM: Unknown
<220> FEATURE:
<223> OTHER INFORMATION: Forward Primer

<400> SEQUENCE: 80
tgtaacctgc aggaggcatc                                          20

<210> SEQ ID NO 81
<211> LENGTH: 20
<212> TYPE: DNA
<213> ORGANISM: Unknown
<220> FEATURE:
<223> OTHER INFORMATION: Reverse Primer

<400> SEQUENCE: 81
aaagcagaga ggtaatactc                                          20

<210> SEQ ID NO 82
<211> LENGTH: 26
<212> TYPE: DNA
<213> ORGANISM: Unknown
<220> FEATURE:
<223> OTHER INFORMATION: SBE Primer

<400> SEQUENCE: 82
attacgtaga ctacgaccca ggtagg                                   26

<210> SEQ ID NO 83
<211> LENGTH: 20
<212> TYPE: DNA
<213> ORGANISM: Unknown
<220> FEATURE:
<223> OTHER INFORMATION: Forward Primer

<400> SEQUENCE: 83
acagttgttc acagtggtag                                          20

<210> SEQ ID NO 84
<211> LENGTH: 27
<212> TYPE: DNA
<213> ORGANISM: Unknown
<220> FEATURE:
<223> OTHER INFORMATION: Reverse Primer

<400> SEQUENCE: 84
gtaccgttcc taagcagatt gctcctg                                  27

<210> SEQ ID NO 85
<211> LENGTH: 20
<212> TYPE: DNA
<213> ORGANISM: Unknown
<220> FEATURE:
<223> OTHER INFORMATION: Forward Primer

<400> SEQUENCE: 85
tgcttgttag agtgaggtag                                          20

<210> SEQ ID NO 86
<211> LENGTH: 20

```
<212> TYPE: DNA
<213> ORGANISM: Unknown
<220> FEATURE:
<223> OTHER INFORMATION: Reverse Primer

<400> SEQUENCE: 86
ctagctctat caatcaggtg                                              20

<210> SEQ ID NO 87
<211> LENGTH: 20
<212> TYPE: DNA
<213> ORGANISM: Unknown
<220> FEATURE:
<223> OTHER INFORMATION: Forward Primer

<400> SEQUENCE: 87
aggtaggtat gaatgtactg                                              20

<210> SEQ ID NO 88
<211> LENGTH: 27
<212> TYPE: DNA
<213> ORGANISM: Unknown
<220> FEATURE:
<223> OTHER INFORMATION: Reverse Primer

<400> SEQUENCE: 88
agtcgatatc agactcctct tatcaac                                      27

<210> SEQ ID NO 89
<211> LENGTH: 20
<212> TYPE: DNA
<213> ORGANISM: Unknown
<220> FEATURE:
<223> OTHER INFORMATION: Forward Primer

<400> SEQUENCE: 89
actgcaacct ctacctcctg                                              20

<210> SEQ ID NO 90
<211> LENGTH: 27
<212> TYPE: DNA
<213> ORGANISM: Unknown
<220> FEATURE:
<223> OTHER INFORMATION: Reverse Primer

<400> SEQUENCE: 90
cgtccgcagc tcaatgaact catgtac                                      27

<210> SEQ ID NO 91
<211> LENGTH: 20
<212> TYPE: DNA
<213> ORGANISM: Unknown
<220> FEATURE:
<223> OTHER INFORMATION: Forward Primer

<400> SEQUENCE: 91
gcaactgaat agatgcgtag                                              20

<210> SEQ ID NO 92
<211> LENGTH: 20
<212> TYPE: DNA
<213> ORGANISM: Unknown
<220> FEATURE:
<223> OTHER INFORMATION: Reverse Primer

<400> SEQUENCE: 92
ataactaaca ccatcgtcac                                              20
```

<210> SEQ ID NO 93
<211> LENGTH: 34
<212> TYPE: DNA
<213> ORGANISM: Unknown
<220> FEATURE:
<223> OTHER INFORMATION: SBE Primer

<400> SEQUENCE: 93
cttaatccgt agtcaccatt acttcacctc atct                                34

<210> SEQ ID NO 94
<211> LENGTH: 20
<212> TYPE: DNA
<213> ORGANISM: Unknown
<220> FEATURE:
<223> OTHER INFORMATION: Forward Primer

<400> SEQUENCE: 94
ggtacactac taatcacttg                                                20

<210> SEQ ID NO 95
<211> LENGTH: 20
<212> TYPE: DNA
<213> ORGANISM: Unknown
<220> FEATURE:
<223> OTHER INFORMATION: Reverse Primer

<400> SEQUENCE: 95
tcaccgtgtt agccaggatg                                                20

<210> SEQ ID NO 96
<211> LENGTH: 20
<212> TYPE: DNA
<213> ORGANISM: Unknown
<220> FEATURE:
<223> OTHER INFORMATION: Forward Primer

<400> SEQUENCE: 96
ggaagactag gtattgacag                                                20

<210> SEQ ID NO 97
<211> LENGTH: 20
<212> TYPE: DNA
<213> ORGANISM: Unknown
<220> FEATURE:
<223> OTHER INFORMATION: Reverse Primer

<400> SEQUENCE: 97
aaagagcatc aatgagactc                                                20

<210> SEQ ID NO 98
<211> LENGTH: 20
<212> TYPE: DNA
<213> ORGANISM: Unknown
<220> FEATURE:
<223> OTHER INFORMATION: Forward Primer

<400> SEQUENCE: 98
agaaactgga gcttctcatg                                                20

<210> SEQ ID NO 99
<211> LENGTH: 20
<212> TYPE: DNA
<213> ORGANISM: Unknown
<220> FEATURE:
<223> OTHER INFORMATION: Reverse Primer

<400> SEQUENCE: 99
aaggcaatct gagttatctg                                           20

<210> SEQ ID NO 100
<211> LENGTH: 22
<212> TYPE: DNA
<213> ORGANISM: Unknown
<220> FEATURE:
<223> OTHER INFORMATION: Forward Primer

<400> SEQUENCE: 100
aagacaaagc caaccgatac tt                                        22

<210> SEQ ID NO 101
<211> LENGTH: 24
<212> TYPE: DNA
<213> ORGANISM: Unknown
<220> FEATURE:
<223> OTHER INFORMATION: Reverse Primer

<400> SEQUENCE: 101
ggaaagacta gaagaggcag aagc                                      24

<210> SEQ ID NO 102
<211> LENGTH: 20
<212> TYPE: DNA
<213> ORGANISM: Unknown
<220> FEATURE:
<223> OTHER INFORMATION: Forward Primer

<400> SEQUENCE: 102
cataatacct gctgtggatg                                           20

<210> SEQ ID NO 103
<211> LENGTH: 20
<212> TYPE: DNA
<213> ORGANISM: Unknown
<220> FEATURE:
<223> OTHER INFORMATION: Reverse Primer

<400> SEQUENCE: 103
tcagaccaca gctagtgaac                                           20

<210> SEQ ID NO 104
<211> LENGTH: 50
<212> TYPE: DNA
<213> ORGANISM: Unknown
<220> FEATURE:
<223> OTHER INFORMATION: SBE Primer

<400> SEQUENCE: 104
aagctaggtg ccacgacgag atagtctgag aaccgagttg ggactagggc           50

<210> SEQ ID NO 105
<211> LENGTH: 20
<212> TYPE: DNA
<213> ORGANISM: Unknown
<220> FEATURE:
<223> OTHER INFORMATION: Forward Primer

<400> SEQUENCE: 105
attgcttcgc tcacctgctc                                           20

<210> SEQ ID NO 106
<211> LENGTH: 20

```
<212> TYPE: DNA
<213> ORGANISM: Unknown
<220> FEATURE:
<223> OTHER INFORMATION: Reverse Primer

<400> SEQUENCE: 106
cctttgagat cctcagtaag                                                    20

<210> SEQ ID NO 107
<211> LENGTH: 20
<212> TYPE: DNA
<213> ORGANISM: Unknown
<220> FEATURE:
<223> OTHER INFORMATION: Forward Primer

<400> SEQUENCE: 107
taattctgga gcttcctgag                                                    20

<210> SEQ ID NO 108
<211> LENGTH: 20
<212> TYPE: DNA
<213> ORGANISM: Unknown
<220> FEATURE:
<223> OTHER INFORMATION: Reverse Primer

<400> SEQUENCE: 108
ctgactctat actctgtgag                                                    20

<210> SEQ ID NO 109
<211> LENGTH: 46
<212> TYPE: DNA
<213> ORGANISM: Unknown
<220> FEATURE:
<223> OTHER INFORMATION: SBE Primer

<400> SEQUENCE: 109
atctagatcc acccatactc cgactatcag gctgaggcat gagaat                       46

<210> SEQ ID NO 110
<211> LENGTH: 20
<212> TYPE: DNA
<213> ORGANISM: Unknown
<220> FEATURE:
<223> OTHER INFORMATION: Forward Primer

<400> SEQUENCE: 110
ttggctacaa atgtctctag                                                    20

<210> SEQ ID NO 111
<211> LENGTH: 19
<212> TYPE: DNA
<213> ORGANISM: Unknown
<220> FEATURE:
<223> OTHER INFORMATION: Reverse Primer

<400> SEQUENCE: 111
ggtgctgctg tttactgag                                                     19

<210> SEQ ID NO 112
<211> LENGTH: 20
<212> TYPE: DNA
<213> ORGANISM: Unknown
<220> FEATURE:
<223> OTHER INFORMATION: Forward Primer

<400> SEQUENCE: 112
gtatcgtgga aggactcatg                                                    20
```

```
<210> SEQ ID NO 113
<211> LENGTH: 20
<212> TYPE: DNA
<213> ORGANISM: Unknown
<220> FEATURE:
<223> OTHER INFORMATION: Reverse Primer

<400> SEQUENCE: 113
ggaaattatg ggaaagccag                                                20

<210> SEQ ID NO 114
<211> LENGTH: 22
<212> TYPE: DNA
<213> ORGANISM: Unknown
<220> FEATURE:
<223> OTHER INFORMATION: Forward Primer

<400> SEQUENCE: 114
gtttgattgc tgcatatttc ag                                             22

<210> SEQ ID NO 115
<211> LENGTH: 20
<212> TYPE: DNA
<213> ORGANISM: Unknown
<220> FEATURE:
<223> OTHER INFORMATION: Reverse Primer

<400> SEQUENCE: 115
cctgtatacg ccttcaagtc                                                20

<210> SEQ ID NO 116
<211> LENGTH: 20
<212> TYPE: DNA
<213> ORGANISM: Unknown
<220> FEATURE:
<223> OTHER INFORMATION: Forward Primer

<400> SEQUENCE: 116
cgaactggtg taatgatatg                                                20

<210> SEQ ID NO 117
<211> LENGTH: 20
<212> TYPE: DNA
<213> ORGANISM: Unknown
<220> FEATURE:
<223> OTHER INFORMATION: Reverse Primer

<400> SEQUENCE: 117
tccaggaaga ggaaaggaaa                                                20
```